(12) United States Patent
Fredriksson et al.

(10) Patent No.: US 11,406,665 B2
(45) Date of Patent: Aug. 9, 2022

(54) THERAPEUTIC PEPTIDES THAT TARGET TGF-BETA INTERACTION

(71) Applicant: GENAGON THERAPEUTICS AB, Solna (SE)

(72) Inventors: Johan Erik Simon Fredriksson, Bromma (SE); Olof Andries Blokzijl, Stockholm (SE)

(73) Assignee: GENAGON THERAPEUTICS AB, Solna (SE)

( * ) Notice: Subject to any disclaimer, the term of this patent is extended or adjusted under 35 U.S.C. 154(b) by 279 days.

(21) Appl. No.: 16/477,423

(22) PCT Filed: Jan. 12, 2018

(86) PCT No.: PCT/EP2018/050776
§ 371 (c)(1),
(2) Date: Jul. 11, 2019

(87) PCT Pub. No.: WO2018/130659
PCT Pub. Date: Jul. 19, 2018

(65) Prior Publication Data
US 2019/0328788 A1    Oct. 31, 2019

(30) Foreign Application Priority Data
Jan. 12, 2017  (GB) .................... 1700567

(51) Int. Cl.
*A61K 35/17*   (2015.01)
*C07K 14/495*  (2006.01)
*C07K 14/71*   (2006.01)
*A61K 38/00*   (2006.01)

(52) U.S. Cl.
CPC ............ *A61K 35/17* (2013.01); *C07K 14/495* (2013.01); *C07K 14/71* (2013.01); *A61K 38/00* (2013.01); *C07K 2317/54* (2013.01); *C07K 2317/55* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 6,824,780 B1 | 11/2004 | Devaux et al. | |
| 6,878,515 B1 | 4/2005 | Landegren | |
| 7,306,904 B2 | 12/2007 | Landegren et al. | |
| 8,168,586 B1 | 5/2012 | Fang et al. | |
| 8,192,735 B2 | 6/2012 | Breit et al. | |
| 8,574,857 B2 | 11/2013 | Vandeghinste et al. | |
| 8,946,146 B2 | 2/2015 | Breit et al. | |
| 9,175,076 B2 | 11/2015 | Lerner et al. | |
| 2003/0194704 A1 | 10/2003 | Penn et al. | |
| 2009/0004181 A1 | 1/2009 | Breit | |
| 2010/0029573 A1 | 2/2010 | Weinschenk et al. | |
| 2011/0123454 A1 | 5/2011 | Breit et al. | |
| 2011/0306559 A1 | 12/2011 | Forsayeth et al. | |
| 2014/0099310 A1 | 4/2014 | Fang et al. | |
| 2014/0107181 A1 | 4/2014 | Vandeghinste et al. | |
| 2014/0271818 A1 | 9/2014 | James et al. | |
| 2015/0225483 A1 | 8/2015 | Lo | |
| 2016/0012099 A1 | 1/2016 | Tuatini et al. | |
| 2016/0015784 A1 | 1/2016 | Shaw et al. | |
| 2016/0195546 A1 | 7/2016 | Labaer et al. | |
| 2016/0289320 A1 | 10/2016 | Breit et al. | |

FOREIGN PATENT DOCUMENTS

| | | |
|---|---|---|
| EP | 2441466 A1 | 4/2005 |
| EP | 1734986 A1 | 12/2006 |
| EP | 2360474 A2 | 8/2011 |
| EP | 2386856 A2 | 11/2011 |
| EP | 2774620 A1 | 9/2014 |
| EP | 3105246 A2 | 12/2016 |
| JP | 2008503712 A | 2/2008 |
| JP | 2012021995 A | 2/2012 |
| JP | 5595989 B2 | 9/2014 |
| WO | 01/87930 A2 | 11/2001 |
| WO | 01/90304 A2 | 11/2001 |
| WO | 02/061087 A2 | 8/2002 |
| WO | 2004/039333 A2 | 5/2004 |
| WO | 2004/041170 A2 | 5/2004 |
| WO | 2004/058805 A2 | 7/2004 |
| WO | 2004/106935 A2 | 12/2004 |
| WO | 2005/124342 A2 | 12/2005 |
| WO | 2007/107743 A1 | 9/2007 |
| WO | 2010/048670 A1 | 5/2010 |
| WO | 2012/104261 A1 | 8/2012 |
| WO | 2012/129514 A1 | 9/2012 |
| WO | 2012/152942 A1 | 11/2012 |
| WO | 2013/158970 A2 | 10/2013 |
| WO | 2014/094122 A1 | 6/2014 |

(Continued)

OTHER PUBLICATIONS

Alonso-Merino, Elvira et al., Thyroid hormones inhibit TGF-β signaling and attenuate fibrotic responses, PNAS, pp. E3451-E3460 (published online May 31, 2016).
Araújo-Jorge, Tania C. et al., Pivotal role for TGF-b in infectious heart disease: The case of Trypanosoma cruzi infection and consequent Chagasic myocardiopathy, Cytokine & Growth Factor Reviews, doi:10.1016/j.cytogfr.2008.08.002, pp. 1-9 (2008).
Basile, J. I. et al., Mycobacterium tuberculosis multi-drug-resistant strain M induces IL-17IIFNg-CD41 T cell expansion through an IL-23 and TGF-β- dependent mechanism in patients with MDR-TB tuberculosis, Clinical and Experimental Immunology, vol. 187, pp. 160-173 (Sep. 21, 2016).
Crauwels, Peter et al., Apoptotic-like Leishmania exploit the host's autophagy machinery to reduce T-cell-mediated parasite elimination, Autophagy, vol. 11, No. 2, pp. 285-297 (Feb. 2015).

(Continued)

*Primary Examiner* — Elly-Gerald Stoica
(74) *Attorney, Agent, or Firm* — Porter Wright Morris & Arthur LLP

(57) ABSTRACT

The invention relates to apolypeptide capable of binding to TGF-β for use in treating or preventing a condition associated with elevated or unwanted levels of TGF-β, wherein said polypeptide is capable of inhibiting the interaction of TGF-β with the receptor CLPTM1.

10 Claims, 10 Drawing Sheets

Specification includes a Sequence Listing.

(56) References Cited

FOREIGN PATENT DOCUMENTS

| WO | 2015/108719 A1 | 7/2015 |
| WO | 2015/198199 A1 | 12/2015 |
| WO | 2015/197446 A1 | 12/2016 |
| WO | 2017/013188 A1 | 1/2017 |
| WO | 2018/050852 A2 | 3/2018 |

OTHER PUBLICATIONS

David, Justin M. et al., A novel bifunctional anti-PD-L1/TGF-β Trap fusion protein (M7824) efficiently reverts mesenchymalization of human lung cancer cells, Oncoimmunology, vol. 6, No. 10, pp. e1349589-1-16 (2017).

Elmekki, Miskelyemen A. et al., Elevated TGF-beta levels in drug-resistant visceral leishmaniasis, Annals of Saudi Medicine, vol. 36, No. 1, pp. 1-5 (Jan.-Feb. 2016).

Feruglio, S. L. et al., T Cell Responses and Regulation and the Impact of In Vitro IL-10 and TGF-β Modulation During Treatment of Active Tuberculosis, Scandinavian Journal of Immunology, pp. 138-146 (2016).

Graham, MD, Brian B. et al., TGF-β Signaling Promotes Pulmonary Hypertension Caused by Schistosoma Mansoni, Circulation, vol. 128, No. 12, pp. 1-25 (Sep. 17, 2013).

Hahn, Jennifer M. et al., Partial epithelial-mesenchymal transition in keloid scars: regulation of keloid keratinocyte gene expression by transforming growth factor-β31, Burns & Trauma, vol. 4, No. 30, pp. 1-17 (2016).

Hanks, BA et al., Pharmacological inhibition of TGFβ as a strategy to augment the antitumor immune response, Curr Opin Investig Drugs, vol. 11, No. 12, pp. 1342-1353, pp. 1-2 (Dec. 2010). Abstract.

Lazar, Greg A. et al., Engineered antibody Fc varients with enhanced effector function, PNAS, vol. 103, No. 11, pp. 4005-4010 (Mar. 14, 2006).

Ty, Lee et al., Expression of transforming growth factor beta 1, 2, and 3 proteins in keloids, Ann Plast Surg., vol. 43, No. 2, pp. 179-184 (1999). Abstract.

Lewis, Gavin M. et al., TGF-β receptor maintains CD4 T helper cell identity during chronic viral infections, The Journal of Clinical Investigation, vol. 126, No. 10, pp. 3799-3813 (Oct. 2016).

Lourembam, Sonia D. et al., Dysregulation of cytokines expression in complicated falciparum malaria with increased TGF-β and IFN-y and decreased IL-2 and IL-12, Cytokine, vol. 64, pp. 503-508 (2013).

Maina, Edward K. et al., Plasma concentrations of transforming growth factor beta 1 in non-progressive HIV-1 infection correlates with markers of disease progression, Cytokine, vol. 81, pp. 109-116 (2016).

Markowitz, S. et al., Inactivation of the type II TGF-beta receptor in colon cancer cells with microsatellite instability, Science, vol. 268, No. 5215, pp. 1336-1338 (Jun. 2, 1995). Abstract.

Morris, David G. et al., Loss of integrin avβ6-mediated TGF-β activation causes Mmp12-dependent emphysema, Nature, vol. 422, pp. 169-173 (Mar. 13, 2003).

Muraoka, Rebecca S. et al., Blockade of TGF-β inhibits mammary tumor cell viability, migration, and metastases, J Clin Invest, vol. 109, No. 12, pp. 1551-1559 (2002).

Neuzillet, Cindy et al., Targeting the TGFβ pathway for cancer therapy, Pharmacology & Therapeutics, vol. 147, pp. 22-31 (2015).

Okamura, Tomohisa et al., TGF-β3-expressing CD4+CD25-LAG3+ regulatory T cells control humoral immune responses, Nature Communications, DOI: 10.1038/ncomms7329, pp. 1-14 (Jan. 19, 2015).

Padua, David et al., Roles of TGFβ in metastasis, Cell Research, vol. 19, pp. 89-102 (Jan. 2009).

Radzikowska, E. et al., Cryptogenic Organizing Pneumonia: IL-1β, IL-6, IL-8, and TGF-β1 Serum Concentrations and Response to Clarithromycin Treatment, Advs Exp. Medicine, Biology—Neuroscience and Respiration, vol. 22, pp. 77-85 (published online Mar. 18, 2016).

Rosenberg, Steven A., IL-2: The First Effective Immunotherapy for Human Cancer, J Immunol, vol. 192, No. 12, pp. 5451-5458 (Jun. 15, 2014).

Samarakoon, Rohan et al., Induction of renal fibrotic genes by TGF-β1 requires EGFR activation, p53 and reactive oxygen species, Cellular Signalling, vol. 25, pp. 2198-2209 (Jun. 21, 2013).

Shields, Robert L. et al., High Resolution Mapping of the Binding Site on Human IgG1 for FcyRI, FcyRII, FcyRIII, and FcRn and Design of IgG1 Variants with Improved Binding to the FcyR*, The Journal of Biological Chemistry, vol. 276, No. 9, pp. 6591-6604 (Mar. 2, 2001).

Stewart, Ross et al., A variant human IgGI-Fc mediates improved ADCC, Protein Engineering, Design & Selection, vol. 24, No. 9, pp. 671-678 (published online May 18, 2011).

Strohl, William, Fusion Proteins for Half-Life Extension of Biologies as a Strategy to Make Biobetters, BioDrugs, vol. 29, pp. 215-239 (2015).

Thomas, Dori A. et al., TGF-β directly targets cytotoxic T cell functions during tumor evasion of immune surveillance, Cancer Cell, vol. 8, pp. 369-380 (Nov. 2005).

Thomas, Belinda J. et al., In the Shadow of Fibrosis: Innate Immune Suppression Mediated by Transforming Growth Factor-β, American Journal of Respiratory Cell and Molecular Biology, vol. 55, No. 6 (Dec. 2016).

Uhrlaub, Jennifer L. et al., Dysregulated TGF-β Production Underlies the Age-Related Vulnerability to Chikungunya Virus, PLOS Pathogens, DOI:10.1371/journal.ppat.1005891, pp. 1-17 (Oct. 13, 2016).

Xia, Yuxiu C. et al., Glucocorticoid Insensitivity in Virally Infected Airway Epithelial Cells Is Dependent on Transforming Growth Factor-β Activity, PLOS Pathogens | DOI:10.1371/journal.ppat. 1006138, pp. 1-25 (Jan. 3, 2017).

Young, Kristina H. et al., Tumor immune remodeling by TGFβ inhibition improves the efficacy of radiation therapy, OncoImmunology, vol. 4, No. 3, pp. 1-2 (Mar. 2015).

Ni, Zhenhua et al., CLPTM1L Is Overexpressed in Lung Cancer and Associated with Apoptosis, PLOS One, vol. 7, No. 12, pp. 1-8 (Dec. 2012).

Official Action dated Apr. 3, 2019 from corresponding European Application No. 16741628.8.

Wang, Xiaobing et al.. Macrophage inhibitory cytokine 1 (MIC-1/GDF15) as a novel diagnostic serum biomarker in Pancreatic ductal adenocarcinoma, BMC Cancer, 14:578, pp. 1-11 (2014).

Williams, Carly Bess et al., Tumor-associated macrophages: unwitting accomplices in breast cancer malignancy, npj Breast Cancer 2,15025:pp. 1-12 (published online Jan. 20, 2016).

Yamashita, Toshiharu et al., Macrophage Inhibitory Cytokine-1: A New Player in Melanoma Development, Journal of Investigative Dermatology, 129:262-264 (2009).

Zhang, Yue et al., High-Infiltration of Tumor-Associated Macrophages Predicts Unfavorable Clinical Outcome for Node-Negative Breast Cancer, PLOS One, vol. 8, Issue 9, pp. 1-8 e76147 (Sep. 2013).

Zhou, Zhizhong et al., Growth Differentiation Factor-15 Suppresses Maturation and Function of Dendritic Cells and Inhibits Tumor-Specific Immune Response, PLOS One, vol. 8, Issue 11, pp. 1-13, e78618 (Nov. 2013).

Albertoni, Michele et al., Anoxia induces macrophage inhibitory cytokine-1 (MIC-1) in glioblastoma cells independently of p53 and HIF-1, Oncogene, 21:4212-4219 (2002).

Alonso-Alconada, Lorena et al., Molecular profiling of circulating tumor cells links plasticity to the metastatic process in endometrial cancer, Molecular Cancer, 13:223 (2014).

Altena, Renske et al., Growth Differentiation Factor 15 (GDF-15) Plasma Levels Increase during Bleomycin-and Cisplatin-Based Treatment of Testicular Cancer Patients and Relate to Endothelial Damage, PLOS One, 10(1):e0115372, pp. 1-15 (Jan. 15, 2015).

Baek, Kyoung Eun et al., Upregulation and secretion of macrophage inhibitory cytokine-1 (MIC-1) in gastric cancers, Clinica Chimica Acta, 401:128-133 (2009).

(56) References Cited

OTHER PUBLICATIONS

Barderas, Rodrigo et al., In-depth Characterization of the Secretome of Colorectal Cancer Metastatic Cells Identifies Key Proteins in Cell Adhesion, Migration, and Invasion, Molecular & Cellular Proteomics, 12(6):1602-1620 (2013).
Baribault, Helene et al., The G-Protein-Coupled Receptor GPR103 Regulates Bone Formation, Molecular and Cellular Biology, 26:709-717 (Jan. 2006).
Bian, Xiaofang et al., Tracking the Antibody Immunome in Type 1 Diabetes Using Protein Arrays, J. Proteome Res., 16:195-203 (2017).
Boyle, Glen M. et al., Macrophage Inhibitory Cytokine-1 Is Overexpressed in Malignant Melanoma and Is Associated with Tumorigenicity, Journal of Investigative Dermatology, 129:383-391 (published online Aug. 28, 2008).
Bruzzese, Francesca et al., Local and Systemic Protumorigenic Effects of Cancer-Associated Fibroblast-Derived GDF15, Microenvironment and Immunology, Cancer Res., 74(13):3408-3418 (Jul. 1, 2014).
Bruzzone, Federica et al., Distribution of 26RFa Binding Sites and GPR103 mRNA in the Central Nervous System of the Rat, The Journal of Comparative Neurology, 503:573-591 (2007).
Chudeka-Glaz et al., Assessment of selected cytokines, proteins, and growth factors in the peritoneal fluid of patients with ovarian cancer and benign gynecological conditions, OncoTargets and Therapy, 8:471-485 (2015).
Corre, Jill et al., Bioactivity and Prognostic Significance of Growth Differentiation Factor GDF15 Secreted by Bone Marrow Mesenchymal Stem Cells in Multiple Myeloma, American Association for Cancer Research, 72(6): 1395-1406 (2012).
Corre, Jill et al., Concise Review: Growth Differentiation Factor 15 in Pathology: A Clinical Role?, Stem Cells Translational Medicine, 2:946-952 (2013).
Costa, Vera L. et al., Three Epigenetic Biomarkers, GDF15, TMEFF2, and VIM, Accurately Predict Bladder Cancer from DNA-Based Analyses of Urine Samples, Clin Cancer Res, 16(23):5842-5852 (Dec. 1, 2010).
Creelan Benjamin C., Update on Immune Checkpoint Inhibitors in Lung Cancer, Cancer Control, vol. 21, No. 1, pp. 80-89 (Jan. 2014).
Finkenstedt, Armin et al., Regulation of iron metabolism through GDF15 and hepcidin in pyruvate kinase deficiency, British Journal of Haematology, 144:789-793 (published online Dec. 22, 2008).
Fisher, O M, MIC-1/GDF15 in Barrett's oesophagus and oesophageal adenocarcinoma, British Journal of Cancer, 112:1384-1391 (2015).
Folgueira, Maria Aparecida Azevedo Koike et al., Gene Expression Profile Associated with Response to Doxorubicin Based Therapy in Breast Cancer, Clin Cancer Res, 11(20):7434-7444 (Oct. 15, 2005).
Kadara, Humam, Induction of GDF-15/NAG-1/MIC-1 in Human Lung Carcinoma Cells by Retinoid-Related Molecules and Assessment of Its Role in Apoptosis, Cancer Biology & Therapy, 5(5):518-522 (May 2006).
Karan, Dev et al., Macrophage Inhibitory Cytokine-1: Possible Bridge Molecule of Inflammation and Prostate Cancer, Cancer Res, 69(1):1-6 (Jan. 1, 2009).
Kim, Kwang-Kyu et al., Macrophage inhibitory cytokine-1 activates AKT and ERK-1/2 via the transactivation of ErbB2 in human breast and gastric cancer cells, Carcinogenesis, vol. 29, No. 4, pp. 704-712 (2008).
Puskás, László G. et al., Novel Anti-CRR9/CLPTM1L Antibodies with Antitumorigenic Activity Inhibit Cell Surface Accumulation, PI3K Interaction, and Survival Signaling, Molecular Cancer Therapeutics, 15:985-998 (published online Mar. 3, 2016).
Ramirez, Jean-Marie et al., Growth differentiation factor 15 production is necessary for normal erythroid differentiation and is increased in refractory anaemia with ring-sideroblasts, British Journal of Haematology, 144:251-262 (published online Nov. 19, 2008).
Reimer, Elisa et al., Identification and characterization of proteins involved in proper functioning of UNC93B-Toll-like receptor complexes, PhD Thesis, Technical University Braunschweig, pp. 1-166 (2014).

Roth, P et al., GDF-15 contributes to proliferation and immune escape of malignant gliomas, Clinical Cancer Research, 16(5):3851-3859 (2010) (Reprint).
Savina, Ariel et al., The exosome pathway in K562 cells is regulated by Rab11, Journal of Cell Science, 115(12):2505-2515 (Apr. 1, 2002).
Savina, Ariel et al., Rab11 Promotes Docking and Fusion of Multivesicular Bodies in a Calcium-Dependent Manner, Traffic, 6:131-143 (2005).
Schiegniiz, Eik et al., Growth differentiation factor 15 as a radiation-induced marker in oral carcinoma increasing radiation resistance, Journal of Oral Pathology & Medicine, pp. 1-7 (2015).
Selander, Katri S. et al., Serum Macrophage Inhibitory Cytokine-1 Concentrations Correlate with the Presence of Prostate Cancer Bone Metastases, Cancer Epidemiol Biomarkers & Prevention, 16(3):532-538 (Mar. 2007).
Si, Youhui et al., Growth Differentiation Factor 15 Is Induced by Hepatitis C Virus Infection and Regulates Hepatocellular Carcinoma-Related Genes, PLOS One, vol. 6, Issue 5, e19967, pp. 1-9 (May 2011).
Takayasu, Shinobu et al., A neuropeptide ligand of the G protein-coupled receptor GPR103 regulates feeding, behavioral arousal, and blood pressure in mice, PNAS, vol. 103, No. 19, pp. 7438-7443 (May 9, 2006).
Tamary, Hannah et al., Elevated growth differentiation factor 15 expression in patients with congenital dyserythropoietic anemia type I, Blood, 112(13):5241-5244 (Dec. 15, 2008).
Tanno, Toshihiko et al., High levels of GDF15 in thalassemia suppress expression of the iron regulatory protein hepcidin, Nature Medicine, vol. 13, No. 9, pp. 1096-1101 (Sep. 2007).
Tanno, Toshihiko et al., Growth differentiating factor 15 enhances the tumor-initiating and self-renewal potential of multiple myeloma cells, Blood, vol. 123, No. 5, pp. 725-734 (Jan. 30, 2014).
Tawfik, H.M. et al., Expression of Macrophage Inhibitory Cytokine-1 in Benign and Malignant Prostatic Tissues: Implications for Prostate Carcinogenesis and Progression of Prostate Cancer, International Journal of Cancer Research, 6(3):141-153 (2010).
Tsai Vicky W. W. et al., Anorexia/cachexia of chronic diseases: a role for the TGF-B family cytokine MIC-1/GDF15, J Cachexia Sarcopenia Muscle, 3:239-243 (2012).
Ukena, Kazuyoshi et al., Identification, localization and function of a novel neuropeptide, 26 RFa, and its cognate receptor, GPR103, in the avian Hypothalamus, General and Comparative Endocrinology, 190:42-46 (2013).
Urakawa, Naoki et al., GDF15 derived from both tumor-associated macrophages and esophageal squamous cell carcinomas contributes to tumor progression via Akt and Erk pathways, Laboratory Investigation, vol. 95, pp. 491-503 (May 2015).
Vanhara, P et al., Growth/differentiation factor-15: prostate cancer suppressor or promoter?, Prostate Cancer and Prostatic Diseases, 15:320-328 (2012).
Wakchoure S et al., Expression of macrophage inhibitory cytokine-1 in prostate cancer bone metastases induces osteoclast activation and weight loss, Prostate, 69(6):652-61 (May 2009).
Santa Cruz Biotechnology et al, CLPTM1 (G-7): sc-374619, retrieved from http://www.ld211.com/upload/file/20140313/20140313103107_26443.pdf (published online Mar. 13, 2014).
Lipowska-Bhalla et al, Cancer Immunology, Immunotherapy, 61(7):953-962 (2012).
Sorbal et al, Acta Veterinaria Scandinavica, 50(1):27 (pp. 1-9) (2008).
Pearson, William R. et al., Improved tools for biological sequence comparison, Proc. Natl. Acad. Sci., vol. 85, pp. 2444-2448 (Apr. 1988).
Aihara, Ken-ichi et al., Transforming Growth Factor-β1 as a Common Target Molecule for Development of Cardiovascular Diseases, Renal Insufficiency and Metabolic Syndrome, Cardiology Research and Practice, vol. 2011, Article ID. 175381, pp. 1-9 (2011).
Altschul, Stephen F. et al., Gapped BLAST and PSI-BLAST: a new generation of protein database search programs, Nucleic Acids Research, vol. 25, No. 17, pp. 3389-3402 (1997).

(56) References Cited

OTHER PUBLICATIONS

Adela, Ramu et al., GDF-15 as a Target and Biomarker for Diabetes and Cardiovascular Diseases: A Translational Prospective, Journal of Diabetes Research, vol. 2015, Article ID 490842, pp. 1-14 (2015).
Chen, Huihui et al., Activation of STAT6 by STING Is Critical for Antiviral Innate Immunity, Cell, vol. 147, pp. 436-446 (Oct. 14, 2011).
Elchebly, Mounib et al., Increased Insulin Sensitivity and Obesity Resistance in Mice Lacking the Protein Tyrosine Phosphatase-1B Gene, Science, vol. 283, pp. 1544-1548 (1999).
Elias, Ivet et al., Adipose Tissue Overexpression of Vascular Endothelial Growth Factor Protects Against Diet-Induced Obesity and Insulin Resistance, Diabetes, vol. 61, pp. 1801-1813 (Jul. 2012).
Goldstein, Barry J. et al., Tyrosine Dephosphorylation and Deactivation of Insulin Receptor Substrate-1 by Protein-tyrosine Phosphatase 1B, The Journal of Biological Chemistry, vol. 275, No. 6, pp. 4283-4289 (Feb. 11, 2000).
Gomez, Elodie et al., Reduction of heart failure by pharmacological inhibition or gene deletion of protein tyrosine phosphatase 1B, Journal of Molecular and Cellular Cardiology, vol. 52, pp. 1257-1264 (2012).
Holm, Liisa et al., Touring protein fold space with Dali/FSSP, Nucleic Acids Research, vol. 26, No. 1, pp. 316-319 (1998).
IPO Search Report, Genagon Therapeutics AB, pp. 1-5 (dated Jun. 8, 2017).
Jin, Lei et al., MPYS, a Novel Membrane Tetraspanner, Is Associated with Major Histocompatibility Complex Class II and Mediates Transduction of Apoptotic Signals, Molecular and Cellular Biology, vol. 28, No. 16, pp. 5014-5026 (2008).
Klaman, Lori D. et al., Increased Energy Expenditure, Decreased Adiposity, and Tissue-Specific Insulin Sensitivity in Protein-Tyrosine Phosphatase IB-Deficient Mice, Molecular and Cellular Biology, vol. 20, No. 15, pp. 5479-5489 (Aug. 2000).
Lanahan, Anthony A. et al., VEGF receptor 2 endocytic trafficking regulates arterial morphogenesis, Dev Cell., vol. 18, No. 5, pp. 713-724 (May 18, 2010).
Li, Yang et al., Regulating STING in health and disease, Journal of Inflammation, vol. 14, No. 11, pp. 1-21 (2017).
Myers, Eugene W. et al., Optimal alignments in linear space, CABIOS, vol. 4, No. 1, pp. 11-17 (1988).
Paludan, Soren R. et al., Immune sensing of DNA, Immunity, vol. 38, No. 5, pp. 870-880 (May 23, 2013).
Thiebaut, Pierre-Alain et al., Role of protein tyrosine phosphatase 1B in cardiovascular diseases, Journal of Molecular and Cellular Cardiology, vol. 101, pp. 50-57 (2016).
Wang, James Q. et al., Inhibiting TLR9 and other UNC93B1-dependent TLRs paradoxically increases accumulation of MYD88L265P plasmablasts in vivo, Blood, vol. 128, No. 12, pp. 1604-1608 (Sep. 22, 2016).
Briet, Samuel N. et al., Macrophage inhibitory cytokine-1 (MIC-1/GDF15) and mortality in end-stage renal disease, Nephrol Dial Transplant, vol. 27, pp. 70-75 (2012).
Mazagova, Magdalena et al., Genetic deletion of growth differentiation factor 15 augments renal damage in both type 1 and type 2 models of diabetes, Am J Physiol Renal Physiol, vol. 305, pp. F1249-F1264 (2013).
Abulizi, Palida et al., Growth Differentiation Factor-15 Deficiency Augments Inflammatory Response and Exacerbates Septic Heart and Renal Injury Induced by Lipopolysaccharide, Scientific Reports, vol. 7, No. 1037, pp. 1-10 (2016).
Zimmers, Teresa A. et al., Growth Differentiation Factor-15/Macrophage Inhibitory Cytokine-1 Induction After Kidney and Lung Injury, SHOCK, vol. 23, No. 6, pp. 543-548 (2005).
Ho, Jennifer E. etl al., Biomarkers of Cardiovascular Stress and Incident Chronic Kidney Disease, Clinical Chemistry, vol. 59, No. 11, pp. 1613-1620 (2013).
Tokuriki, Nobuhiko et al., Stability effects of mutations and protein evolvability, Current Opinion in Structural Biology, vol. 19, pp. 596-604 (2009).
Alaoui-Ismaili, Moulay Hicham et al., Design of second generation therapeutic recombinant bone morphogenetic proteins, Cytokine & Growth Factor Reviews, vol. 20, pp. 501-507 (2009).
Bhattacharya, Roshni et al., Impact of genetic variation on three dimensional structure and function of protein, Plos One, vol. 12, No. 3, pp. 1-22 (2017).
Kempf, Tibor et al., The Transforming Growth Factor-B Superfamily Member Growth-Differentiation Factor-15 Protects the Heart from Ishemia/Reperfusion Injury, Circulation Research, vol. 98, pp. 351-360 (2006).
Guo, Haiwei et al., Protein tolerance to random amino acid change, PNAS, vol. 101, No. 25, pp. 9205-9210 (Jun. 22, 2004).

Figure 7

| | NK92 (IL2 culture) | PBMC culture | MCF-7 culture |
|---|---|---|---|
| GDF15 | +39x | | |
| PlGF | +74x | | |
| Trail-r2 | +17x | | |
| LAP-TGFb1 | +6x | | |
| Capase-3 | +6x (+5x TGFb3 10ng/ml) | | +478x |
| MIC-A | +10x | | +6x |
| HB-EGF | +7x | | +16x |
| TNF-R1 | | | +4x |
| FGF19 | | +8x (M1 2ug/ml) | |
| TNFRSF9 | | +11x | |
| CXCL9 | | +8x | |
| CXCL10 | | (-3x by TGBb3 10ng/ml) | |
| CXCL11 | | (-5x by TGFb3 10ng/ml) | |
| IFNgamma | | -4.5x (LPS stim.) (-1.6x by M1 0.5ug/ml) | |

SEQUENCE LISTING

<160> NUMBER OF SEQ ID NOS: 243

<210> SEQ ID NO 1
<211> LENGTH: 669
<212> TYPE: PRT
<213> ORGANISM: Homo sapiens -continued

```
<400> SEQUENCE: 1

Met Ala Ala Ala Gln Glu Ala Asp Gly Ala Arg Ser Ala Val Val Ala
1               5                   10                  15

Ala Gly Gly Gly Ser Ser Gly Gln Val Thr Ser Asn Gly Ser Ile Gly
            20                  25                  30

Arg Asp Pro Pro Ala Glu Thr Gln Pro Gln Asn Pro Pro Ala Gln Pro
        35                  40                  45

Ala Pro Asn Ala Trp Gln Val Ile Lys Gly Val Leu Phe Arg Ile Phe
    50                  55                  60

Ile Ile Trp Ala Ile Ser Ser Trp Phe Arg Arg Gly Pro Ala Pro Gln
65                  70                  75                  80

Asp Gln Ala Gly Pro Gly Ala Pro Arg Val Ala Ser Arg Asn Leu
                85                  90                  95

Phe Pro Lys Asp Thr Leu Met Asn Leu His Val Tyr Ile Ser Glu His
            100                 105                 110

Glu His Phe Thr Asp Phe Asn Ala Thr Ser Ala Leu Phe Trp Glu Gln
        115                 120                 125

His Asp Leu Val Tyr Gly Asp Trp Thr Ser Gly Glu Asn Ser Asp Gly
    130                 135                 140

Cys Tyr Glu His Phe Ala Glu Leu Asp Ile Pro Gln Ser Val Gln Gln
145                 150                 155                 160

Asn Gly Ser Ile Tyr Ile His Val Tyr Phe Thr Lys Ser Gly Phe His
                165                 170                 175

Pro Asp Pro Arg Gln Lys Ala Leu Tyr Arg Arg Leu Ala Thr Val His
            180                 185                 190

Met Ser Arg Met Ile Asn Lys Tyr Lys Arg Arg Phe Gln Lys Thr
        195                 200                 205

Lys Asn Leu Leu Thr Gly Glu Thr Glu Ala Asp Pro Glu Met Ile Lys
    210                 215                 220

Arg Ala Glu Asp Tyr Gly Pro Val Glu Val Ile Ser His Trp His Pro
225                 230                 235                 240

Asn Ile Thr Ile Asn Ile Val Asp Asp His Thr Pro Trp Val Lys Gly
                245                 250                 255

Ser Val Pro Pro Leu Asp Gln Tyr Val Lys Phe Asp Ala Val Ser
            260                 265                 270

Gly Asp Tyr Tyr Pro Ile Ile Tyr Phe Asn Asp Tyr Trp Asn Leu Gln
        275                 280                 285

Lys Asp Tyr Tyr Pro Ile Asn Glu Ser Leu Ala Ser Leu Pro Leu Arg
    290                 295                 300

Val Ser Phe Cys Pro Leu Ser Leu Trp Arg Trp Gln Leu Tyr Ala Ala
305                 310                 315                 320

Gln Ser Thr Lys Ser Pro Trp Asn Phe Leu Gly Asp Glu Leu Tyr Glu
                325                 330                 335

Gln Ser Asp Glu Glu Gln Asp Ser Val Lys Val Ala Leu Leu Glu Thr
            340                 345                 350

Asn Pro Tyr Leu Leu Ala Leu Thr Ile Ile Val Ser Ile Val His Ser
        355                 360                 365

Val Phe Glu Phe Leu Ala Phe Lys Asn Asp Ile Gln Phe Trp Asn Ser
    370                 375                 380

Arg Gln Ser Leu Glu Gly Leu Ser Val Arg Ser Val Phe Phe Gly Val
385                 390                 395                 400

Phe Gln Ser Phe Val Val Leu Leu Tyr Ile Leu Asp Asn Glu Thr Asn
                405                 410                 415
```

Phe Val Gln Val Ser Val Phe Ile Gly Val Leu Ile Asp Leu Trp
            420                 425                 430

Lys Ile Thr Lys Val Met Asp Val Arg Leu Asp Arg Glu His Arg Val
        435                 440                 445

Ala Gly Ile Phe Pro Arg Leu Ser Phe Lys Asp Lys Ser Thr Tyr Ile
450                 455                 460

Glu Ser Ser Thr Lys Val Tyr Asp Asp Met Ala Phe Arg Tyr Leu Ser
465                 470                 475                 480

Trp Ile Leu Phe Pro Leu Leu Gly Cys Tyr Ala Val Tyr Ser Leu Leu
                485                 490                 495

Tyr Leu Glu His Lys Gly Trp Tyr Ser Trp Val Leu Ser Met Leu Tyr
            500                 505                 510

Gly Phe Leu Leu Thr Phe Gly Phe Ile Thr Met Thr Pro Gln Leu Phe
        515                 520                 525

Ile Asn Tyr Lys Leu Lys Ser Val Ala His Leu Pro Trp Arg Met Leu
    530                 535                 540

Thr Tyr Lys Ala Leu Asn Thr Phe Ile Asp Asp Leu Phe Ala Phe Val
545                 550                 555                 560

Ile Lys Met Pro Val Met Tyr Arg Ile Gly Cys Leu Arg Asp Asp Val
                565                 570                 575

Val Phe Phe Ile Tyr Leu Tyr Gln Arg Trp Ile Tyr Arg Val Asp Pro
            580                 585                 590

Thr Arg Val Asn Glu Phe Gly Met Ser Gly Glu Asp Pro Thr Ala Ala
        595                 600                 605

Ala Pro Val Ala Glu Val Pro Thr Ala Ala Gly Ala Leu Thr Pro Thr
    610                 615                 620

Pro Ala Pro Thr Thr Thr Thr Ala Thr Arg Glu Glu Ala Ser Thr Ser
625                 630                 635                 640

Leu Pro Thr Lys Pro Thr Gln Gly Ala Ser Ser Ala Ser Glu Pro Gln
                645                 650                 655

Glu Ala Pro Pro Lys Pro Ala Glu Asp Lys Lys Lys Asp
            660                 665

<210> SEQ ID NO 2
<211> LENGTH: 353
<212> TYPE: PRT
<213> ORGANISM: Homo sapiens

<400> SEQUENCE: 2

Ala Ala Ala Gln Glu Ala Asp Gly Ala Arg Ser Ala Val Val Ala Ala
1               5                   10                  15

Gly Gly Gly Ser Ser Gly Gln Val Thr Ser Asn Gly Ser Ile Gly Arg
            20                  25                  30

Asp Pro Pro Ala Glu Thr Gln Pro Gln Asn Pro Pro Ala Gln Pro Ala
        35                  40                  45

Pro Asn Ala Trp Gln Val Ile Lys Gly Val Leu Phe Arg Ile Phe Ile
    50                  55                  60

Ile Trp Ala Ile Ser Ser Trp Phe Arg Arg Gly Pro Ala Pro Gln Asp
65                  70                  75                  80

Gln Ala Gly Pro Gly Gly Ala Pro Arg Val Ala Ser Arg Asn Leu Phe
                85                  90                  95

Pro Lys Asp Thr Leu Met Asn Leu His Val Tyr Ile Ser Glu His Glu
            100                 105                 110

His Phe Thr Asp Phe Asn Ala Thr Ser Ala Leu Phe Trp Glu Gln His

```
            115                 120                 125
Asp Leu Val Tyr Gly Asp Trp Thr Ser Gly Glu Asn Ser Asp Gly Cys
    130                 135                 140

Tyr Glu His Phe Ala Glu Leu Asp Ile Pro Gln Ser Val Gln Gln Asn
145                 150                 155                 160

Gly Ser Ile Tyr Ile His Val Tyr Phe Thr Lys Ser Gly Phe His Pro
                165                 170                 175

Asp Pro Arg Gln Lys Ala Leu Tyr Arg Arg Leu Ala Thr Val His Met
            180                 185                 190

Ser Arg Met Ile Asn Lys Tyr Lys Arg Arg Phe Gln Lys Thr Lys
        195                 200                 205

Asn Leu Leu Thr Gly Glu Thr Glu Ala Asp Pro Glu Met Ile Lys Arg
    210                 215                 220

Ala Glu Asp Tyr Gly Pro Val Glu Val Ile Ser His Trp His Pro Asn
225                 230                 235                 240

Ile Thr Ile Asn Ile Val Asp Asp His Thr Pro Trp Val Lys Gly Ser
                245                 250                 255

Val Pro Pro Pro Leu Asp Gln Tyr Val Lys Phe Asp Ala Val Ser Gly
            260                 265                 270

Asp Tyr Tyr Pro Ile Ile Tyr Phe Asn Asp Tyr Trp Asn Leu Gln Lys
        275                 280                 285

Asp Tyr Tyr Pro Ile Asn Glu Ser Leu Ala Ser Leu Pro Leu Arg Val
    290                 295                 300

Ser Phe Cys Pro Leu Ser Leu Trp Arg Trp Gln Leu Tyr Ala Ala Gln
305                 310                 315                 320

Ser Thr Lys Ser Pro Trp Asn Phe Leu Gly Asp Glu Leu Tyr Glu Gln
                325                 330                 335

Ser Asp Glu Glu Gln Asp Ser Val Lys Val Ala Leu Leu Glu Thr Asn
            340                 345                 350

Pro

<210> SEQ ID NO 3
<211> LENGTH: 7
<212> TYPE: PRT
<213> ORGANISM: Homo sapiens

<400> SEQUENCE: 3

Tyr Ile Ser Glu His Glu His
1               5

<210> SEQ ID NO 4
<211> LENGTH: 6
<212> TYPE: PRT
<213> ORGANISM: Homo sapiens

<400> SEQUENCE: 4

Leu Phe Trp Glu Gln His
1               5

<210> SEQ ID NO 5
<211> LENGTH: 31
<212> TYPE: PRT
<213> ORGANISM: Homo sapiens

<400> SEQUENCE: 5

Tyr Ile Ser Glu His Glu His Phe Thr Asp Phe Asn Ala Thr Ser Ala
1               5                   10                  15
```

```
Leu Phe Trp Glu Gln His Asp Leu Val Tyr Gly Asp Trp Thr Ser
        20                  25                  30

<210> SEQ ID NO 6
<211> LENGTH: 16
<212> TYPE: PRT
<213> ORGANISM: Homo sapiens

<400> SEQUENCE: 6

Ala Leu Phe Trp Glu Gln His Asp Leu Val Tyr Gly Asp Trp Thr Ser
1               5                   10                  15

<210> SEQ ID NO 7
<211> LENGTH: 17
<212> TYPE: PRT
<213> ORGANISM: Homo sapiens

<400> SEQUENCE: 7

Gly Ala Leu Phe Trp Glu Gln His Asp Leu Val Tyr Gly Asp Trp Thr
1               5                   10                  15

Ser

<210> SEQ ID NO 8
<211> LENGTH: 21
<212> TYPE: PRT
<213> ORGANISM: Homo sapiens

<400> SEQUENCE: 8

Ala Ala Ala Gln Glu Ala Asp Gly Ala Arg Ser Ala Val Val Ala Ala
1               5                   10                  15

Gly Gly Gly Ser Gly
            20

<210> SEQ ID NO 9
<211> LENGTH: 21
<212> TYPE: PRT
<213> ORGANISM: Homo sapiens

<400> SEQUENCE: 9

Ser Gly Gln Val Thr Ser Asn Gly Ser Ile Gly Arg Asp Pro Pro Ala
1               5                   10                  15

Glu Thr Gln Pro Gly
            20

<210> SEQ ID NO 10
<211> LENGTH: 21
<212> TYPE: PRT
<213> ORGANISM: Homo sapiens

<400> SEQUENCE: 10

Gln Asn Pro Pro Ala Gln Pro Ala Pro Asn Ala Trp Gln Val Ile Lys
1               5                   10                  15

Gly Val Leu Phe Gly
            20

<210> SEQ ID NO 11
<211> LENGTH: 21
<212> TYPE: PRT
<213> ORGANISM: Homo sapiens

<400> SEQUENCE: 11

Arg Ile Phe Ile Ile Trp Ala Ile Ser Ser Trp Phe Arg Arg Gly Pro
1               5                   10                  15
```

Ala Pro Gln Asp Gly
            20

<210> SEQ ID NO 12
<211> LENGTH: 21
<212> TYPE: PRT
<213> ORGANISM: Homo sapiens

<400> SEQUENCE: 12

Gln Ala Gly Pro Gly Gly Ala Pro Arg Val Ala Ser Arg Asn Leu Phe
1               5                   10                  15

Pro Lys Asp Thr Gly
            20

<210> SEQ ID NO 13
<211> LENGTH: 21
<212> TYPE: PRT
<213> ORGANISM: Homo sapiens

<400> SEQUENCE: 13

Leu Met Asn Leu His Val Tyr Ile Ser Glu His Glu His Phe Thr Asp
1               5                   10                  15

Phe Asn Ala Thr Gly
            20

<210> SEQ ID NO 14
<211> LENGTH: 21
<212> TYPE: PRT
<213> ORGANISM: Homo sapiens

<400> SEQUENCE: 14

Ser Ala Leu Phe Trp Glu Gln His Asp Leu Val Tyr Gly Asp Trp Thr
1               5                   10                  15

Ser Gly Glu Asn Gly
            20

<210> SEQ ID NO 15
<211> LENGTH: 21
<212> TYPE: PRT
<213> ORGANISM: Homo sapiens

<400> SEQUENCE: 15

Ser Asp Gly Cys Tyr Glu His Phe Ala Glu Leu Asp Ile Pro Gln Ser
1               5                   10                  15

Val Gln Gln Asn Gly
            20

<210> SEQ ID NO 16
<211> LENGTH: 21
<212> TYPE: PRT
<213> ORGANISM: Homo sapiens

<400> SEQUENCE: 16

Gly Ser Ile Tyr Ile His Val Tyr Phe Thr Lys Ser Gly Phe His Pro
1               5                   10                  15

Asp Pro Arg Gln Gly
            20

<210> SEQ ID NO 17
<211> LENGTH: 21
<212> TYPE: PRT
<213> ORGANISM: Homo sapiens

<400> SEQUENCE: 17

Lys Ala Leu Tyr Arg Arg Leu Ala Thr Val His Met Ser Arg Met Ile
1               5                   10                  15

Asn Lys Tyr Lys Gly
            20

<210> SEQ ID NO 18
<211> LENGTH: 21
<212> TYPE: PRT
<213> ORGANISM: Homo sapiens

<400> SEQUENCE: 18

Arg Arg Arg Phe Gln Lys Thr Lys Asn Leu Leu Thr Gly Glu Thr Glu
1               5                   10                  15

Ala Asp Pro Glu Gly
            20

<210> SEQ ID NO 19
<211> LENGTH: 21
<212> TYPE: PRT
<213> ORGANISM: Homo sapiens

<400> SEQUENCE: 19

Met Ile Lys Arg Ala Glu Asp Tyr Gly Pro Val Glu Val Ile Ser His
1               5                   10                  15

Trp His Pro Asn Gly
            20

<210> SEQ ID NO 20
<211> LENGTH: 21
<212> TYPE: PRT
<213> ORGANISM: Homo sapiens

<400> SEQUENCE: 20

Ile Thr Ile Asn Ile Val Asp Asp His Thr Pro Trp Val Lys Gly Ser
1               5                   10                  15

Val Pro Pro Pro Gly
            20

<210> SEQ ID NO 21
<211> LENGTH: 21
<212> TYPE: PRT
<213> ORGANISM: Homo sapiens

<400> SEQUENCE: 21

Leu Asp Gln Tyr Val Lys Phe Asp Ala Val Ser Gly Asp Tyr Tyr Pro
1               5                   10                  15

Ile Ile Tyr Phe Gly
            20

<210> SEQ ID NO 22
<211> LENGTH: 21
<212> TYPE: PRT
<213> ORGANISM: Homo sapiens

<400> SEQUENCE: 22

Asn Asp Tyr Trp Asn Leu Gln Lys Asp Tyr Tyr Pro Ile Asn Glu Ser
1               5                   10                  15

Leu Ala Ser Leu Gly
            20

```
<210> SEQ ID NO 23
<211> LENGTH: 21
<212> TYPE: PRT
<213> ORGANISM: Homo sapiens

<400> SEQUENCE: 23

Pro Leu Arg Val Ser Phe Cys Pro Leu Ser Leu Trp Arg Trp Gln Leu
1               5                   10                  15

Tyr Ala Ala Gln Gly
            20

<210> SEQ ID NO 24
<211> LENGTH: 21
<212> TYPE: PRT
<213> ORGANISM: Homo sapiens

<400> SEQUENCE: 24

Ser Thr Lys Ser Pro Trp Asn Phe Leu Gly Asp Glu Leu Tyr Glu Gln
1               5                   10                  15

Ser Asp Glu Glu Gly
            20

<210> SEQ ID NO 25
<211> LENGTH: 21
<212> TYPE: PRT
<213> ORGANISM: Homo sapiens

<400> SEQUENCE: 25

Tyr Glu Gln Ser Asp Glu Glu Gln Asp Ser Val Lys Val Ala Leu Leu
1               5                   10                  15

Glu Thr Asn Pro Gly
            20

<210> SEQ ID NO 26
<211> LENGTH: 21
<212> TYPE: PRT
<213> ORGANISM: Homo sapiens

<400> SEQUENCE: 26

Leu Trp Arg Trp Gln Leu Tyr Ala Ala Gln Ser Thr Lys Ser Pro Trp
1               5                   10                  15

Asn Phe Leu Gly Gly
            20

<210> SEQ ID NO 27
<211> LENGTH: 21
<212> TYPE: PRT
<213> ORGANISM: Homo sapiens

<400> SEQUENCE: 27

Tyr Pro Ile Asn Glu Ser Leu Ala Ser Leu Pro Leu Arg Val Ser Phe
1               5                   10                  15

Cys Pro Leu Ser Gly
            20

<210> SEQ ID NO 28
<211> LENGTH: 21
<212> TYPE: PRT
<213> ORGANISM: Homo sapiens

<400> SEQUENCE: 28

Gly Asp Tyr Tyr Pro Ile Ile Tyr Phe Asn Asp Tyr Trp Asn Leu Gln
```

```
1               5                   10                  15
Lys Asp Tyr Tyr Gly
            20

<210> SEQ ID NO 29
<211> LENGTH: 21
<212> TYPE: PRT
<213> ORGANISM: Homo sapiens

<400> SEQUENCE: 29

Trp Gln Val Ile Lys Gly Val Leu Phe Arg Ile Phe Ile Ile Trp Ala
1               5                   10                  15

Ile Ser Ser Trp Gly
            20

<210> SEQ ID NO 30
<211> LENGTH: 21
<212> TYPE: PRT
<213> ORGANISM: Homo sapiens

<400> SEQUENCE: 30

Arg Asn Leu Phe Pro Lys Asp Thr Leu Met Asn Leu His Val Tyr Ile
1               5                   10                  15

Ser Glu His Glu Gly
            20

<210> SEQ ID NO 31
<211> LENGTH: 21
<212> TYPE: PRT
<213> ORGANISM: Homo sapiens

<400> SEQUENCE: 31

Phe Thr Asp Phe Asn Ala Thr Ser Ala Leu Phe Trp Glu Gln His Asp
1               5                   10                  15

Leu Val Tyr Gly Gly
            20

<210> SEQ ID NO 32
<211> LENGTH: 40
<212> TYPE: PRT
<213> ORGANISM: Homo sapiens

<400> SEQUENCE: 32

Ser Gly Asp Tyr Tyr Pro Ile Ile Tyr Phe Asn Asp Tyr Trp Asn Leu
1               5                   10                  15

Gln Lys Asp Tyr Tyr Pro Ile Asn Glu Ser Leu Ala Ser Leu Pro Leu
            20                  25                  30

Arg Val Ser Phe Cys Pro Leu Ser
        35                  40

<210> SEQ ID NO 33
<211> LENGTH: 43
<212> TYPE: PRT
<213> ORGANISM: Homo sapiens

<400> SEQUENCE: 33

Leu Trp Arg Trp Gln Leu Tyr Ala Ala Gln Ser Thr Lys Ser Pro Trp
1               5                   10                  15

Asn Phe Leu Gly Asp Glu Leu Tyr Glu Gln Ser Asp Glu Gln Asp
            20                  25                  30

Ser Val Lys Val Ala Leu Leu Glu Thr Asn Pro
```

<210> SEQ ID NO 34
<211> LENGTH: 40
<212> TYPE: PRT
<213> ORGANISM: Homo sapiens

<400> SEQUENCE: 34

Ala Arg Ser Ala Val Val Ala Ala Gly Gly Ser Ser Gly Gln Val
1               5                   10                  15

Thr Ser Asn Gly Ser Ile Gly Arg Asp Pro Pro Ala Glu Thr Gln Pro
                20                  25                  30

Gln Asn Pro Pro Ala Gln Pro Ala
                35                  40

<210> SEQ ID NO 35
<211> LENGTH: 38
<212> TYPE: PRT
<213> ORGANISM: Homo sapiens

<400> SEQUENCE: 35

Asn Ala Trp Gln Val Ile Lys Gly Val Leu Phe Arg Ile Phe Ile Ile
1               5                   10                  15

Trp Ala Ile Ser Ser Trp Phe Arg Arg Gly Pro Ala Pro Gln Asp Gln
                20                  25                  30

Ala Gly Pro Gly Gly Ala
                35

<210> SEQ ID NO 36
<211> LENGTH: 40
<212> TYPE: PRT
<213> ORGANISM: Homo sapiens

<400> SEQUENCE: 36

Asp Thr Leu Met Asn Leu His Val Tyr Ile Ser Glu His Glu His Phe
1               5                   10                  15

Thr Asp Phe Asn Ala Thr Ser Ala Leu Phe Trp Glu Gln His Asp Leu
                20                  25                  30

Val Tyr Gly Asp Trp Thr Ser Gly
                35                  40

<210> SEQ ID NO 37
<211> LENGTH: 40
<212> TYPE: PRT
<213> ORGANISM: Homo sapiens

<400> SEQUENCE: 37

Thr Lys Ser Gly Phe His Pro Asp Pro Arg Gln Lys Ala Leu Tyr Arg
1               5                   10                  15

Arg Leu Ala Thr Val His Met Ser Arg Met Ile Asn Lys Tyr Lys Arg
                20                  25                  30

Arg Arg Phe Gln Lys Thr Lys Asn
                35                  40

<210> SEQ ID NO 38
<211> LENGTH: 38
<212> TYPE: PRT
<213> ORGANISM: Homo sapiens

<400> SEQUENCE: 38

Val Ser Gly Asp Tyr Tyr Pro Ile Ile Tyr Phe Asn Asp Tyr Trp Asn

```
                1               5                   10                  15
            Leu Gln Lys Asp Tyr Tyr Pro Ile Asn Glu Ser Leu Ala Ser Leu Pro
                            20                  25                  30

Leu Arg Val Ser Phe Cys
                        35

<210> SEQ ID NO 39
<211> LENGTH: 39
<212> TYPE: PRT
<213> ORGANISM: Homo sapiens

<400> SEQUENCE: 39

Pro Leu Asp Gln Tyr Val Lys Phe Asp Ala Val Ser Gly Asp Tyr Tyr
1               5                   10                  15

Pro Ile Ile Tyr Phe Asn Asp Tyr Trp Asn Leu Gln Lys Asp Tyr Tyr
            20                  25                  30

Pro Ile Asn Glu Ser Leu Ala
        35

<210> SEQ ID NO 40
<211> LENGTH: 28
<212> TYPE: PRT
<213> ORGANISM: Homo sapiens

<400> SEQUENCE: 40

Ser Gly Asp Tyr Tyr Pro Ile Ile Tyr Phe Asn Asp Tyr Trp Asn Leu
1               5                   10                  15

Gln Lys Asp Tyr Tyr Pro Ile Asn Glu Ser Leu Ala
            20                  25

<210> SEQ ID NO 41
<211> LENGTH: 5
<212> TYPE: PRT
<213> ORGANISM: Homo sapiens

<400> SEQUENCE: 41

Asp Tyr Pro Pro Ile
1               5

<210> SEQ ID NO 42
<211> LENGTH: 20
<212> TYPE: PRT
<213> ORGANISM: Homo sapiens

<400> SEQUENCE: 42

Gly Asp Tyr Tyr Pro Ile Ile Tyr Phe Asn Asp Tyr Trp Asn Leu Gln
1               5                   10                  15

Lys Asp Tyr Tyr
            20

<210> SEQ ID NO 43
<211> LENGTH: 30
<212> TYPE: PRT
<213> ORGANISM: Homo sapiens

<400> SEQUENCE: 43

Tyr Ile Ser Glu His Glu His Phe Thr Asp Phe Asn Ala Thr Ser Ala
1               5                   10                  15

Leu Phe Trp Glu Gln His Asp Leu Val Tyr Gly Asp Trp Thr
            20                  25                  30
```

```
<210> SEQ ID NO 44
<211> LENGTH: 29
<212> TYPE: PRT
<213> ORGANISM: Homo sapiens

<400> SEQUENCE: 44

Tyr Ile Ser Glu His Glu His Phe Thr Asp Phe Asn Ala Thr Ser Ala
1               5                   10                  15

Leu Phe Trp Glu Gln His Asp Leu Val Tyr Gly Asp Trp
            20                  25

<210> SEQ ID NO 45
<211> LENGTH: 28
<212> TYPE: PRT
<213> ORGANISM: Homo sapiens

<400> SEQUENCE: 45

Tyr Ile Ser Glu His Glu His Phe Thr Asp Phe Asn Ala Thr Ser Ala
1               5                   10                  15

Leu Phe Trp Glu Gln His Asp Leu Val Tyr Gly Asp
            20                  25

<210> SEQ ID NO 46
<211> LENGTH: 27
<212> TYPE: PRT
<213> ORGANISM: Homo sapiens

<400> SEQUENCE: 46

Tyr Ile Ser Glu His Glu His Phe Thr Asp Phe Asn Ala Thr Ser Ala
1               5                   10                  15

Leu Phe Trp Glu Gln His Asp Leu Val Tyr Gly
            20                  25

<210> SEQ ID NO 47
<211> LENGTH: 26
<212> TYPE: PRT
<213> ORGANISM: Homo sapiens

<400> SEQUENCE: 47

Tyr Ile Ser Glu His Glu His Phe Thr Asp Phe Asn Ala Thr Ser Ala
1               5                   10                  15

Leu Phe Trp Glu Gln His Asp Leu Val Tyr
            20                  25

<210> SEQ ID NO 48
<211> LENGTH: 25
<212> TYPE: PRT
<213> ORGANISM: Homo sapiens

<400> SEQUENCE: 48

Tyr Ile Ser Glu His Glu His Phe Thr Asp Phe Asn Ala Thr Ser Ala
1               5                   10                  15

Leu Phe Trp Glu Gln His Asp Leu Val
            20                  25

<210> SEQ ID NO 49
<211> LENGTH: 24
<212> TYPE: PRT
<213> ORGANISM: Homo sapiens

<400> SEQUENCE: 49

Tyr Ile Ser Glu His Glu His Phe Thr Asp Phe Asn Ala Thr Ser Ala
1               5                   10                  15
```

```
Leu Phe Trp Glu Gln His Asp Leu
        20

<210> SEQ ID NO 50
<211> LENGTH: 23
<212> TYPE: PRT
<213> ORGANISM: Homo sapiens

<400> SEQUENCE: 50

Tyr Ile Ser Glu His Glu His Phe Thr Asp Phe Asn Ala Thr Ser Ala
1               5                   10                  15

Leu Phe Trp Glu Gln His Asp
        20

<210> SEQ ID NO 51
<211> LENGTH: 22
<212> TYPE: PRT
<213> ORGANISM: Homo sapiens

<400> SEQUENCE: 51

Tyr Ile Ser Glu His Glu His Phe Thr Asp Phe Asn Ala Thr Ser Ala
1               5                   10                  15

Leu Phe Trp Glu Gln His
        20

<210> SEQ ID NO 52
<211> LENGTH: 21
<212> TYPE: PRT
<213> ORGANISM: Homo sapiens

<400> SEQUENCE: 52

Tyr Ile Ser Glu His Glu His Phe Thr Asp Phe Asn Ala Thr Ser Ala
1               5                   10                  15

Leu Phe Trp Glu Gln
        20

<210> SEQ ID NO 53
<211> LENGTH: 20
<212> TYPE: PRT
<213> ORGANISM: Homo sapiens

<400> SEQUENCE: 53

Tyr Ile Ser Glu His Glu His Phe Thr Asp Phe Asn Ala Thr Ser Ala
1               5                   10                  15

Leu Phe Trp Glu
        20

<210> SEQ ID NO 54
<211> LENGTH: 19
<212> TYPE: PRT
<213> ORGANISM: Homo sapiens

<400> SEQUENCE: 54

Tyr Ile Ser Glu His Glu His Phe Thr Asp Phe Asn Ala Thr Ser Ala
1               5                   10                  15

Leu Phe Trp

<210> SEQ ID NO 55
<211> LENGTH: 18
<212> TYPE: PRT
<213> ORGANISM: Homo sapiens
```

<400> SEQUENCE: 55

Tyr Ile Ser Glu His Glu His Phe Thr Asp Phe Asn Ala Thr Ser Ala
1               5                   10                  15

Leu Phe

<210> SEQ ID NO 56
<211> LENGTH: 17
<212> TYPE: PRT
<213> ORGANISM: Homo sapiens

<400> SEQUENCE: 56

Tyr Ile Ser Glu His Glu His Phe Thr Asp Phe Asn Ala Thr Ser Ala
1               5                   10                  15

Leu

<210> SEQ ID NO 57
<211> LENGTH: 16
<212> TYPE: PRT
<213> ORGANISM: Homo sapiens

<400> SEQUENCE: 57

Tyr Ile Ser Glu His Glu His Phe Thr Asp Phe Asn Ala Thr Ser Ala
1               5                   10                  15

<210> SEQ ID NO 58
<211> LENGTH: 15
<212> TYPE: PRT
<213> ORGANISM: Homo sapiens

<400> SEQUENCE: 58

Tyr Ile Ser Glu His Glu His Phe Thr Asp Phe Asn Ala Thr Ser
1               5                   10                  15

<210> SEQ ID NO 59
<211> LENGTH: 14
<212> TYPE: PRT
<213> ORGANISM: Homo sapiens

<400> SEQUENCE: 59

Tyr Ile Ser Glu His Glu His Phe Thr Asp Phe Asn Ala Thr
1               5                   10

<210> SEQ ID NO 60
<211> LENGTH: 13
<212> TYPE: PRT
<213> ORGANISM: Homo sapiens

<400> SEQUENCE: 60

Tyr Ile Ser Glu His Glu His Phe Thr Asp Phe Asn Ala
1               5                   10

<210> SEQ ID NO 61
<211> LENGTH: 12
<212> TYPE: PRT
<213> ORGANISM: Homo sapiens

<400> SEQUENCE: 61

Tyr Ile Ser Glu His Glu His Phe Thr Asp Phe Asn
1               5                   10

<210> SEQ ID NO 62
<211> LENGTH: 11
<212> TYPE: PRT

```
<213> ORGANISM: Homo sapiens

<400> SEQUENCE: 62

Tyr Ile Ser Glu His Glu His Phe Thr Asp Phe
1               5                   10

<210> SEQ ID NO 63
<211> LENGTH: 10
<212> TYPE: PRT
<213> ORGANISM: Homo sapiens

<400> SEQUENCE: 63

Tyr Ile Ser Glu His Glu His Phe Thr Asp
1               5                   10

<210> SEQ ID NO 64
<211> LENGTH: 9
<212> TYPE: PRT
<213> ORGANISM: Homo sapiens

<400> SEQUENCE: 64

Tyr Ile Ser Glu His Glu His Phe Thr
1               5

<210> SEQ ID NO 65
<211> LENGTH: 8
<212> TYPE: PRT
<213> ORGANISM: Homo sapiens

<400> SEQUENCE: 65

Tyr Ile Ser Glu His Glu His Phe
1               5

<210> SEQ ID NO 66
<211> LENGTH: 30
<212> TYPE: PRT
<213> ORGANISM: Homo sapiens

<400> SEQUENCE: 66

Ile Ser Glu His Glu His Phe Thr Asp Phe Asn Ala Thr Ser Ala Leu
1               5                   10                  15

Phe Trp Glu Gln His Asp Leu Val Tyr Gly Asp Trp Thr Ser
            20                  25                  30

<210> SEQ ID NO 67
<211> LENGTH: 29
<212> TYPE: PRT
<213> ORGANISM: Homo sapiens

<400> SEQUENCE: 67

Ser Glu His Glu His Phe Thr Asp Phe Asn Ala Thr Ser Ala Leu Phe
1               5                   10                  15

Trp Glu Gln His Asp Leu Val Tyr Gly Asp Trp Thr Ser
            20                  25

<210> SEQ ID NO 68
<211> LENGTH: 28
<212> TYPE: PRT
<213> ORGANISM: Homo sapiens

<400> SEQUENCE: 68

Glu His Glu His Phe Thr Asp Phe Asn Ala Thr Ser Ala Leu Phe Trp
1               5                   10                  15
```

Glu Gln His Asp Leu Val Tyr Gly Asp Trp Thr Ser
        20                  25

<210> SEQ ID NO 69
<211> LENGTH: 27
<212> TYPE: PRT
<213> ORGANISM: Homo sapiens

<400> SEQUENCE: 69

His Glu His Phe Thr Asp Phe Asn Ala Thr Ser Ala Leu Phe Trp Glu
1               5                   10                  15

Gln His Asp Leu Val Tyr Gly Asp Trp Thr Ser
            20                  25

<210> SEQ ID NO 70
<211> LENGTH: 26
<212> TYPE: PRT
<213> ORGANISM: Homo sapiens

<400> SEQUENCE: 70

Glu His Phe Thr Asp Phe Asn Ala Thr Ser Ala Leu Phe Trp Glu Gln
1               5                   10                  15

His Asp Leu Val Tyr Gly Asp Trp Thr Ser
        20                  25

<210> SEQ ID NO 71
<211> LENGTH: 25
<212> TYPE: PRT
<213> ORGANISM: Homo sapiens

<400> SEQUENCE: 71

His Phe Thr Asp Phe Asn Ala Thr Ser Ala Leu Phe Trp Glu Gln His
1               5                   10                  15

Asp Leu Val Tyr Gly Asp Trp Thr Ser
            20                  25

<210> SEQ ID NO 72
<211> LENGTH: 24
<212> TYPE: PRT
<213> ORGANISM: Homo sapiens

<400> SEQUENCE: 72

Phe Thr Asp Phe Asn Ala Thr Ser Ala Leu Phe Trp Glu Gln His Asp
1               5                   10                  15

Leu Val Tyr Gly Asp Trp Thr Ser
            20

<210> SEQ ID NO 73
<211> LENGTH: 23
<212> TYPE: PRT
<213> ORGANISM: Homo sapiens

<400> SEQUENCE: 73

Thr Asp Phe Asn Ala Thr Ser Ala Leu Phe Trp Glu Gln His Asp Leu
1               5                   10                  15

Val Tyr Gly Asp Trp Thr Ser
            20

<210> SEQ ID NO 74
<211> LENGTH: 22
<212> TYPE: PRT
<213> ORGANISM: Homo sapiens

```
<400> SEQUENCE: 74

Asp Phe Asn Ala Thr Ser Ala Leu Phe Trp Glu Gln His Asp Leu Val
1               5                   10                  15

Tyr Gly Asp Trp Thr Ser
            20

<210> SEQ ID NO 75
<211> LENGTH: 21
<212> TYPE: PRT
<213> ORGANISM: Homo sapiens

<400> SEQUENCE: 75

Phe Asn Ala Thr Ser Ala Leu Phe Trp Glu Gln His Asp Leu Val Tyr
1               5                   10                  15

Gly Asp Trp Thr Ser
            20

<210> SEQ ID NO 76
<211> LENGTH: 20
<212> TYPE: PRT
<213> ORGANISM: Homo sapiens

<400> SEQUENCE: 76

Asn Ala Thr Ser Ala Leu Phe Trp Glu Gln His Asp Leu Val Tyr Gly
1               5                   10                  15

Asp Trp Thr Ser
            20

<210> SEQ ID NO 77
<211> LENGTH: 19
<212> TYPE: PRT
<213> ORGANISM: Homo sapiens

<400> SEQUENCE: 77

Ala Thr Ser Ala Leu Phe Trp Glu Gln His Asp Leu Val Tyr Gly Asp
1               5                   10                  15

Trp Thr Ser

<210> SEQ ID NO 78
<211> LENGTH: 18
<212> TYPE: PRT
<213> ORGANISM: Homo sapiens

<400> SEQUENCE: 78

Thr Ser Ala Leu Phe Trp Glu Gln His Asp Leu Val Tyr Gly Asp Trp
1               5                   10                  15

Thr Ser

<210> SEQ ID NO 79
<211> LENGTH: 17
<212> TYPE: PRT
<213> ORGANISM: Homo sapiens

<400> SEQUENCE: 79

Ser Ala Leu Phe Trp Glu Gln His Asp Leu Val Tyr Gly Asp Trp Thr
1               5                   10                  15

Ser

<210> SEQ ID NO 80
<211> LENGTH: 16
<212> TYPE: PRT
```

<213> ORGANISM: Homo sapiens

<400> SEQUENCE: 80

Ala Leu Phe Trp Glu Gln His Asp Leu Val Tyr Gly Asp Trp Thr Ser
1               5                   10                  15

<210> SEQ ID NO 81
<211> LENGTH: 15
<212> TYPE: PRT
<213> ORGANISM: Homo sapiens

<400> SEQUENCE: 81

Leu Phe Trp Glu Gln His Asp Leu Val Tyr Gly Asp Trp Thr Ser
1               5                   10                  15

<210> SEQ ID NO 82
<211> LENGTH: 14
<212> TYPE: PRT
<213> ORGANISM: Homo sapiens

<400> SEQUENCE: 82

Leu Phe Trp Glu Gln His Asp Leu Val Tyr Gly Asp Trp Thr
1               5                   10

<210> SEQ ID NO 83
<211> LENGTH: 13
<212> TYPE: PRT
<213> ORGANISM: Homo sapiens

<400> SEQUENCE: 83

Leu Phe Trp Glu Gln His Asp Leu Val Tyr Gly Asp Trp
1               5                   10

<210> SEQ ID NO 84
<211> LENGTH: 12
<212> TYPE: PRT
<213> ORGANISM: Homo sapiens

<400> SEQUENCE: 84

Leu Phe Trp Glu Gln His Asp Leu Val Tyr Gly Asp
1               5                   10

<210> SEQ ID NO 85
<211> LENGTH: 11
<212> TYPE: PRT
<213> ORGANISM: Homo sapiens

<400> SEQUENCE: 85

Leu Phe Trp Glu Gln His Asp Leu Val Tyr Gly
1               5                   10

<210> SEQ ID NO 86
<211> LENGTH: 10
<212> TYPE: PRT
<213> ORGANISM: Homo sapiens

<400> SEQUENCE: 86

Leu Phe Trp Glu Gln His Asp Leu Val Tyr
1               5                   10

<210> SEQ ID NO 87
<211> LENGTH: 9
<212> TYPE: PRT
<213> ORGANISM: Homo sapiens

```
<400> SEQUENCE: 87

Leu Phe Trp Glu Gln His Asp Leu Val
1               5

<210> SEQ ID NO 88
<211> LENGTH: 8
<212> TYPE: PRT
<213> ORGANISM: Homo sapiens

<400> SEQUENCE: 88

Leu Phe Trp Glu Gln His Asp Leu
1               5

<210> SEQ ID NO 89
<211> LENGTH: 7
<212> TYPE: PRT
<213> ORGANISM: Homo sapiens

<400> SEQUENCE: 89

Leu Phe Trp Glu Gln His Asp
1               5

<210> SEQ ID NO 90
<211> LENGTH: 15
<212> TYPE: PRT
<213> ORGANISM: Homo sapiens

<400> SEQUENCE: 90

Phe Thr Asp Phe Asn Ala Thr Ser Ala Leu Phe Trp Glu Gln His
1               5                   10                  15

<210> SEQ ID NO 91
<211> LENGTH: 15
<212> TYPE: PRT
<213> ORGANISM: Homo sapiens

<400> SEQUENCE: 91

Thr Asp Phe Asn Ala Thr Ser Ala Leu Phe Trp Glu Gln His Asp
1               5                   10                  15

<210> SEQ ID NO 92
<211> LENGTH: 15
<212> TYPE: PRT
<213> ORGANISM: Homo sapiens

<400> SEQUENCE: 92

Asp Phe Asn Ala Thr Ser Ala Leu Phe Trp Glu Gln His Asp Leu
1               5                   10                  15

<210> SEQ ID NO 93
<211> LENGTH: 15
<212> TYPE: PRT
<213> ORGANISM: Homo sapiens

<400> SEQUENCE: 93

Phe Asn Ala Thr Ser Ala Leu Phe Trp Glu Gln His Asp Leu Val
1               5                   10                  15

<210> SEQ ID NO 94
<211> LENGTH: 15
<212> TYPE: PRT
<213> ORGANISM: Homo sapiens

<400> SEQUENCE: 94
```

Asn Ala Thr Ser Ala Leu Phe Trp Glu Gln His Asp Leu Val Tyr
1               5                   10                  15

<210> SEQ ID NO 95
<211> LENGTH: 15
<212> TYPE: PRT
<213> ORGANISM: Homo sapiens

<400> SEQUENCE: 95

Ala Thr Ser Ala Leu Phe Trp Glu Gln His Asp Leu Val Tyr Gly
1               5                   10                  15

<210> SEQ ID NO 96
<211> LENGTH: 15
<212> TYPE: PRT
<213> ORGANISM: Homo sapiens

<400> SEQUENCE: 96

Thr Ser Ala Leu Phe Trp Glu Gln His Asp Leu Val Tyr Gly Asp
1               5                   10                  15

<210> SEQ ID NO 97
<211> LENGTH: 15
<212> TYPE: PRT
<213> ORGANISM: Homo sapiens

<400> SEQUENCE: 97

Ser Ala Leu Phe Trp Glu Gln His Asp Leu Val Tyr Gly Asp Trp
1               5                   10                  15

<210> SEQ ID NO 98
<211> LENGTH: 15
<212> TYPE: PRT
<213> ORGANISM: Homo sapiens

<400> SEQUENCE: 98

Ala Leu Phe Trp Glu Gln His Asp Leu Val Tyr Gly Asp Trp Thr
1               5                   10                  15

<210> SEQ ID NO 99
<211> LENGTH: 21
<212> TYPE: PRT
<213> ORGANISM: Homo sapiens

<400> SEQUENCE: 99

Ile Ser Glu His Glu His Phe Thr Asp Phe Asn Ala Thr Ser Ala Leu
1               5                   10                  15

Phe Trp Glu Gln His
            20

<210> SEQ ID NO 100
<211> LENGTH: 20
<212> TYPE: PRT
<213> ORGANISM: Homo sapiens

<400> SEQUENCE: 100

Ser Glu His Glu His Phe Thr Asp Phe Asn Ala Thr Ser Ala Leu Phe
1               5                   10                  15

Trp Glu Gln His
            20

<210> SEQ ID NO 101
<211> LENGTH: 19
<212> TYPE: PRT

-continued

<213> ORGANISM: Homo sapiens

<400> SEQUENCE: 101

Glu His Glu His Phe Thr Asp Phe Asn Ala Thr Ser Ala Leu Phe Trp
1               5                   10                  15
Glu Gln His

<210> SEQ ID NO 102
<211> LENGTH: 18
<212> TYPE: PRT
<213> ORGANISM: Homo sapiens

<400> SEQUENCE: 102

His Glu His Phe Thr Asp Phe Asn Ala Thr Ser Ala Leu Phe Trp Glu
1               5                   10                  15
Gln His

<210> SEQ ID NO 103
<211> LENGTH: 17
<212> TYPE: PRT
<213> ORGANISM: Homo sapiens

<400> SEQUENCE: 103

Glu His Phe Thr Asp Phe Asn Ala Thr Ser Ala Leu Phe Trp Glu Gln
1               5                   10                  15
His

<210> SEQ ID NO 104
<211> LENGTH: 16
<212> TYPE: PRT
<213> ORGANISM: Homo sapiens

<400> SEQUENCE: 104

His Phe Thr Asp Phe Asn Ala Thr Ser Ala Leu Phe Trp Glu Gln His
1               5                   10                  15

<210> SEQ ID NO 105
<211> LENGTH: 15
<212> TYPE: PRT
<213> ORGANISM: Homo sapiens

<400> SEQUENCE: 105

Phe Thr Asp Phe Asn Ala Thr Ser Ala Leu Phe Trp Glu Gln His
1               5                   10                  15

<210> SEQ ID NO 106
<211> LENGTH: 14
<212> TYPE: PRT
<213> ORGANISM: Homo sapiens

<400> SEQUENCE: 106

Thr Asp Phe Asn Ala Thr Ser Ala Leu Phe Trp Glu Gln His
1               5                   10

<210> SEQ ID NO 107
<211> LENGTH: 13
<212> TYPE: PRT
<213> ORGANISM: Homo sapiens

<400> SEQUENCE: 107

Asp Phe Asn Ala Thr Ser Ala Leu Phe Trp Glu Gln His
1               5                   10

```
<210> SEQ ID NO 108
<211> LENGTH: 12
<212> TYPE: PRT
<213> ORGANISM: Homo sapiens

<400> SEQUENCE: 108

Phe Asn Ala Thr Ser Ala Leu Phe Trp Glu Gln His
1               5                   10

<210> SEQ ID NO 109
<211> LENGTH: 11
<212> TYPE: PRT
<213> ORGANISM: Homo sapiens

<400> SEQUENCE: 109

Asn Ala Thr Ser Ala Leu Phe Trp Glu Gln His
1               5                   10

<210> SEQ ID NO 110
<211> LENGTH: 10
<212> TYPE: PRT
<213> ORGANISM: Homo sapiens

<400> SEQUENCE: 110

Ala Thr Ser Ala Leu Phe Trp Glu Gln His
1               5                   10

<210> SEQ ID NO 111
<211> LENGTH: 8
<212> TYPE: PRT
<213> ORGANISM: Homo sapiens

<400> SEQUENCE: 111

Ser Ala Leu Phe Trp Glu Gln His
1               5

<210> SEQ ID NO 112
<211> LENGTH: 7
<212> TYPE: PRT
<213> ORGANISM: Homo sapiens

<400> SEQUENCE: 112

Ala Leu Phe Trp Glu Gln His
1               5

<210> SEQ ID NO 113
<211> LENGTH: 22
<212> TYPE: PRT
<213> ORGANISM: Homo sapiens

<400> SEQUENCE: 113

Ile Ser Glu His Glu His Phe Thr Asp Phe Asn Ala Thr Ser Ala Leu
1               5                   10                  15

Phe Trp Glu Gln His Asp
            20

<210> SEQ ID NO 114
<211> LENGTH: 22
<212> TYPE: PRT
<213> ORGANISM: Homo sapiens

<400> SEQUENCE: 114

Ser Glu His Glu His Phe Thr Asp Phe Asn Ala Thr Ser Ala Leu Phe
1               5                   10                  15
```

Trp Glu Gln His Asp Leu
            20

<210> SEQ ID NO 115
<211> LENGTH: 22
<212> TYPE: PRT
<213> ORGANISM: Homo sapiens

<400> SEQUENCE: 115

Glu His Glu His Phe Thr Asp Phe Asn Ala Thr Ser Ala Leu Phe Trp
1               5                   10                  15

Glu Gln His Asp Leu Val
            20

<210> SEQ ID NO 116
<211> LENGTH: 22
<212> TYPE: PRT
<213> ORGANISM: Homo sapiens

<400> SEQUENCE: 116

His Glu His Phe Thr Asp Phe Asn Ala Thr Ser Ala Leu Phe Trp Glu
1               5                   10                  15

Gln His Asp Leu Val Tyr
            20

<210> SEQ ID NO 117
<211> LENGTH: 22
<212> TYPE: PRT
<213> ORGANISM: Homo sapiens

<400> SEQUENCE: 117

Glu His Phe Thr Asp Phe Asn Ala Thr Ser Ala Leu Phe Trp Glu Gln
1               5                   10                  15

His Asp Leu Val Tyr Gly
            20

<210> SEQ ID NO 118
<211> LENGTH: 22
<212> TYPE: PRT
<213> ORGANISM: Homo sapiens

<400> SEQUENCE: 118

His Phe Thr Asp Phe Asn Ala Thr Ser Ala Leu Phe Trp Glu Gln His
1               5                   10                  15

Asp Leu Val Tyr Gly Asp
            20

<210> SEQ ID NO 119
<211> LENGTH: 22
<212> TYPE: PRT
<213> ORGANISM: Homo sapiens

<400> SEQUENCE: 119

Phe Thr Asp Phe Asn Ala Thr Ser Ala Leu Phe Trp Glu Gln His Asp
1               5                   10                  15

Leu Val Tyr Gly Asp Trp
            20

<210> SEQ ID NO 120
<211> LENGTH: 22
<212> TYPE: PRT
<213> ORGANISM: Homo sapiens

<400> SEQUENCE: 120

Thr Asp Phe Asn Ala Thr Ser Ala Leu Phe Trp Glu Gln His Asp Leu
1               5                   10                  15

Val Tyr Gly Asp Trp Thr
            20

<210> SEQ ID NO 121
<211> LENGTH: 22
<212> TYPE: PRT
<213> ORGANISM: Homo sapiens

<400> SEQUENCE: 121

Asp Phe Asn Ala Thr Ser Ala Leu Phe Trp Glu Gln His Asp Leu Val
1               5                   10                  15

Tyr Gly Asp Trp Thr Ser
            20

<210> SEQ ID NO 122
<211> LENGTH: 15
<212> TYPE: PRT
<213> ORGANISM: Homo sapiens

<400> SEQUENCE: 122

Ser Ala Leu Phe Trp Glu Gln His Asp Leu Val Tyr Gly Asp Trp
1               5                   10                  15

<210> SEQ ID NO 123
<211> LENGTH: 15
<212> TYPE: PRT
<213> ORGANISM: Homo sapiens

<400> SEQUENCE: 123

Thr Ser Ala Leu Phe Trp Glu Gln His Asp Leu Val Tyr Gly Asp
1               5                   10                  15

<210> SEQ ID NO 124
<211> LENGTH: 15
<212> TYPE: PRT
<213> ORGANISM: Homo sapiens

<400> SEQUENCE: 124

Ala Thr Ser Ala Leu Phe Trp Glu Gln His Asp Leu Val Tyr Gly
1               5                   10                  15

<210> SEQ ID NO 125
<211> LENGTH: 15
<212> TYPE: PRT
<213> ORGANISM: Homo sapiens

<400> SEQUENCE: 125

Asn Ala Thr Ser Ala Leu Phe Trp Glu Gln His Asp Leu Val Tyr
1               5                   10                  15

<210> SEQ ID NO 126
<211> LENGTH: 15
<212> TYPE: PRT
<213> ORGANISM: Homo sapiens

<400> SEQUENCE: 126

Phe Asn Ala Thr Ser Ala Leu Phe Trp Glu Gln His Asp Leu Val
1               5                   10                  15

-continued

```
<210> SEQ ID NO 127
<211> LENGTH: 15
<212> TYPE: PRT
<213> ORGANISM: Homo sapiens

<400> SEQUENCE: 127

Asp Phe Asn Ala Thr Ser Ala Leu Phe Trp Glu Gln His Asp Leu
1               5                   10                  15

<210> SEQ ID NO 128
<211> LENGTH: 15
<212> TYPE: PRT
<213> ORGANISM: Homo sapiens

<400> SEQUENCE: 128

Thr Asp Phe Asn Ala Thr Ser Ala Leu Phe Trp Glu Gln His Asp
1               5                   10                  15

<210> SEQ ID NO 129
<211> LENGTH: 15
<212> TYPE: PRT
<213> ORGANISM: Homo sapiens

<400> SEQUENCE: 129

Phe Thr Asp Phe Asn Ala Thr Ser Ala Leu Phe Trp Glu Gln His
1               5                   10                  15

<210> SEQ ID NO 130
<211> LENGTH: 16
<212> TYPE: PRT
<213> ORGANISM: Homo sapiens

<400> SEQUENCE: 130

Ser Ala Leu Phe Trp Glu Gln His Asp Leu Val Tyr Gly Asp Trp Thr
1               5                   10                  15

<210> SEQ ID NO 131
<211> LENGTH: 24
<212> TYPE: PRT
<213> ORGANISM: Homo sapiens

<400> SEQUENCE: 131

Phe Asn Ala Thr Ser Ala Leu Phe Trp Glu Gln His Asp Leu Val Tyr
1               5                   10                  15

Gly Asp Trp Thr Ser Gly Glu Asn
            20

<210> SEQ ID NO 132
<211> LENGTH: 23
<212> TYPE: PRT
<213> ORGANISM: Homo sapiens

<400> SEQUENCE: 132

Phe Asn Ala Thr Ser Ala Leu Phe Trp Glu Gln His Asp Leu Val Tyr
1               5                   10                  15

Gly Asp Trp Thr Ser Gly Glu
            20

<210> SEQ ID NO 133
<211> LENGTH: 22
<212> TYPE: PRT
<213> ORGANISM: Homo sapiens

<400> SEQUENCE: 133
```

Phe Asn Ala Thr Ser Ala Leu Phe Trp Glu Gln His Asp Leu Val Tyr
1               5                   10                  15

Gly Asp Trp Thr Ser Gly
            20

<210> SEQ ID NO 134
<211> LENGTH: 21
<212> TYPE: PRT
<213> ORGANISM: Homo sapiens

<400> SEQUENCE: 134

Phe Asn Ala Thr Ser Ala Leu Phe Trp Glu Gln His Asp Leu Val Tyr
1               5                   10                  15

Gly Asp Trp Thr Ser
            20

<210> SEQ ID NO 135
<211> LENGTH: 20
<212> TYPE: PRT
<213> ORGANISM: Homo sapiens

<400> SEQUENCE: 135

Phe Asn Ala Thr Ser Ala Leu Phe Trp Glu Gln His Asp Leu Val Tyr
1               5                   10                  15

Gly Asp Trp Thr
            20

<210> SEQ ID NO 136
<211> LENGTH: 23
<212> TYPE: PRT
<213> ORGANISM: Homo sapiens

<400> SEQUENCE: 136

Asn Ala Thr Ser Ala Leu Phe Trp Glu Gln His Asp Leu Val Tyr Gly
1               5                   10                  15

Asp Trp Thr Ser Gly Glu Asn
            20

<210> SEQ ID NO 137
<211> LENGTH: 22
<212> TYPE: PRT
<213> ORGANISM: Homo sapiens

<400> SEQUENCE: 137

Ala Thr Ser Ala Leu Phe Trp Glu Gln His Asp Leu Val Tyr Gly Asp
1               5                   10                  15

Trp Thr Ser Gly Glu Asn
            20

<210> SEQ ID NO 138
<211> LENGTH: 21
<212> TYPE: PRT
<213> ORGANISM: Homo sapiens

<400> SEQUENCE: 138

Thr Ser Ala Leu Phe Trp Glu Gln His Asp Leu Val Tyr Gly Asp Trp
1               5                   10                  15

Thr Ser Gly Glu Asn
            20

<210> SEQ ID NO 139
<211> LENGTH: 20

```
<212> TYPE: PRT
<213> ORGANISM: Homo sapiens

<400> SEQUENCE: 139

Ser Ala Leu Phe Trp Glu Gln His Asp Leu Val Tyr Gly Asp Trp Thr
1               5                   10                  15
Ser Gly Glu Asn
            20

<210> SEQ ID NO 140
<211> LENGTH: 9
<212> TYPE: PRT
<213> ORGANISM: Homo sapiens

<400> SEQUENCE: 140

Tyr Phe Asn Asp Tyr Trp Asn Leu Gln
1               5

<210> SEQ ID NO 141
<211> LENGTH: 17
<212> TYPE: PRT
<213> ORGANISM: Homo sapiens

<400> SEQUENCE: 141

Tyr Pro Ile Ile Tyr Phe Asn Asp Tyr Trp Asn Leu Gln Lys Asp Tyr
1               5                   10                  15
Tyr

<210> SEQ ID NO 142
<211> LENGTH: 16
<212> TYPE: PRT
<213> ORGANISM: Homo sapiens

<400> SEQUENCE: 142

Tyr Pro Ile Ile Tyr Phe Asn Asp Tyr Trp Asn Leu Gln Lys Asp Tyr
1               5                   10                  15

<210> SEQ ID NO 143
<211> LENGTH: 15
<212> TYPE: PRT
<213> ORGANISM: Homo sapiens

<400> SEQUENCE: 143

Tyr Pro Ile Ile Tyr Phe Asn Asp Tyr Trp Asn Leu Gln Lys Asp
1               5                   10                  15

<210> SEQ ID NO 144
<211> LENGTH: 14
<212> TYPE: PRT
<213> ORGANISM: Homo sapiens

<400> SEQUENCE: 144

Tyr Pro Ile Ile Tyr Phe Asn Asp Tyr Trp Asn Leu Gln Lys
1               5                   10

<210> SEQ ID NO 145
<211> LENGTH: 13
<212> TYPE: PRT
<213> ORGANISM: Homo sapiens

<400> SEQUENCE: 145

Tyr Pro Ile Ile Tyr Phe Asn Asp Tyr Trp Asn Leu Gln
1               5                   10
```

<210> SEQ ID NO 146
<211> LENGTH: 16
<212> TYPE: PRT
<213> ORGANISM: Homo sapiens

<400> SEQUENCE: 146

Pro Ile Ile Tyr Phe Asn Asp Tyr Trp Asn Leu Gln Lys Asp Tyr Tyr
1               5                   10                  15

<210> SEQ ID NO 147
<211> LENGTH: 15
<212> TYPE: PRT
<213> ORGANISM: Homo sapiens

<400> SEQUENCE: 147

Ile Ile Tyr Phe Asn Asp Tyr Trp Asn Leu Gln Lys Asp Tyr Tyr
1               5                   10                  15

<210> SEQ ID NO 148
<211> LENGTH: 14
<212> TYPE: PRT
<213> ORGANISM: Homo sapiens

<400> SEQUENCE: 148

Ile Tyr Phe Asn Asp Tyr Trp Asn Leu Gln Lys Asp Tyr Tyr
1               5                   10

<210> SEQ ID NO 149
<211> LENGTH: 13
<212> TYPE: PRT
<213> ORGANISM: Homo sapiens

<400> SEQUENCE: 149

Tyr Phe Asn Asp Tyr Trp Asn Leu Gln Lys Asp Tyr Tyr
1               5                   10

<210> SEQ ID NO 150
<211> LENGTH: 3
<212> TYPE: PRT
<213> ORGANISM: Homo sapiens

<400> SEQUENCE: 150

Trp Thr Ser
1

<210> SEQ ID NO 151
<211> LENGTH: 4
<212> TYPE: PRT
<213> ORGANISM: Homo sapiens

<400> SEQUENCE: 151

Pro Lys Asp Thr
1

<210> SEQ ID NO 152
<211> LENGTH: 14
<212> TYPE: PRT
<213> ORGANISM: Homo sapiens

<400> SEQUENCE: 152

Ala Pro Arg Val Ala Ser Arg Asn Leu Phe Pro Lys Asp Thr
1               5                   10

<210> SEQ ID NO 153

```
<211> LENGTH: 13
<212> TYPE: PRT
<213> ORGANISM: Homo sapiens

<400> SEQUENCE: 153

Pro Arg Val Ala Ser Arg Asn Leu Phe Pro Lys Asp Thr
1               5                   10

<210> SEQ ID NO 154
<211> LENGTH: 12
<212> TYPE: PRT
<213> ORGANISM: Homo sapiens

<400> SEQUENCE: 154

Arg Val Ala Ser Arg Asn Leu Phe Pro Lys Asp Thr
1               5                   10

<210> SEQ ID NO 155
<211> LENGTH: 11
<212> TYPE: PRT
<213> ORGANISM: Homo sapiens

<400> SEQUENCE: 155

Val Ala Ser Arg Asn Leu Phe Pro Lys Asp Thr
1               5                   10

<210> SEQ ID NO 156
<211> LENGTH: 10
<212> TYPE: PRT
<213> ORGANISM: Homo sapiens

<400> SEQUENCE: 156

Ala Ser Arg Asn Leu Phe Pro Lys Asp Thr
1               5                   10

<210> SEQ ID NO 157
<211> LENGTH: 9
<212> TYPE: PRT
<213> ORGANISM: Homo sapiens

<400> SEQUENCE: 157

Ser Arg Asn Leu Phe Pro Lys Asp Thr
1               5

<210> SEQ ID NO 158
<211> LENGTH: 8
<212> TYPE: PRT
<213> ORGANISM: Homo sapiens

<400> SEQUENCE: 158

Arg Asn Leu Phe Pro Lys Asp Thr
1               5

<210> SEQ ID NO 159
<211> LENGTH: 7
<212> TYPE: PRT
<213> ORGANISM: Homo sapiens

<400> SEQUENCE: 159

Asn Leu Phe Pro Lys Asp Thr
1               5

<210> SEQ ID NO 160
<211> LENGTH: 6
<212> TYPE: PRT
```

<213> ORGANISM: Homo sapiens

<400> SEQUENCE: 160

Leu Phe Pro Lys Asp Thr
1               5

<210> SEQ ID NO 161
<211> LENGTH: 5
<212> TYPE: PRT
<213> ORGANISM: Homo sapiens

<400> SEQUENCE: 161

Phe Pro Lys Asp Thr
1               5

<210> SEQ ID NO 162
<211> LENGTH: 14
<212> TYPE: PRT
<213> ORGANISM: Homo sapiens

<400> SEQUENCE: 162

Pro Arg Val Ala Ser Arg Asn Leu Phe Pro Lys Asp Thr Leu
1               5                   10

<210> SEQ ID NO 163
<211> LENGTH: 13
<212> TYPE: PRT
<213> ORGANISM: Homo sapiens

<400> SEQUENCE: 163

Val Ala Ser Arg Asn Leu Phe Pro Lys Asp Thr Leu Met
1               5                   10

<210> SEQ ID NO 164
<211> LENGTH: 13
<212> TYPE: PRT
<213> ORGANISM: Homo sapiens

<400> SEQUENCE: 164

Ala Ser Arg Asn Leu Phe Pro Lys Asp Thr Leu Met Asn
1               5                   10

<210> SEQ ID NO 165
<211> LENGTH: 13
<212> TYPE: PRT
<213> ORGANISM: Homo sapiens

<400> SEQUENCE: 165

Ser Arg Asn Leu Phe Pro Lys Asp Thr Leu Met Asn Leu
1               5                   10

<210> SEQ ID NO 166
<211> LENGTH: 13
<212> TYPE: PRT
<213> ORGANISM: Homo sapiens

<400> SEQUENCE: 166

Arg Asn Leu Phe Pro Lys Asp Thr Leu Met Asn Leu His
1               5                   10

<210> SEQ ID NO 167
<211> LENGTH: 13
<212> TYPE: PRT
<213> ORGANISM: Homo sapiens

```
<400> SEQUENCE: 167

Asn Leu Phe Pro Lys Asp Thr Leu Met Asn Leu His Val
1               5                   10

<210> SEQ ID NO 168
<211> LENGTH: 13
<212> TYPE: PRT
<213> ORGANISM: Homo sapiens

<400> SEQUENCE: 168

Leu Phe Pro Lys Asp Thr Leu Met Asn Leu His Val Tyr
1               5                   10

<210> SEQ ID NO 169
<211> LENGTH: 13
<212> TYPE: PRT
<213> ORGANISM: Homo sapiens

<400> SEQUENCE: 169

Phe Pro Lys Asp Thr Leu Met Asn Leu His Val Tyr Ile
1               5                   10

<210> SEQ ID NO 170
<211> LENGTH: 13
<212> TYPE: PRT
<213> ORGANISM: Homo sapiens

<400> SEQUENCE: 170

Pro Lys Asp Thr Leu Met Asn Leu His Val Tyr Ile Ser
1               5                   10

<210> SEQ ID NO 171
<211> LENGTH: 12
<212> TYPE: PRT
<213> ORGANISM: Homo sapiens

<400> SEQUENCE: 171

Pro Lys Asp Thr Leu Met Asn Leu His Val Tyr Ile
1               5                   10

<210> SEQ ID NO 172
<211> LENGTH: 11
<212> TYPE: PRT
<213> ORGANISM: Homo sapiens

<400> SEQUENCE: 172

Pro Lys Asp Thr Leu Met Asn Leu His Val Tyr
1               5                   10

<210> SEQ ID NO 173
<211> LENGTH: 10
<212> TYPE: PRT
<213> ORGANISM: Homo sapiens

<400> SEQUENCE: 173

Pro Lys Asp Thr Leu Met Asn Leu His Val
1               5                   10

<210> SEQ ID NO 174
<211> LENGTH: 9
<212> TYPE: PRT
<213> ORGANISM: Homo sapiens

<400> SEQUENCE: 174
```

-continued

Pro Lys Asp Thr Leu Met Asn Leu His
1               5

<210> SEQ ID NO 175
<211> LENGTH: 8
<212> TYPE: PRT
<213> ORGANISM: Homo sapiens

<400> SEQUENCE: 175

Pro Lys Asp Thr Leu Met Asn Leu
1               5

<210> SEQ ID NO 176
<211> LENGTH: 7
<212> TYPE: PRT
<213> ORGANISM: Homo sapiens

<400> SEQUENCE: 176

Pro Lys Asp Thr Leu Met Asn
1               5

<210> SEQ ID NO 177
<211> LENGTH: 6
<212> TYPE: PRT
<213> ORGANISM: Homo sapiens

<400> SEQUENCE: 177

Pro Lys Asp Thr Leu Met
1               5

<210> SEQ ID NO 178
<211> LENGTH: 5
<212> TYPE: PRT
<213> ORGANISM: Homo sapiens

<400> SEQUENCE: 178

Pro Lys Asp Thr Leu
1               5

<210> SEQ ID NO 179
<211> LENGTH: 21
<212> TYPE: PRT
<213> ORGANISM: Homo sapiens

<400> SEQUENCE: 179

Ala Ala Ala Gln Glu Ala Asp Gly Ala Arg Ser Ala Val Val Ala Ala
1               5                   10                  15

Gly Gly Gly Ser Gly
            20

<210> SEQ ID NO 180
<211> LENGTH: 21
<212> TYPE: PRT
<213> ORGANISM: Homo sapiens

<400> SEQUENCE: 180

Ser Gly Gln Val Thr Ser Asn Gly Ser Ile Gly Arg Asp Pro Pro Ala
1               5                   10                  15

Glu Thr Gln Pro Gly
            20

<210> SEQ ID NO 181
<211> LENGTH: 21
<212> TYPE: PRT

<213> ORGANISM: Homo sapiens

<400> SEQUENCE: 181

Gln Asn Pro Pro Ala Gln Pro Ala Pro Asn Ala Trp Gln Val Ile Lys
1               5                   10                  15

Gly Val Leu Phe Gly
            20

<210> SEQ ID NO 182
<211> LENGTH: 21
<212> TYPE: PRT
<213> ORGANISM: Homo sapiens

<400> SEQUENCE: 182

Arg Ile Phe Ile Ile Trp Ala Ile Ser Ser Trp Phe Arg Arg Gly Pro
1               5                   10                  15

Ala Pro Gln Asp Gly
            20

<210> SEQ ID NO 183
<211> LENGTH: 21
<212> TYPE: PRT
<213> ORGANISM: Homo sapiens

<400> SEQUENCE: 183

Gln Ala Gly Pro Gly Gly Ala Pro Arg Val Ala Ser Arg Asn Leu Phe
1               5                   10                  15

Pro Lys Asp Thr Gly
            20

<210> SEQ ID NO 184
<211> LENGTH: 21
<212> TYPE: PRT
<213> ORGANISM: Homo sapiens

<400> SEQUENCE: 184

Leu Met Asn Leu His Val Tyr Ile Ser Glu His Glu His Phe Thr Asp
1               5                   10                  15

Phe Asn Ala Thr Gly
            20

<210> SEQ ID NO 185
<211> LENGTH: 21
<212> TYPE: PRT
<213> ORGANISM: Homo sapiens

<400> SEQUENCE: 185

Ser Ala Leu Phe Trp Glu Gln His Asp Leu Val Tyr Gly Asp Trp Thr
1               5                   10                  15

Ser Gly Glu Asn Gly
            20

<210> SEQ ID NO 186
<211> LENGTH: 21
<212> TYPE: PRT
<213> ORGANISM: Homo sapiens

<400> SEQUENCE: 186

Ser Asp Gly Cys Tyr Glu His Phe Ala Glu Leu Asp Ile Pro Gln Ser
1               5                   10                  15

Val Gln Gln Asn Gly
            20

<210> SEQ ID NO 187
<211> LENGTH: 21
<212> TYPE: PRT
<213> ORGANISM: Homo sapiens

<400> SEQUENCE: 187

Gly Ser Ile Tyr Ile His Val Tyr Phe Thr Lys Ser Gly Phe His Pro
1               5                   10                  15

Asp Pro Arg Gln Gly
            20

<210> SEQ ID NO 188
<211> LENGTH: 21
<212> TYPE: PRT
<213> ORGANISM: Homo sapiens

<400> SEQUENCE: 188

Lys Ala Leu Tyr Arg Arg Leu Ala Thr Val His Met Ser Arg Met Ile
1               5                   10                  15

Asn Lys Tyr Lys Gly
            20

<210> SEQ ID NO 189
<211> LENGTH: 21
<212> TYPE: PRT
<213> ORGANISM: Homo sapiens

<400> SEQUENCE: 189

Arg Arg Arg Phe Gln Lys Thr Lys Asn Leu Leu Thr Gly Glu Thr Glu
1               5                   10                  15

Ala Asp Pro Glu Gly
            20

<210> SEQ ID NO 190
<211> LENGTH: 21
<212> TYPE: PRT
<213> ORGANISM: Homo sapiens

<400> SEQUENCE: 190

Met Ile Lys Arg Ala Glu Asp Tyr Gly Pro Val Glu Val Ile Ser His
1               5                   10                  15

Trp His Pro Asn Gly
            20

<210> SEQ ID NO 191
<211> LENGTH: 21
<212> TYPE: PRT
<213> ORGANISM: Homo sapiens

<400> SEQUENCE: 191

Ile Thr Ile Asn Ile Val Asp Asp His Thr Pro Trp Val Lys Gly Ser
1               5                   10                  15

Val Pro Pro Pro Gly
            20

<210> SEQ ID NO 192
<211> LENGTH: 21
<212> TYPE: PRT
<213> ORGANISM: Homo sapiens

<400> SEQUENCE: 192

```
Leu Asp Gln Tyr Val Lys Phe Asp Ala Val Ser Gly Asp Tyr Tyr Pro
1               5                   10                  15

Ile Ile Tyr Phe Gly
            20

<210> SEQ ID NO 193
<211> LENGTH: 21
<212> TYPE: PRT
<213> ORGANISM: Homo sapiens

<400> SEQUENCE: 193

Asn Asp Tyr Trp Asn Leu Gln Lys Asp Tyr Tyr Pro Ile Asn Glu Ser
1               5                   10                  15

Leu Ala Ser Leu Gly
            20

<210> SEQ ID NO 194
<211> LENGTH: 21
<212> TYPE: PRT
<213> ORGANISM: Homo sapiens

<400> SEQUENCE: 194

Pro Leu Arg Val Ser Phe Cys Pro Leu Ser Leu Trp Arg Trp Gln Leu
1               5                   10                  15

Tyr Ala Ala Gln Gly
            20

<210> SEQ ID NO 195
<211> LENGTH: 21
<212> TYPE: PRT
<213> ORGANISM: Homo sapiens

<400> SEQUENCE: 195

Ser Thr Lys Ser Pro Trp Asn Phe Leu Gly Asp Glu Leu Tyr Glu Gln
1               5                   10                  15

Ser Asp Glu Glu Gly
            20

<210> SEQ ID NO 196
<211> LENGTH: 21
<212> TYPE: PRT
<213> ORGANISM: Homo sapiens

<400> SEQUENCE: 196

Tyr Glu Gln Ser Asp Glu Glu Gln Asp Ser Val Lys Val Ala Leu Leu
1               5                   10                  15

Glu Thr Asn Pro Gly
            20

<210> SEQ ID NO 197
<211> LENGTH: 21
<212> TYPE: PRT
<213> ORGANISM: Homo sapiens

<400> SEQUENCE: 197

Leu Trp Arg Trp Gln Leu Tyr Ala Ala Gln Ser Thr Lys Ser Pro Trp
1               5                   10                  15

Asn Phe Leu Gly Gly
            20

<210> SEQ ID NO 198
<211> LENGTH: 21
```

```
<212> TYPE: PRT
<213> ORGANISM: Homo sapiens

<400> SEQUENCE: 198

Tyr Pro Ile Asn Glu Ser Leu Ala Ser Leu Pro Leu Arg Val Ser Phe
1               5                   10                  15

Cys Pro Leu Ser Gly
            20

<210> SEQ ID NO 199
<211> LENGTH: 21
<212> TYPE: PRT
<213> ORGANISM: Homo sapiens

<400> SEQUENCE: 199

Gly Asp Tyr Tyr Pro Ile Ile Tyr Phe Asn Asp Tyr Trp Asn Leu Gln
1               5                   10                  15

Lys Asp Tyr Tyr Gly
            20

<210> SEQ ID NO 200
<211> LENGTH: 21
<212> TYPE: PRT
<213> ORGANISM: Homo sapiens

<400> SEQUENCE: 200

Trp Gln Val Ile Lys Gly Val Leu Phe Arg Ile Phe Ile Ile Trp Ala
1               5                   10                  15

Ile Ser Ser Trp Gly
            20

<210> SEQ ID NO 201
<211> LENGTH: 21
<212> TYPE: PRT
<213> ORGANISM: Homo sapiens

<400> SEQUENCE: 201

Arg Asn Leu Phe Pro Lys Asp Thr Leu Met Asn Leu His Val Tyr Ile
1               5                   10                  15

Ser Glu His Glu Gly
            20

<210> SEQ ID NO 202
<211> LENGTH: 21
<212> TYPE: PRT
<213> ORGANISM: Homo sapiens

<400> SEQUENCE: 202

Phe Thr Asp Phe Asn Ala Thr Ser Ala Leu Phe Trp Glu Gln His Asp
1               5                   10                  15

Leu Val Tyr Gly Gly
            20

<210> SEQ ID NO 203
<211> LENGTH: 20
<212> TYPE: PRT
<213> ORGANISM: Homo sapiens

<400> SEQUENCE: 203

Ala Ala Ala Gln Glu Ala Asp Gly Ala Arg Ser Ala Val Val Ala Ala
1               5                   10                  15

Gly Gly Gly Ser
```

-continued

```
            20

<210> SEQ ID NO 204
<211> LENGTH: 20
<212> TYPE: PRT
<213> ORGANISM: Homo sapiens

<400> SEQUENCE: 204

Ser Gly Gln Val Thr Ser Asn Gly Ser Ile Gly Arg Asp Pro Pro Ala
1               5                   10                  15

Glu Thr Gln Pro
            20

<210> SEQ ID NO 205
<211> LENGTH: 20
<212> TYPE: PRT
<213> ORGANISM: Homo sapiens

<400> SEQUENCE: 205

Gln Asn Pro Pro Ala Gln Pro Ala Pro Asn Ala Trp Gln Val Ile Lys
1               5                   10                  15

Gly Val Leu Phe
            20

<210> SEQ ID NO 206
<211> LENGTH: 20
<212> TYPE: PRT
<213> ORGANISM: Homo sapiens

<400> SEQUENCE: 206

Arg Ile Phe Ile Ile Trp Ala Ile Ser Ser Trp Phe Arg Arg Gly Pro
1               5                   10                  15

Ala Pro Gln Asp
            20

<210> SEQ ID NO 207
<211> LENGTH: 20
<212> TYPE: PRT
<213> ORGANISM: Homo sapiens

<400> SEQUENCE: 207

Gln Ala Gly Pro Gly Gly Ala Pro Arg Val Ala Ser Arg Asn Leu Phe
1               5                   10                  15

Pro Lys Asp Thr
            20

<210> SEQ ID NO 208
<211> LENGTH: 20
<212> TYPE: PRT
<213> ORGANISM: Homo sapiens

<400> SEQUENCE: 208

Leu Met Asn Leu His Val Tyr Ile Ser Glu His Glu His Phe Thr Asp
1               5                   10                  15

Phe Asn Ala Thr
            20

<210> SEQ ID NO 209
<211> LENGTH: 20
<212> TYPE: PRT
<213> ORGANISM: Homo sapiens

<400> SEQUENCE: 209
```

```
Ser Ala Leu Phe Trp Glu Gln His Asp Leu Val Tyr Gly Asp Trp Thr
1               5                   10                  15

Ser Gly Glu Asn
            20

<210> SEQ ID NO 210
<211> LENGTH: 20
<212> TYPE: PRT
<213> ORGANISM: Homo sapiens

<400> SEQUENCE: 210

Ser Asp Gly Cys Tyr Glu His Phe Ala Glu Leu Asp Ile Pro Gln Ser
1               5                   10                  15

Val Gln Gln Asn
            20

<210> SEQ ID NO 211
<211> LENGTH: 20
<212> TYPE: PRT
<213> ORGANISM: Homo sapiens

<400> SEQUENCE: 211

Gly Ser Ile Tyr Ile His Val Tyr Phe Thr Lys Ser Gly Phe His Pro
1               5                   10                  15

Asp Pro Arg Gln
            20

<210> SEQ ID NO 212
<211> LENGTH: 20
<212> TYPE: PRT
<213> ORGANISM: Homo sapiens

<400> SEQUENCE: 212

Lys Ala Leu Tyr Arg Arg Leu Ala Thr Val His Met Ser Arg Met Ile
1               5                   10                  15

Asn Lys Tyr Lys
            20

<210> SEQ ID NO 213
<211> LENGTH: 20
<212> TYPE: PRT
<213> ORGANISM: Homo sapiens

<400> SEQUENCE: 213

Arg Arg Arg Phe Gln Lys Thr Lys Asn Leu Leu Thr Gly Glu Thr Glu
1               5                   10                  15

Ala Asp Pro Glu
            20

<210> SEQ ID NO 214
<211> LENGTH: 20
<212> TYPE: PRT
<213> ORGANISM: Homo sapiens

<400> SEQUENCE: 214

Met Ile Lys Arg Ala Glu Asp Tyr Gly Pro Val Glu Val Ile Ser His
1               5                   10                  15

Trp His Pro Asn
            20

<210> SEQ ID NO 215
```

```
<211> LENGTH: 20
<212> TYPE: PRT
<213> ORGANISM: Homo sapiens

<400> SEQUENCE: 215

Ile Thr Ile Asn Ile Val Asp Asp His Thr Pro Trp Val Lys Gly Ser
1               5                   10                  15

Val Pro Pro Pro
            20

<210> SEQ ID NO 216
<211> LENGTH: 20
<212> TYPE: PRT
<213> ORGANISM: Homo sapiens

<400> SEQUENCE: 216

Leu Asp Gln Tyr Val Lys Phe Asp Ala Val Ser Gly Asp Tyr Tyr Pro
1               5                   10                  15

Ile Ile Tyr Phe
            20

<210> SEQ ID NO 217
<211> LENGTH: 20
<212> TYPE: PRT
<213> ORGANISM: Homo sapiens

<400> SEQUENCE: 217

Asn Asp Tyr Trp Asn Leu Gln Lys Asp Tyr Tyr Pro Ile Asn Glu Ser
1               5                   10                  15

Leu Ala Ser Leu
            20

<210> SEQ ID NO 218
<211> LENGTH: 20
<212> TYPE: PRT
<213> ORGANISM: Homo sapiens

<400> SEQUENCE: 218

Pro Leu Arg Val Ser Phe Cys Pro Leu Ser Leu Trp Arg Trp Gln Leu
1               5                   10                  15

Tyr Ala Ala Gln
            20

<210> SEQ ID NO 219
<211> LENGTH: 20
<212> TYPE: PRT
<213> ORGANISM: Homo sapiens

<400> SEQUENCE: 219

Ser Thr Lys Ser Pro Trp Asn Phe Leu Gly Asp Glu Leu Tyr Glu Gln
1               5                   10                  15

Ser Asp Glu Glu
            20

<210> SEQ ID NO 220
<211> LENGTH: 20
<212> TYPE: PRT
<213> ORGANISM: Homo sapiens

<400> SEQUENCE: 220

Tyr Glu Gln Ser Asp Glu Glu Gln Asp Ser Val Lys Val Ala Leu Leu
1               5                   10                  15
```

```
Glu Thr Asn Pro
            20

<210> SEQ ID NO 221
<211> LENGTH: 20
<212> TYPE: PRT
<213> ORGANISM: Homo sapiens

<400> SEQUENCE: 221

Leu Trp Arg Trp Gln Leu Tyr Ala Ala Gln Ser Thr Lys Ser Pro Trp
1               5                   10                  15

Asn Phe Leu Gly
            20

<210> SEQ ID NO 222
<211> LENGTH: 20
<212> TYPE: PRT
<213> ORGANISM: Homo sapiens

<400> SEQUENCE: 222

Tyr Pro Ile Asn Glu Ser Leu Ala Ser Leu Pro Leu Arg Val Ser Phe
1               5                   10                  15

Cys Pro Leu Ser
            20

<210> SEQ ID NO 223
<211> LENGTH: 20
<212> TYPE: PRT
<213> ORGANISM: Homo sapiens

<400> SEQUENCE: 223

Gly Asp Tyr Tyr Pro Ile Ile Tyr Phe Asn Asp Tyr Trp Asn Leu Gln
1               5                   10                  15

Lys Asp Tyr Tyr
            20

<210> SEQ ID NO 224
<211> LENGTH: 20
<212> TYPE: PRT
<213> ORGANISM: Homo sapiens

<400> SEQUENCE: 224

Trp Gln Val Ile Lys Gly Val Leu Phe Arg Ile Phe Ile Ile Trp Ala
1               5                   10                  15

Ile Ser Ser Trp
            20

<210> SEQ ID NO 225
<211> LENGTH: 20
<212> TYPE: PRT
<213> ORGANISM: Homo sapiens

<400> SEQUENCE: 225

Arg Asn Leu Phe Pro Lys Asp Thr Leu Met Asn Leu His Val Tyr Ile
1               5                   10                  15

Ser Glu His Glu
            20

<210> SEQ ID NO 226
<211> LENGTH: 20
<212> TYPE: PRT
<213> ORGANISM: Homo sapiens
```

-continued

<400> SEQUENCE: 226

Phe Thr Asp Phe Asn Ala Thr Ser Ala Leu Phe Trp Glu Gln His Asp
1               5                   10                  15

Leu Val Tyr Gly
            20

<210> SEQ ID NO 227
<211> LENGTH: 354
<212> TYPE: PRT
<213> ORGANISM: Homo sapiens

<400> SEQUENCE: 227

Met Ala Ala Gln Glu Ala Asp Gly Ala Arg Ser Ala Val Val Ala
1               5                   10                  15

Ala Gly Gly Gly Ser Ser Gly Gln Val Thr Ser Asn Gly Ser Ile Gly
            20                  25                  30

Arg Asp Pro Pro Ala Glu Thr Gln Pro Gln Asn Pro Pro Ala Gln Pro
        35                  40                  45

Ala Pro Asn Ala Trp Gln Val Ile Lys Gly Val Leu Phe Arg Ile Phe
    50                  55                  60

Ile Ile Trp Ala Ile Ser Ser Trp Phe Arg Arg Gly Pro Ala Pro Gln
65                  70                  75                  80

Asp Gln Ala Gly Pro Gly Gly Ala Pro Arg Val Ala Ser Arg Asn Leu
                85                  90                  95

Phe Pro Lys Asp Thr Leu Met Asn Leu His Val Tyr Ile Ser Glu His
            100                 105                 110

Glu His Phe Thr Asp Phe Asn Ala Thr Ser Ala Leu Phe Trp Glu Gln
        115                 120                 125

His Asp Leu Val Tyr Gly Asp Trp Thr Ser Gly Glu Asn Ser Asp Gly
    130                 135                 140

Cys Tyr Glu His Phe Ala Glu Leu Asp Ile Pro Gln Ser Val Gln Gln
145                 150                 155                 160

Asn Gly Ser Ile Tyr Ile His Val Tyr Phe Thr Lys Ser Gly Phe His
                165                 170                 175

Pro Asp Pro Arg Gln Lys Ala Leu Tyr Arg Arg Leu Ala Thr Val His
            180                 185                 190

Met Ser Arg Met Ile Asn Lys Tyr Lys Arg Arg Phe Gln Lys Thr
        195                 200                 205

Lys Asn Leu Leu Thr Gly Glu Thr Glu Ala Asp Pro Glu Met Ile Lys
    210                 215                 220

Arg Ala Glu Asp Tyr Gly Pro Val Glu Val Ile Ser His Trp His Pro
225                 230                 235                 240

Asn Ile Thr Ile Asn Ile Val Asp Asp His Thr Pro Trp Val Lys Gly
                245                 250                 255

Ser Val Pro Pro Leu Asp Gln Tyr Val Lys Phe Asp Ala Val Ser
            260                 265                 270

Gly Asp Tyr Tyr Pro Ile Ile Tyr Phe Asn Asp Tyr Trp Asn Leu Gln
        275                 280                 285

Lys Asp Tyr Tyr Pro Ile Asn Glu Ser Leu Ala Ser Leu Pro Leu Arg
    290                 295                 300

Val Ser Phe Cys Pro Leu Ser Leu Trp Arg Trp Gln Leu Tyr Ala Ala
305                 310                 315                 320

Gln Ser Thr Lys Ser Pro Trp Asn Phe Leu Gly Asp Glu Leu Tyr Glu
                325                 330                 335

Gln Ser Asp Glu Glu Gln Asp Ser Val Lys Val Ala Leu Leu Glu Thr
            340                 345                 350

Asn Pro

<210> SEQ ID NO 228
<211> LENGTH: 5
<212> TYPE: PRT
<213> ORGANISM: Homo sapiens

<400> SEQUENCE: 228

Gly Gly Gly Gly Ser
1               5

<210> SEQ ID NO 229
<211> LENGTH: 3
<212> TYPE: PRT
<213> ORGANISM: Homo sapiens

<400> SEQUENCE: 229

Pro Lys Asp
1

<210> SEQ ID NO 230
<211> LENGTH: 15
<212> TYPE: PRT
<213> ORGANISM: Homo sapiens

<400> SEQUENCE: 230

Gly Gly Ala Pro Arg Val Ala Ser Arg Asn Leu Phe Pro Lys Asp
1               5                   10                  15

<210> SEQ ID NO 231
<211> LENGTH: 15
<212> TYPE: PRT
<213> ORGANISM: Homo sapiens

<400> SEQUENCE: 231

Arg Val Ala Ser Arg Asn Leu Phe Pro Lys Asp Thr Leu Met Asn
1               5                   10                  15

<210> SEQ ID NO 232
<211> LENGTH: 15
<212> TYPE: PRT
<213> ORGANISM: Homo sapiens

<400> SEQUENCE: 232

Arg Asn Leu Phe Pro Lys Asp Thr Leu Met Asn Leu His Val Tyr
1               5                   10                  15

<210> SEQ ID NO 233
<211> LENGTH: 15
<212> TYPE: PRT
<213> ORGANISM: Homo sapiens

<400> SEQUENCE: 233

Pro Lys Asp Thr Leu Met Asn Leu His Val Tyr Ile Ser Glu His
1               5                   10                  15

<210> SEQ ID NO 234
<211> LENGTH: 15
<212> TYPE: PRT
<213> ORGANISM: Homo sapiens

<400> SEQUENCE: 234

```
Leu Asp Gln Tyr Val Lys Phe Asp Ala Val Ser Gly Asp Tyr Tyr
1               5                   10                  15

<210> SEQ ID NO 235
<211> LENGTH: 15
<212> TYPE: PRT
<213> ORGANISM: Homo sapiens

<400> SEQUENCE: 235

Val Lys Phe Asp Ala Val Ser Gly Asp Tyr Tyr Pro Ile Ile Tyr
1               5                   10                  15

<210> SEQ ID NO 236
<211> LENGTH: 15
<212> TYPE: PRT
<213> ORGANISM: Homo sapiens

<400> SEQUENCE: 236

Ala Val Ser Gly Asp Tyr Tyr Pro Ile Ile Tyr Phe Asn Asp Tyr
1               5                   10                  15

<210> SEQ ID NO 237
<211> LENGTH: 15
<212> TYPE: PRT
<213> ORGANISM: Homo sapiens

<400> SEQUENCE: 237

Asp Tyr Tyr Pro Ile Ile Tyr Phe Asn Asp Tyr Trp Asn Leu Gln
1               5                   10                  15

<210> SEQ ID NO 238
<211> LENGTH: 15
<212> TYPE: PRT
<213> ORGANISM: Homo sapiens

<400> SEQUENCE: 238

Ile Ile Tyr Phe Asn Asp Tyr Trp Asn Leu Gln Lys Asp Tyr Tyr
1               5                   10                  15

<210> SEQ ID NO 239
<211> LENGTH: 15
<212> TYPE: PRT
<213> ORGANISM: Homo sapiens

<400> SEQUENCE: 239

Asn Asp Tyr Trp Asn Leu Gln Lys Asp Tyr Tyr Pro Ile Asn Glu
1               5                   10                  15

<210> SEQ ID NO 240
<211> LENGTH: 15
<212> TYPE: PRT
<213> ORGANISM: Homo sapiens

<400> SEQUENCE: 240

Asn Leu Gln Lys Asp Tyr Tyr Pro Ile Asn Glu Ser Leu Ala Ser
1               5                   10                  15

<210> SEQ ID NO 241
<211> LENGTH: 13
<212> TYPE: PRT
<213> ORGANISM: Homo sapiens

<400> SEQUENCE: 241

Gln Lys Ala Leu Tyr Arg Arg Leu Ala Thr Val His Met
1               5                   10
```

```
<210> SEQ ID NO 242
<211> LENGTH: 14
<212> TYPE: PRT
<213> ORGANISM: Homo sapiens

<400> SEQUENCE: 242

Gln Lys Ala Leu Tyr Arg Arg Leu Ala Thr Val His Met Cys
1               5                   10

<210> SEQ ID NO 243
<211> LENGTH: 249
<212> TYPE: PRT
<213> ORGANISM: Homo sapiens

<400> SEQUENCE: 243

Asn Leu His Val Tyr Ile Ser Glu His Glu Phe Thr Asp Phe Asn
1               5                   10                  15

Ala Thr Ser Ala Leu Phe Trp Glu Gln His Asp Leu Val Tyr Gly Asp
                20                  25                  30

Trp Thr Ser Gly Glu Asn Ser Asp Gly Cys Tyr Glu His Phe Ala Glu
            35                  40                  45

Leu Asp Ile Pro Gln Ser Val Gln Gln Asn Gly Ser Ile Tyr Ile His
    50                  55                  60

Val Tyr Phe Thr Lys Ser Gly Phe His Pro Asp Pro Arg Gln Lys Ala
65                  70                  75                  80

Leu Tyr Arg Arg Leu Ala Thr Val His Met Ser Arg Met Ile Asn Lys
                85                  90                  95

Tyr Lys Ala Val Gly Phe Gln Lys Thr Lys Asn Leu Leu Thr Gly Glu
                100                 105                 110

Thr Glu Ala Asp Pro Glu Met Ile Lys Arg Ala Glu Asp Tyr Gly Pro
            115                 120                 125

Val Glu Val Ile Ser His Trp His Pro Asn Ile Thr Ile Asn Ile Val
    130                 135                 140

Asp Asp His Thr Pro Trp Val Lys Gly Ser Val Pro Pro Pro Leu Asp
145                 150                 155                 160

Gln Tyr Val Lys Phe Asp Ala Val Ser Gly Asp Tyr Pro Ile Ile
                165                 170                 175

Tyr Phe Asn Asp Tyr Trp Asn Leu Gln Lys Asp Tyr Tyr Pro Ile Asn
                180                 185                 190

Glu Ser Leu Ala Ser Leu Pro Leu Arg Val Ser Phe Cys Pro Leu Ser
            195                 200                 205

Leu Trp Arg Trp Gln Leu Tyr Ala Ala Gln Ser Thr Lys Ser Pro Trp
    210                 215                 220

Asn Phe Leu Gly Asp Glu Leu Tyr Glu Gln Ser Asp Glu Glu Gln Asp
225                 230                 235                 240

Ser Val Lys Val Ala Leu Leu Glu Thr
                245
```

THERAPEUTIC PEPTIDES THAT TARGET TGF-BETA INTERACTION

The Sequence Listing submitted herewith, entitled "Jul.-11-2019-Sequence-listing_ST25.txt", created Jun. 20, 2019 and having a size of 68,884 bytes, is incorporated herein by reference.

The present invention relates to the therapeutic use of agents which act to reduce the activity of transforming growth factor-beta (TGF-β, also referred to as TGFB or TGFb) i.e. TGF-β inhibitors. Such agents may be used to combat (i.e. to treat or prevent) conditions associated with or characterised by TGF-β over-expression, or more generally with conditions associated with increased, excessive or unwanted TGF-β levels and/or activity in the body. More particularly, the invention is based on the discovery that the normally intracellular protein Cleft Lip and Palate Transmembrane protein 1 (CLPTM1) is able to act as a cell surface receptor for TGF-β. Based on this identification of a novel TGF-β-receptor, the invention more specifically provides fragments of the CLPTM1 receptor or peptides based thereon or derived therefrom, which bind the CLPTM1 receptor, for use as TGF-β inhibitors, namely in preventing TGF-β from binding to the receptor and/or otherwise inhibiting the effect of TGF-β (i.e. the effect of the binding of TGF-β at the CLPTM1 receptor).

CLPTM1 is a transmembrane protein with a ~350 amino acid extracellular domain (the amino acid sequence of the ECD of human CLPTM1 is shown in SEQ ID NO: 2 and has 353 amino acids (representing amino acids 2-354 of SEQ ID NO: 1)). CLPTM1 has an unusual expression pattern and is expressed, for instance, in the cells of the immune system. Its physiological roles have not yet been fully elucidated but CLPTM1 has been identified to be genetically linked to cleft lip and palate (hence its name Cleft Lip and Palate Transmembrane protein 1). In work leading up to the present invention, we have discovered that CLPTM1 is expressed in Natural Killer cells (NK-cells) and macrophages, and we have further shown that it may be expressed by other cells of the immune system, such as various classes of lymphocytes, particularly various classes of T-lymphocytes; particular sub-sets of CD4+, CD8+ T-cells may express CLPTM1, as may particular subsets of CD3 CD45+ non-T-cells. In particular we have demonstrated cell surface expression; in many cases expression of CLPTM1 which has been reported is intracellular expression. We have shown, however, that in certain cell-types, including immune cells and cancer cells, and in response to certain physiological stimuli (e.g. inflammatory stimuli), CLPTM1 may be expressed at the cell surface.

We have also identified that CLPTM1 is a previously-unrecognised receptor for Growth and Differentiation Factor 15 (GDF15) (also known as MIC-1), along with the receptor pyroglutaminated RFamide Peptide Receptor (QRFPR). Binding agents for these receptors, specifically binding agents which inhibit the binding and/or effect of GDF15 at these receptors (i.e. antagonistic binding agents, or more particularly agents which are antagonistic with respect to the effect of GDF15 at the receptors) and polypeptides derived from these receptors and their use in various therapies are the subject of commonly-owned patent application WO 2017/013188 (PCT/EP2016/067338), the disclosure of which is hereby incorporated by reference in its entirety.

GDF15 is a member of the TGF-β superfamily, but has a relatively low (24%) sequence homology with other members of the superfamily. Elevated levels of GDF15 have been implicated in cancer, anorexia nervosa, osteoporosis, kidney disorders, pulmonary arterial hypertension, and cardiovascular disease, and also in cachexia and more generally in loss or suppression of appetite. GDF15 is a marker for mortality by any cause. The therapies proposed in WO 2017/013188 (PCT/EP2016/067338) are based on inhibiting the effect of GDF15, and thus for treating or preventing a condition associated with elevated or unwanted levels of GDF15, including the conditions listed above, and with respect to the receptor CLPTM1, particularly on reducing the immunosuppressive effects of GDF15, for example in the treatment of cancer.

As reported in WO 2017/013188 (PCT/EP2016/067338), stimulation of NK-92 cells by GDF15 was found to induce the co-localisation of TGFbRI (ALK5) and TGFbRII with CLPTM1, and to result in the phosphorylation of GSK3b. GDF15 had previously been associated with GSK3 phosphorylation, and phosphorylated (9/21) GSK3B is associated with reduced activation and cytotoxicity of cells of the innate immune system. The observation that CLPTM1 associates with the TGB-β receptor complex upon stimulation with GDF15 thus explains how GDF15 might decrease NK cell cytotoxicity. GDF15 has similar immunosuppressive effects to the TGF-β cytokines TGF-β 1, 2 and 3, including the repression of pro-inflammatory cytokines.

Such observations lead us to investigate whether CLPTM1 might also function as a receptor for other members of the TGF-β superfamily, and we have consequently discovered that TGF-β proteins, including TGF-β1, 2 and 3, are also ligands for CLPTM1 (see Example 1 below) and may mediate strong immunosuppressive effects through this receptor (see Example 2 below). Additionally, activation of CLPTM1 by TGF-β3, along with other CLPTM1 agonists including GDF15, was shown to mediate an alteration of the secretome of immune cells in the blood to an anti-inflammatory profile, causing an elevation of anti-inflammatory cytokines and a reduction of pro-inflammatory cytokines (see Example 6). We have further demonstrated that such immunosuppressive effects of TGF-β may be alleviated by inhibiting, or blocking, the CLPTM1 receptor using blocking, or antagonistic antibodies (as shown, for example, also in Example 2).

TGF-β3 is the closest relative to GDF15. TGF-β cytokines are involved in many different aspects of cell differentiation, embryogenesis and development, and are thought to be involved in regulating cellular adhesion and extracellular matrix formation during palate development. Knockout of TGF-β3 is associated with cleft lip formation in mice and is only partially rescued by TGF-β1 knock-in, indicating that this protein has specific biological roles. TGF-β expression is increased in fibrotic lung disease and other fibrotic disorders, and in chronic inflammatory conditions (lung fibrosis and other conditions: Thomas et al., Am. J Respir. Cell Mol. Biol. 2016, 55(6), 759-766); renal fibrosis: Samarakoon et al. 2013, 25(11), 2198-209; liver fibrosis: Alonso-Merino et al. PNAS 2016, 113(24):E3451-60; skin fibrosis, scarring and keloids: Hahn et al. Burns Trauma 2016, 4(1), 30.)

As noted above, TGF-β is also known to have an immunosuppressive role (Okamura T. et. al 2015. Nat Commun 19, 6329), and has been reported to have profound immunosuppressive actions including both innate and adaptive responses. This aspect of TGF-β biology is often overlooked. Recent investigations have demonstrated that TGF-β causes wide-ranging immune suppression, including blunting of pivotal early innate interferon responses. TGF-β is thus implicated in the pathology of various pathogen or parasite infections, including with viruses (e.g. HIV: (Maina et al. 2016. Cytokine 81, 109-116 and Lewis et al. 2016. J Clin Invest 3, 3799-3813); respiratory viruses: (Xia et al. 2017. PLoS Pathog 13, e1006138), bacteria (e.g. Mycobacteria/TB: Basile et al. 2017. Clin Exp Immunol 187, 160-173 and Feruglio et al. 2016. Scand J Immunol), protozoa (e.g. Leishmania: Elmekki et al. 2016. Ann Saudi Med 36, 73-77 and Crauwels et al; 2015. Autophagy 11, 285-297) Trypanosoma/Chagas Disease: Araújo et al. 2008. Cytokine Growth Factor Rev 19, 405-413; Plasmodium falciparum/malaria; Lourembam et al. 2013. Cytokine 64, 503-508); and helminths (e.g. Schistosoma: Graham et al. 2013. Circulation 128, 1354-1364). Thus, the inhibition of TGF-β, or TGF-β signalling, is becoming recognised as a therapeutic strategy for tackling infectious, inflammatory or fibrotic diseases characterised by TGF-β overexpression.

TGF-β is also implicated in the development and pathogenesis of cancer. TGF-β may have different effects, depending on the stage of the cancer; in early stages suppression of the TGF-β signalling pathway is known to correlate to the development of a more advanced stage in several human cancers (i.e. TGF-β plays a tumour-suppressive role) (Markovitz et al., Science 1995, 268 (5215)1336-8), but in late-stage cancers, over-expression of TGF-β is correlated to metastasis and immune suppression (Padua and Massague, Cell Research 2009, 19, 89-102). These opposite effects of the pathway on cancer progression can partly be explained by a loss of negative autocrine feedback on the tumour cells from the TGF-β ligands, in which the tumour cells have an acquired insensitivity to the effect of the TGF-β ligands on cell cycle control, yet effectively may affect bystander cells such as stromal cells and immune cells through paracrine signalling of excess secreted TGF-β ligands. Immune cells have not acquired genetic damage to downstream signalling components and are effectively suppressed by TGF-β ligands. TGF-β can suppress cell division, phagocytosis, and cytotoxicity by reducing perforin and Granzyme, downregulate MHC and reduce the levels of pro-inflammatory cytokines such as IFN and TNF required to mount an effective immune response towards the tumour cell (Thomas and Massague, Cancer Cell, 2005, 8, 369-380). In this way TGF-β in the tumour microenvironment may play a role in immune evasion by cancers. Elevated levels of different TGF-β proteins have been found to be associated with a number of different cancers, including breast, pancreatic and prostate cancers, and mesothelioma and sarcoma (The cancer genome atlas, RNA-seq database as accessed through UCSC) (https://genome-cancer.soe.ucsc.edu—see also Table 2 below). Cancer cells capable of overexpression of TGF-β thus gain a survival advantage, and by targeting CLPTM1, cancers may reduce the activity of NK, macrophages and/or other immune cells and thereby protect themselves from the cellular immune response. Several different targets in the TGF-β signalling pathway have been addressed in order to reduce TGF-β-induced immune suppression (Hanks and Morse, Curr. Opin. Investig. Drugs 2010, 11(12), 1342-53). Furthermore, inhibition of TGF-β signalling has been shown to enhance the efficacy of radiation therapy (Young et al. 2015, Oncoimmunology, 2014, Sep. 14, 4(3) e955696.eCollection 2015).

Accordingly, we now propose a further strategy for inhibiting the effects of TGF-β, in cancers and other conditions associated with TGF-β overexpression or the deleterious effects of TGF-β, as well inhibiting TGF-β-induced immune suppression or immune evasion more generally, by inhibiting the interaction between TGF-β and the receptor CLPTM1, or more particularly by inhibiting the effects of the interaction of TGF-β with CLPTM1.

It is apparent from the discussion above that the implication of TGF-β in a number of conditions provides a rationale for blocking its effects to treat those conditions. Based on our work it is apparent that TGF-β may exert its effects, at least in part through CLPTM1, and that it is therefore desirable to block the interaction between TGF-β and this receptor, particularly where levels of TGF-β are elevated, in order to treat or prevent the medical conditions indicated above, or indeed any condition associated with elevated or unwanted TGF-β levels. Since TGF-β expression is pleiotropic, and TGF-β may have multiple effects, it may in certain cases be beneficial to target the unwanted effects of TGF-β specifically through the CLPTM1 receptor, and thereby minimise or avoid possible side effects.

In particular, we have shown that the CLPTM1 receptor mediates a rapid suppression of key pro-inflammatory cytokines such as IFN and TNF, well known targets inhibited by TGF-β. The cytokines are key components linking the innate system and the adaptive immune system. Furthermore, CLPTM1 is expressed on innate immune cells such as M2 macrophages, T-cells and cancer cells. Blocking CLPTM1, or blocking the effects of TGF-β at the CLPTM1 receptor, can thus offer a novel pharmacological approach in immune-oncology, rendering immune cells less responsive to the suppressive effects of TGF-β 1, 2, 3 in a large number of different human cancers where any of the TGF-β ligands TGF-β 1, 2 or 3 is overexpressed, as well as in other conditions associated with TGF-β overexpression or unwanted TGF-β activity.

We show in Example 1 below that peptides from the extracellular domain (ECD) of CLPTM1 are capable of binding to TGF-β. We thus propose that such peptides, derived from the ECD or comprising sequences with a high degree of sequence identity to the amino acid sequence of the ECD of CLPTM1 may be used specifically to block, or inhibit, the TGF-β-CLPTM1 interaction by binding to TGF-β, thereby sequestering it, and reducing its availability to bind to the receptor. Thus, such peptides represent a first class of therapeutic agents for blocking unwanted or deleterious effects of TGF-β, or TGF-β signalling. Polypeptides based on the ligand binding domains of the CLPTM1 receptor are able to act as 'decoy' receptor molecules ("decoy peptides"), and are able to bind to TGF-β free in the circulation, or associated with ECM and/or stroma, and prevent it from binding to the receptor.

Furthermore, antibodies binding the extracellular domain of CLPTM1 have been shown to be capable of inhibiting TGF-β signalling through the CLPTM1 receptor, and thus such antibodies, or other binding agents capable of binding to the ECD provide an alternative, or further class of agent for blocking, or inhibiting the TGF-β-CLPTM1 interaction. Such binding agents which bind to the extracellular domain of the TGF-β receptor may act to inhibit the binding of TGF-β to the receptor, and therefore block the interaction between TGF-β and the receptor, or they may otherwise inhibit the effect of TGF-β at the receptor.

Together, these data show that the interaction between TGFβ and CLPTM1 may be an attractive new therapeutic target.

Thus, in a first aspect the present invention provides a polypeptide capable of binding to TGF-β for use in treating or preventing a condition associated with elevated or unwanted levels of TGF-β, wherein said polypeptide is capable of inhibiting the interaction of TGF-β with the receptor CLPTM1, and wherein said polypeptide:
(i) has or comprises an amino acid sequence as set forth in SEQ ID NO:2 (extracellular domain of CLPTM1), or an amino acid sequence having at least 75% sequence identity to SEQ ID NO:2; or (ii) is or comprises part of SEQ ID NO: 2, said part comprising at least 6 contiguous amino acids of SEQ ID NO: 2; or (iii) comprises at least 6 amino acids corresponding to at least 6 contiguous amino acids of SEQ ID NO:2 and has at least 75% sequence identity to the equivalent amino acid sequence in SEQ ID NO:2.

In particular the polypeptide is in the form of a fusion protein comprising a said polypeptide fused to a fusion partner.

A further aspect of the present invention provides use of a polypeptide as hereinbefore defined for the manufacture of a medicament for treating or preventing a condition associated with elevated or unwanted levels of TGF-β.

Also provided according to the present invention is a pharmaceutical composition for use in for use in treating or preventing a condition associated with elevated or unwanted levels of TGF-β, said composition comprising a polypeptide as hereinbefore defined together with at least one pharmaceutically-acceptable carrier or excipient, A yet further aspect of the invention provides a kit for use in for use in treating or preventing a condition associated with elevated or unwanted levels of TGF-β, said kit comprising a polypeptide as hereinbefore defined and an immune checkpoint inhibitor.

The components of the kit may be provided, or formulated, for pharmaceutical delivery (i.e. for therapeutic use) and thus may be provided in the form of pharmaceutical compositions containing the polypeptide and/or immune checkpoint inhibitor and one or more pharmaceutically-acceptable carriers or excipients. The components may be formulated or provided for separate administration, including sequentially, or simultaneously.

Accordingly another aspect of the present invention provides a product comprising a polypeptide as hereinbefore defined and an immune checkpoint inhibitor as a combined preparation for separate, sequential or simultaneous use in treating or preventing a condition associated with or unwanted levels of TGF-β.

Also provided is a method of treating or preventing a condition associated with elevated or unwanted levels of TGF-β, which method comprises administering to a subject in need thereof an effective amount of a polypeptide as hereinbefore defined, optionally in combination with an immune checkpoint inhibitor.

In a particular embodiment the condition is a condition associated with elevated or unwanted levels of TGF-β but not with elevated or unwanted levels of GDF15.

In a more particular embodiment, especially in the context of combination therapy with an immune checkpoint inhibitor, the condition is a cancer which is associated with elevated or unwanted levels of TGF-β, especially a cancer which is associated with elevated or unwanted levels of TGF-β but not with elevated or unwanted levels of GDF15.

The invention may also have non-medical uses and accordingly non-therapeutic methods of inhibiting the interaction of TGF-β with the receptor CLPTM1 form a further aspect of the invention. Such a method may involve a contacting a cell or a cell-free system comprising a CLPTM1 receptor and TGF-β with a polypeptide as defined herein. Accordingly, in this aspect the invention provides use of the polypeptide as hereinbefore defined for inhibiting the interaction of TGF-β with the receptor CLPTM1 in vitro.

It will be understood that a polypeptide which binds to TGF-β may act to prevent it from binding to any receptor or protein with which it interacts. By binding to TGF-β, the polypeptide may sequester the TGF-β and reduce its availability to bind to other receptors (i.e. receptors other than CLPTM1), including TGFBR1 and TGFBR2. Thus a polypeptide obtained or derived from CLPTM1 may bind to TGF-β and inhibit its interaction with any receptor and/or otherwise inhibit its activity. It will accordingly be understood that in any aspect disclosed above the polypeptide may be used in the treatment of any condition associated with elevated or unwanted levels of TGF-β, regardless of whether or not the condition is associated with the expression of CLTPM1 on the surface of cells.

Further, in any aspect of the invention presented above and/or disclosed or discussed herein the polypeptide may alternatively be defined as a polypeptide capable of binding to TGF-β wherein said polypeptide:

(i) has or comprises an amino acid sequence as set forth in SEQ ID NO:2 (extracellular domain of CLPTM1), or an amino acid sequence having at least 75% sequence identity to SEQ ID NO:2; or (ii) is or comprises part of SEQ ID NO: 2, said part comprising at least 6 contiguous amino acids of SEQ ID NO: 2; or (iii) comprises at least 6 amino acids corresponding to at least 6 contiguous amino acids of SEQ ID NO:2 and has at least 75% sequence identity to the equivalent amino acid sequence in SEQ ID NO:2.

Thus, in certain embodiments it is not a requirement that the polypeptide is capable of inhibiting the interaction of TGF-β with the receptor CLPTM1, but merely that the polypeptide is capable of binding to TGF-β.

In certain embodiments the polypeptide for use according to the invention does not include the native CLPTM1 receptor itself (more particularly any native or wild-type full length CLPTM1 receptor, from any species). Accordingly, the polypeptide (including the polypeptide provided in fusion proteins as defined herein) may in certain embodiments not include a polypeptide consisting of, or comprising, SEQ ID NO: 1, nor a polypeptide consisting of or comprising an amino acid sequence representing a full length (i.e. intact or entire) native or wild-type CLPTM1 which is a homologue or orthologue of SEQ ID NO: 1, i.e. a receptor from any other species.

It will be seen therefore that as well as the entire or complete extracellular domain, and fragments, or parts, of the extracellular domain of CLPTM1, the polypeptide may be or may comprise a polypeptide having an amino acid sequence which is based on, or derived from the ECD of CLPTM1, or a part thereof, but which is modified with respect to the sequence of the native molecule e.g. by one or more amino acid substitutions, additions and/or deletions. Thus functionally equivalent molecules are included which may have a variant or modified sequence with respect to the native sequence of the ECD or part thereof. By functionally equivalent is meant that the polypeptide retains the ability to bind to TGF-β and inhibit its interaction with the receptor.

In particular, a polypeptide for use according to the invention may be, or may comprise, a polypeptide comprising at least 6 amino acids and may comprise a part of an amino acid sequence as set forth in SEQ ID NO: 2, said part comprising at least 6 contiguous amino acids, or a part of an amino acid sequence which has at least 75% sequence identity to SEQ ID NO: 2, or to a said part. In one embodiment, a part of an amino acid sequence as set forth in SEQ ID NO: 2 comprises at least 6 contiguous amino acids and comprises a deletion of at least 2 contiguous or non-contiguous amino acids with respect to SEQ ID NO: 2.

Analogously, a polypeptide which is a part of an amino acid sequence which has at least 75% sequence identity to any one of SEQ ID NO: 2 may comprise at least 6 contiguous amino acids and a deletion of at least 2 contiguous or non-contiguous amino acids with respect to the functionally equivalent variant sequence corresponding to SEQ ID NO: 2.

Thus parts of SEQ ID NO: 2 may be identified, as described further below, and used as or in polypeptides according to the invention, or polypeptides for use according to the invention may have or comprise an amino acid sequence which has at least 75% sequence identity to any said part, for example as identified below.

Representative or exemplary sequences, representing parts of SEQ ID NO: 2 are listed below, and include for example SEQ ID NOs: 3 to 7, or any of the peptides shown in Example 1 below. A polypeptide for use according to the invention may have or comprise an amino acid sequence which has at least 75% sequence identity to an aforesaid sequence representing a part of SEQ ID NO: 2, or indeed to any peptide described herein, for example in Table 1 or in any of the examples below, which represents a part of SEQ ID NO: 2.

In other representative Examples the polypeptide may comprise a deletion at the N and/or C-terminal end of SEQ ID NO: 2, or of an equivalent sequence, e.g. of a CLPTM1 sequence from another species or of a variant (e.g. a modified sequence) of SEQ ID NO: 2. For example, a portion, or stretch of amino acids at the N-terminal end of SEQ ID NO: 2 may be deleted e.g. up to 103, 104, 105, or 110, or more, amino acids from the N-terminal end of SEQ ID NO: 2. In such an embodiment, amino acids 1-150, 1-140, 1-130, 1-120, 1-115, 1-110, 1-105, 1-104, 1-103, 1-102, 1-101, 1-100, 1-95, 1-90, 1-85, 1-80, 1-75, 1-70, or fewer amino acids, may be deleted from the N-terminal of SEQ ID NO: 2. In addition, or alternatively the polypeptide may comprise a deletion at the C-terminal end. Thus, for example 1-150, 1-140, 1-130, 1-120, 1-115, 1-110, 1-105, 1-104, 1-103, 1-102, 1-101, 1-100, 1-95, 1-90, 1-85, 1-80, 1-75, 1-70, or fewer amino acids from the C-terminal end may be deleted alternatively or additionally to an N-terminal deletion. In an embodiment a deletion of from 1 up to 110, e.g. from 1 up to 105, 104, 103, 102, 101 or 100 amino acids at the N-terminal end of SEQ NO: 2 may be combined with a deletion of 1-10, e.g. 1-8, 1-6, 1-4, 1-3 or 1-2 amino acids from the C-terminal end. A representative example of such an N and C-terminal truncated sequence is shown in SEQ ID NO: 243. In other representative examples, as noted above and below, longer parts of the sequence may be removed or deleted, e.g. longer truncations from the N- and/or C-terminal ends, or indeed fragments of the ECD of CLPTM1 may be used, from any part of the ECD sequence.

The term "TGF-β" as used herein includes any TGF-β molecule, and in particular includes the three isoforms TGF-β1, 2 and 3. The term may be taken to include any molecule classified as a TGF-β molecule. Further, although the focus in this invention is on human TGF-β, the therapeutic uses and methods are not limited to humans and hence the term may include TGF-β proteins from any species. In a particular embodiment the term refers to the three isoforms TGF-β1, 2 and/or 3. In a still more particular embodiment the term refers to human TGF-β1, 2 and/or 3.

Conditions associated with elevated or unwanted levels of TGF-β, including those which are not associated with elevated or unwanted levels of GDF15, are described in more detail below, but in certain preferred embodiments include cancer, fibrosis and fibrotic diseases, inflammatory conditions, immunosuppression, and infections.

An "elevated" level may be a level which is increased relative to a subject without the condition, or relative to a level present in a part of the body of the subject which is not affected by the condition. It may be a level which is higher than that of a healthy, normal subject, and in particular it may be higher, or increased, compared to the level present at a particular site, e.g., in the circulation, or at a particular site or location in the body, e.g. of the normal or healthy subject. For example the level may be elevated at a site of infection or fibrosis, or at the site of a tumour, as compared to elsewhere in the body of a subject, or compared to a level at that body site in a healthy or normal subject. An elevated level of TGF-β thus includes overexpression of TGF-β. An "unwanted" level may be a level which is causing a harmful or deleterious effect on or to the subject.

The term "polypeptide" is used broadly herein to include peptide, polypeptide or protein molecules, including any proteinaceous molecule which may include other chemical groups or moieties, e.g. as long as there is a protein/peptide/polypeptide part. As noted above, a polypeptide for use according to the invention comprises at least 6 amino acid residues.

The term "inhibit" includes reducing as well as preventing, and thus includes any effect in reducing, decreasing or lowering the stated activity or property, e.g. the interaction of TGF-β with the receptor, or any therapeutic, biological or physiological effect or activity discussed herein. Thus, alternatively expressed, the polypeptide may block the interaction of TGF-β with the receptor, but this does not necessarily entail or require a complete blocking of receptor binding and/or function, merely a reduction. By way of representative example, binding of TGF-β to the receptor, and/or any effect or aspect of receptor function resulting from or induced or stimulated by such binding, may be reduced by 20, 30, 40, 50, 60 or 70% or more compared to the binding and/or receptor activity or function seen in the absence of the polypeptide. Thus, it will be seen that the effect of the TGF-β at the receptor may be inhibited, whether or not binding of TGF-β to the receptor is inhibited. Accordingly, a polypeptide may inhibit the interaction of TGF-β with the receptor, or the effect of the interaction, with or without inhibiting binding of TGF-β to the receptor.

The term "interaction" includes binding of TGF-β to the receptor, and/or stimulation or induction of receptor activity or any effect at the receptor. Thus, inhibiting the interaction of TGF-β with the receptor CLPTM1 includes inhibiting an effect of (i.e. resulting from) binding of TGF-β to the receptor, without necessarily, as indicated above, inhibiting binding of TGF-β to the receptor.

Binding of TGF-β to a receptor may be assessed or determined using known ligand binding assays as widely described and reported in the literature, including a binding assay as described in the Examples below. The effect of TGF-β binding on a receptor, or more particularly the effect of a polypeptide of the invention on TGF-β binding to a receptor may be assessed or determined by determining or assessing any effect resulting from or induced or stimulated by binding of TGF-β and/or a polypeptide of the invention to the receptor. Any aspect of receptor activity may also be assessed or determined in the presence of TGF-β and the presence or absence of a polypeptide of the invention, e.g. a reduction of the immunosuppressive effect of TGF-β may be assessed or determined by determining the extent or amount of cell-mediated cytotoxicity exhibited by an immune cell (e.g. an NK cell or macrophage) expressing a receptor. Alternatively, other aspects of signalling resulting from receptor stimulation by TGF-β may be assessed and compared in the presence or absence of the polypeptide of the invention.

The term "treating" is used broadly herein to include any aspect of improving or ameliorating a condition or the clinical status of a subject suffering from or having the condition. Thus, a complete cure of the condition is not required and "treating" includes improving any aspect, parameter or symptom of a condition.

Similarly, the term "preventing" is used broadly herein to include any aspect of reducing or delaying a condition, or the onset or progression of a condition. Thus preventing does not require complete or absolute prevention of the development of a condition and may include delaying or slowing the progression or onset of any aspect, symptom or parameter of a condition. The severity of a symptom, parameter or aspect may be reduced and/or it may be delayed in developing. In a particular embodiment, preventing may include preventing or reducing (i.e. inhibiting) metastasis of a cancer. In other embodiments the progression or development of one or more symptoms or aspects of a condition may be delayed, or reduced or indeed prevented from developing.

As noted above, a polypeptide for use according to the invention is or comprises a part which is based on the extracellular domain (ECD) of the receptor and can include sequence variants of the native ECD, as well as fragments or parts thereof (including sequence variants of parts of the ECD).

As noted above, in representative embodiments a polypeptide of the invention may have or comprise a sequence representing or corresponding to part of the ECD sequences of SEQ ID NO. 2. Such a sequence may have at least 75% sequence identity to a part of SEQ ID NO. 2, including for example any one of SEQ ID NO: 5 (YISEHEHFTDFNATSALFWEQHDLVYGDWTS), SEQ ID NO: 6 (ALFWEQHDLVYGDWTS), SEQ ID NO: 3 (YISEHEH), or SEQ ID NO: 4 (LFWEQH), representing sequences derived from the ECD of CLPTM1.

In a particular embodiment, the polypeptide may comprise a sequence as set forth in SEQ ID NO: 3 (YISEHEH) or a sequence having at least 75% sequence identity thereto and a sequence as set forth in SEQ ID NO: 4 (LFWEQH) or a sequence having at least 75% sequence identity thereto.

Other representative polypeptides may have or comprise an amino acid sequence as set out in Table 1 below, or Table 2 in Example 1, or a sequence having at least 75% sequence identity to any such sequence, or, where applicable, a sequence which is a part of any such sequence, wherein said part comprises at least 6 contiguous amino acids.

TABLE 1

| Sequence number | Polypeptide sequence |
| --- | --- |
| SEQ ID NO: 43 | YISEHEHFTDFNATSALFWEQHDLVYGDWT |
| SEQ ID NO: 44 | YISEHEHFTDFNATSALFWEQHDLVYGDW |
| SEQ ID NO: 45 | YISEHEHFTDFNATSALFWEQHDLVYGD |
| SEQ ID NO: 46 | YISEHEHFTDFNATSALFWEQHDLVYG |
| SEQ ID NO: 47 | YISEHEHFTDFNATSALFWEQHDLVY |
| SEQ ID NO: 48 | YISEHEHFTDFNATSALFWEQHDLV |
| SEQ ID NO: 49 | YISEHEHFTDFNATSALFWEQHDL |
| SEQ ID NO: 50 | YISEHEHFTDFNATSALFWEQHD |
| SEQ ID NO: 51 | YISEHEHFTDFNATSALFWEQH |
| SEQ ID NO: 52 | YISEHEHFTDFNATSALFWEQ |
| SEQ ID NO: 53 | YISEHEHFTDFNATSALFWE |
| SEQ ID NO: 54 | YISEHEHFTDFNATSALFW |
| SEQ ID NO: 55 | YISEHEHFTDFNATSALF |
| SEQ ID NO: 56 | YISEHEHFTDFNATSAL |
| SEQ ID NO: 57 | YISEHEHFTDFNATSA |
| SEQ ID NO: 58 | YISEHEHFTDFNATS |
| SEQ ID NO: 59 | YISEHEHFTDFNAT |
| SEQ ID NO: 60 | YISEHEHFTDFNA |
| SEQ ID NO: 61 | YISEHEHFTDFN |
| SEQ ID NO: 62 | YISEHEHFTDF |
| SEQ ID NO: 63 | YISEHEHFTD |
| SEQ ID NO: 64 | YISEHEHFT |

TABLE 1-continued

| Sequence number | Polypeptide sequence |
| --- | --- |
| SEQ ID NO: 65 | YISEHEHF |
| SEQ ID NO: 66 | ISEHEHFTDFNATSALFWEQHDLVYGDWTS |
| SEQ ID NO: 67 | SEHEHFTDFNATSALFWEQHDLVYGDWTS |
| SEQ ID NO: 68 | EHEHFTDFNATSALFWEQHDLVYGDWTS |
| SEQ ID NO: 69 | HEHFTDFNATSALFWEQHDLVYGDWTS |
| SEQ ID NO: 70 | EHFTDFNATSALFWEQHDLVYGDWTS |
| SEQ ID NO: 71 | HFTDFNATSALFWEQHDLVYGDWTS |
| SEQ ID NO: 72 | FTDFNATSALFWEQHDLVYGDWTS |
| SEQ ID NO: 73 | TDFNATSALFWEQHDLVYGDWTS |
| SEQ ID NO: 74 | DFNATSALFWEQHDLVYGDWTS |
| SEQ ID NO: 75 | FNATSALFWEQHDLVYGDWTS |
| SEQ ID NO: 76 | NATSALFWEQHDLVYGDWTS |
| SEQ ID NO: 77 | ATSALFWEQHDLVYGDWTS |
| SEQ ID NO: 78 | TSALFWEQHDLVYGDWTS |
| SEQ ID NO: 79 | SALFWEQHDLVYGDWTS |
| SEQ ID NO: 80 | ALFWEQHDLVYGDWTS |
| SEQ ID NO: 81 | LFWEQHDLVYGDWTS |
| SEQ ID NO: 82 | LFWEQHDLVYGDWT |
| SEQ ID NO: 83 | LFWEQHDLVYGDW |
| SEQ ID NO: 84 | LFWEQHDLVYGD |
| SEQ ID NO: 85 | LFWEQHDLVYG |
| SEQ ID NO: 86 | LFWEQHDLVY |
| SEQ ID NO: 87 | LFWEQHDLV |
| SEQ ID NO: 88 | LFWEQHDL |
| SEQ ID NO: 89 | LFWEQHD |
| SEQ ID NO: 90 | FTDFNATSALFWEQH |
| SEQ ID NO: 91 | TDFNATSALFWEQHD |
| SEQ ID NO: 92 | DFNATSALFWEQHDL |
| SEQ ID NO: 93 | FNATSALFWEQHDLV |
| SEQ ID NO: 94 | NATSALFWEQHDLVY |
| SEQ ID NO: 95 | ATSALFWEQHDLVYG |
| SEQ ID NO: 96 | TSALFWEQHDLVYGD |
| SEQ ID NO: 97 | SALFWEQHDLVYGDW |
| SEQ ID NO: 98 | ALFWEQHDLVYGDWT |
| SEQ ID NO: 99 | ISEHEHFTDFNATSALFWEQH |
| SEQ ID NO: 100 | SEHEHFTDFNATSALFWEQH |
| SEQ ID NO: 101 | EHEHFTDFNATSALFWEQH |
| SEQ ID NO: 102 | HEHFTDFNATSALFWEQH |
| SEQ ID NO: 103 | EHFTDFNATSALFWEQH |

TABLE 1-continued

| Sequence number | Polypeptide sequence |
|---|---|
| SEQ ID NO: 104 | HFTDFNATSALFWEQH |
| SEQ ID NO: 105 | FTDFNATSALFWEQH |
| SEQ ID NO: 106 | TDFNATSALFWEQH |
| SEQ ID NO: 107 | DFNATSALFWEQH |
| SEQ ID NO: 108 | FNATSALFWEQH |
| SEQ ID NO: 109 | NATSALFWEQH |
| SEQ ID NO: 110 | ATSALFWEQH |
| SEQ ID NO: 111 | SALFWEQH |
| SEQ ID NO: 112 | ALFWEQH |
| SEQ ID NO: 113 | ISEHEHFTDFNATSALFWEQHD |
| SEQ ID NO: 114 | SEHEHFTDFNATSALFWEQHDL |
| SEQ ID NO: 115 | EHEHFTDFNATSALFWEQHDLV |
| SEQ ID NO: 116 | HEHFTDFNATSALFWEQHDLVY |
| SEQ ID NO: 117 | EHFTDFNATSALFWEQHDLVYG |
| SEQ ID NO: 118 | HFTDFNATSALFWEQHDLVYGD |
| SEQ ID NO: 119 | FTDFNATSALFWEQHDLVYGDW |
| SEQ ID NO: 120 | TDFNATSALFWEQHDLVYGDWT |
| SEQ ID NO: 121 | DFNATSALFWEQHDLVYGDWTS |
| SEQ ID NO: 122 | SALFWEQHDLVYGDW |
| SEQ ID NO: 123 | TSALFWEQHDLVYGD |
| SEQ ID NO: 124 | ATSALFWEQHDLVYG |
| SEQ ID NO: 125 | NATSALFWEQHDLVY |
| SEQ ID NO: 126 | FNATSALFWEQHDLV |
| SEQ ID NO: 127 | DFNATSALFWEQHDL |
| SEQ ID NO: 128 | TDFNATSALFWEQHD |
| SEQ ID NO: 129 | FTDFNATSALFWEQH |
| SEQ ID NO: 130 | SALFWEQHDLVYGDWT |
| SEQ ID NO: 131 | FNATSALFWEQHDLVYGDWTSGEN |
| SEQ ID NO: 132 | FNATSALFWEQHDLVYGDWTSGE |
| SEQ ID NO: 133 | FNATSALFWEQHDLVYGDWTSG |
| SEQ ID NO: 134 | FNATSALFWEQHDLVYGDWTS |
| SEQ ID NO: 135 | FNATSALFWEQHDLVYGDWT |
| SEQ ID NO: 136 | NATSALFWEQHDLVYGDWTSGEN |
| SEQ ID NO: 137 | ATSALFWEQHDLVYGDWTSGEN |
| SEQ ID NO: 138 | TSALFWEQHDLVYGDWTSGEN |
| SEQ ID NO: 139 | SALFWEQHDLVYGDWTSGEN |
| SEQ ID NO: 140 | YFNDYWNLQ |
| SEQ ID NO: 141 | YPIIYFNDYWNLQKDYY |

TABLE 1-continued

| Sequence number | Polypeptide sequence |
| --- | --- |
| SEQ ID NO: 142 | YPIIYFNDYWNLQKDY |
| SEQ ID NO: 143 | YPIIYFNDYWNLQKD |
| SEQ ID NO: 144 | YPIIYFNDYWNLQK |
| SEQ ID NO: 145 | YPIIYFNDYWNLQ |
| SEQ ID NO: 146 | PIIYFNDYWNLQKDYY |
| SEQ ID NO: 147 | IIYFNDYWNLQKDYY |
| SEQ ID NO: 148 | IYFNDYWNLQKDYY |
| SEQ ID NO: 149 | YFNDYWNLQKDYY |
| SEQ ID NO: 150 | WTS |
| SEQ ID NO: 151 | PKDT |
| SEQ ID NO: 152 | APRVASRNLFPKDT |
| SEQ ID NO: 153 | PRVASRNLFPKDT |
| SEQ ID NO: 154 | RVASRNLFPKDT |
| SEQ ID NO: 155 | VASRNLFPKDT |
| SEQ ID NO: 156 | ASRNLFPKDT |
| SEQ ID NO: 157 | SRNLFPKDT |
| SEQ ID NO: 158 | RNLFPKDT |
| SEQ ID NO: 159 | NLFPKDT |
| SEQ ID NO: 160 | LFPKDT |
| SEQ ID NO: 161 | FPKDT |
| SEQ ID NO: 162 | PRVASRNLFPKDTL |
| SEQ ID NO: 163 | VASRNLFPKDTLM |
| SEQ ID NO: 164 | ASRNLFPKDTLMN |
| SEQ ID NO: 165 | SRNLFPKDTLMNL |
| SEQ ID NO: 166 | RNLFPKDTLMNLH |
| SEQ ID NO: 167 | NLFPKDTLMNLHV |
| SEQ ID NO: 168 | LFPKDTLMNLHVY |
| SEQ ID NO: 169 | FPKDTLMNLHVYI |
| SEQ ID NO: 170 | PKDTLMNLHVYIS |
| SEQ ID NO: 171 | PKDTLMNLHVYI |
| SEQ ID NO: 172 | PKDTLMNLHVY |
| SEQ ID NO: 173 | PKDTLMNLHV |
| SEQ ID NO: 174 | PKDTLMNLH |
| SEQ ID NO: 175 | PKDTLMNL |
| SEQ ID NO: 176 | PKDTLMN |
| SEQ ID NO: 177 | PKDTLM |
| SEQ ID NO: 178 | PKDTL |
| SEQ ID NO: 179 | AAAQEADGARSAVVAAGGGSG |
| SEQ ID NO: 180 | SGQVTSNGSIGRDPPAETQPG |

TABLE 1-continued

| Sequence number | Polypeptide sequence |
| --- | --- |
| SEQ ID NO: 181 | QNPPAQPAPNAWQVIKGVLFG |
| SEQ ID NO: 182 | RIFIIWAISSWFRRGPAPQDG |
| SEQ ID NO: 183 | QAGPGGAPRVASRNLFPKDTG |
| SEQ ID NO: 184 | LMNLHVYISEHEHFTDFNATG |
| SEQ ID NO: 185 | SALFWEQHDLVYGDWTSGENG |
| SEQ ID NO: 186 | SDGCYEHFAELDIPQSVQQNG |
| SEQ ID NO: 187 | GSIYIHVYFTKSGFHPDPRQG |
| SEQ ID NO: 188 | KALYRRLATVHMSRMINKYKG |
| SEQ ID NO: 189 | RRRFQKTKNLLTGETEADPEG |
| SEQ ID NO: 190 | MIKRAEDYGPVEVISHWHPNG |
| SEQ ID NO: 191 | ITINIVDDHTPWVKGSVPPPG |
| SEQ ID NO: 192 | LDQYVKFDAVSGDYYPIIYFG |
| SEQ ID NO: 193 | NDYWNLQKDYYPINESLASLG |
| SEQ ID NO: 194 | PLRVSFCPLSLWRWQLYAAQG |
| SEQ ID NO: 195 | STKSPWNFLGDELYEQSDEEG |
| SEQ ID NO: 196 | YEQSDEEQDSVKVALLETNPG |
| SEQ ID NO: 197 | LWRWQLYAAQSTKSPWNFLGG |
| SEQ ID NO: 198 | YPINESLASLPLRVSFCPLSG |
| SEQ ID NO: 199 | GDYYPIIYFNDYWNLQKDYYG |
| SEQ ID NO: 200 | WQVIKGVLFRIFIIWAISSWG |
| SEQ ID NO: 201 | RNLFPKDTLMNLHVYISEHEG |
| SEQ ID NO: 202 | FTDFNATSALFWEQHDLVYGG |
| SEQ ID NO: 203 | AAAQEADGARSAVVAAGGGS |
| SEQ ID NO: 204 | SGQVTSNGSIGRDPPAETQP |
| SEQ ID NO: 205 | QNPPAQPAPNAWQVIKGVLF |
| SEQ ID NO: 206 | RIFIIWAISSWFRRGPAPQD |
| SEQ ID NO: 207 | QAGPGGAPRVASRNLFPKDT |
| SEQ ID NO: 208 | LMNLHVYISEHEHFTDFNAT |
| SEQ ID NO: 209 | SALFWEQHDLVYGDWTSGEN |
| SEQ ID NO: 210 | SDGCYEHFAELDIPQSVQQN |
| SEQ ID NO: 211 | GSIYIHVYFTKSGFHPDPRQ |
| SEQ ID NO: 212 | KALYRRLATVHMSRMINKYK |
| SEQ ID NO: 213 | RRRFQKTKNLLTGETEADPE |
| SEQ ID NO: 214 | MIKRAEDYGPVEVISHWHPN |
| SEQ ID NO: 215 | ITINIVDDHTPWVKGSVPPP |
| SEQ ID NO: 216 | LDQYVKFDAVSGDYYPIIYF |
| SEQ ID NO: 217 | NDYWNLQKDYYPINESLASL |
| SEQ ID NO: 218 | PLRVSFCPLSLWRWQLYAAQ |

TABLE 1-continued

| Sequence number | Polypeptide sequence |
|---|---|
| SEQ ID NO: 219 | STKSPWNFLGDELYEQSDEE |
| SEQ ID NO: 220 | YEQSDEEQDSVKVALLETNP |
| SEQ ID NO: 221 | LWRWQLYAAQSTKSPWNFLG |
| SEQ ID NO: 222 | YPINESLASLPLRVSFCPLS |
| SEQ ID NO: 223 | GDYYPIIYFNDYWNLQKDYY |
| SEQ ID NO: 224 | WQVIKGVLFRIFIIWAISSW |
| SEQ ID NO: 225 | RNLFPKDTLMNLHVYISEHE |
| SEQ ID NO: 226 | FTDFNATSALFWEQHDLVYG |
| SEQ ID NO: 230 | GGAPRVASRNLFPKD |
| SEQ ID NO: 231 | RVASRNLFPKDTLMN |
| SEQ ID NO: 232 | RNLFPKDTLMNLHVY |
| SEQ ID NO: 233 | PKDTLMNLHVYISEH |
| SEQ ID NO: 234 | LDQYVKFDAVSGDYY |
| SEQ ID NO: 235 | VKFDAVSGDYYPIIY |
| SEQ ID NO: 236 | AVSGDYYPIIYFNDY |
| SEQ ID NO: 237 | DYYPIIYFNDYWNLQ |
| SEQ ID NO: 238 | IIYFNDYWNLQKDYY |
| SEQ ID NO: 239 | NDYWNLQKDYYPINE |
| SEQ ID NO: 240 | NLQKDYYPINESLAS |
| SEQ ID NO: 241 | QKALYRRLATVHM |
| SEQ ID NO: 242 | QKALYRRLATVHMC |
| SEQ ID NO: 243 | NLHVYISEHEHFTDFNATSALFWEQHDLVYGDWTSGENSDGC YEHFAELDIPQSVQQNGSIYIHVYFTKSGFHPDPRQKALYRRLA TVHMSRMINKYKAVGFQKTKNLLTGETEADPEMIKRAEDYGPV EVISHWHPNITINIVDDHTPWVKGSVPPPLDQYVKFDAVSGDYY PIIYFNDYWNLQKDYYPINESLASLPLRVSFCPLSLWRWQLYAA QSTKSPWNFLGDELYEQSDEEQDSVKVALLET |

The present invention accordingly provides therapeutic agents (polypeptides) which are capable of reducing the activity, or the effect, of TGF-β in a subject by blocking the interaction between TGF-β and the CLPTM1 receptor. Such agents are or comprise polypeptides which are selected from the group consisting of all or portions, particularly soluble portions, of the extracellular domain of receptor CLPTM1, or polypeptides which are based on, or derived, from the ECD or portions thereof.

A polypeptide having a high degree of sequence identity with all or a portion of an extracellular domain of CLPTM1 may be said to be 'based on' or 'derived from' or to have or comprise a sequence that is 'based on' or 'derived from' an extracellular domain of the receptor. Such polypeptides may thus comprise or have a sequence which corresponds to an ECD or part thereof, but which includes some sequence variation or modification, as compared to the native human ECD sequences as set out in SEQ ID NO. 2. A "corresponding" sequence may thus be correlated to, or aligned with, a sequence contained within the ECD of SEQ ID NO. 2 (i.e. to or with a part of a said sequence), but may contain one more sequence variations with respect to a said sequence.

A polypeptide for use according to the invention is or comprises a polypeptide derived from the CLPTM1 receptor, which may include variants, or homologues, obtained or derived from CLPTM1 receptors from other species. Thus the polypeptide may be derived from or based on the ECD of the equivalent or corresponding receptor from other species, particularly other mammalian species, e.g. dog or mouse.

In certain preferred embodiments, the polypeptides do not comprise amino acid sequences derived or obtained from the receptor (i.e. amino acid sequences corresponding to receptor sequences) that do not form part of the extracellular domain of the receptor protein, i.e. which amino acid sequences which form the transmembrane and/or intracellular domains of the receptor protein. Specifically, in preferred embodiments, polypeptides derived from CLPTM1 may not comprise the residues (amino acid sequences) C-terminal to the extracellular domain of CLPTM1, or part thereof (i.e. residues/sequences within SEQ ID NO: 1 that are C-terminal to the sequence represented by SEQ ID NO: 2 or part thereof). Thus, in certain embodiments, the polypeptide does not comprise amino acids 355-669 of SEQ ID NO: 1.

In certain embodiments of any of the various aspects of the invention, the polypeptides do not consist of or comprise an amino acid sequence representing an entire native extracellular domain. That is, in such embodiments the polypeptide does not consist of, or a fusion protein does not comprise, the ECD of CLPTM1. Accordingly in one such embodiment the polypeptide does not consist of or does not comprise the sequence of SEQ ID NO.2 (i.e. the entire sequence of SEQ ID NO: 2). However, in another embodiment the polypeptide does consist of, or comprises, the sequence of SEQ ID NO.2. In other embodiments the polypeptide may comprise the entire native extracellular domain together with one or more additional amino acid sequences which are not derived from, or do not correspond to, CLPTM1 sequences. In other words the polypeptide may consist of the ECD of CLPTM1 (or indeed a part of any such ECD) together with one or more amino acid sequences which are not sequences from a native CLPTM1 receptor, or more particularly which are not sequences which flank, or are immediately adjacent to, the ECD in the native receptor. The additional amino acid sequence may in this respect comprise 2 or more amino acids. It will be seen that in such embodiments the polypeptides do not contain any amino acid sequences derived from or corresponding to a native/wild-type CLPTM1 receptor, other than the sequences derived from or corresponding to the ECD of CLPTM1 or a part thereof.

Accordingly, in certain embodiments, wherein the polypeptide comprises an ECD or a part thereof as part of a longer amino acid sequence (e.g. a fusion protein), the sequence of the ECD or part thereof may be comprised in a "non-native" sequence context; i.e. the sequence flanking on one or both sides the amino acid sequence which corresponds to the ECD or part thereof is not a sequence which flanks the sequence of the ECD or part thereof (e.g. SEQ ID NO:2 or a part thereof) in the native full length receptor from which the ECD or part thereof is obtained or derived, or to which it corresponds (e.g. in SEQ ID NO: 1 (full-length CLPTM1)). Thus, in certain embodiments, at least 2, 3, 4, 5, 6 or 7 contiguous amino acids flanking (C-terminal) to SEQ ID NO: 2 are not from SEQ ID NO: 1. It will be understood by this that the flanking amino acids are not those immediately adjacent to the extracellular domain defined by SEQ ID NO: 2 in SEQ ID NO: 1.

In yet further embodiments of any of the various aspects of the invention, the polypeptide may be (i.e. may consist of) or may comprise a part of the ECD of CLPTM1. In particular embodiments such a part may represent a deletion of at least 2 contiguous or non-contiguous amino acids from the ECD. Thus, in representative embodiments a polypeptide according to the invention may consist of or may comprise an amino acid sequence corresponding to, or represented by, SEQ ID NO: 2 with a deletion of more than one (i.e. 2, 3, 4, 5, 6, 7, 8, 9, 10, 15, 10, 20, 30, 40, 50, 60, 70, 80, 90, 100, 105, 110 or more) amino acids (which may be contiguous or non-contiguous). In other words, the deleted amino acids may be found at the N-terminus and/or C-terminus of the SEQ ID NO: 2.

Accordingly, in one particular embodiment, the polypeptide for use according to the invention:

(i) comprises an amino acid sequence as set forth in SEQ ID NO:2 (extracellular domain of CLPTM1) wherein the amino acid sequence is not flanked at either or both ends by an amino acid sequence which flanks the said amino acid sequence in a native CLPTM1 receptor, or comprises an amino acid sequence which is not the amino acid sequence of SEQ ID NO: 2 but which has at least 75% sequence identity to SEQ ID NO:2, wherein optionally the amino acid sequence is not flanked at either or both ends by an amino acid sequence which flanks the said amino acid sequence in a native CLPTM1 receptor; or (ii) is or comprises a part of SEQ ID NO:2, said part comprising at least 6 contiguous amino acids of SEQ ID NO:2, wherein (i) at least 2 contiguous or non-contiguous amino acids of SEQ ID NO:2 are deleted and/or (ii) said part is not flanked at either or both ends by an amino acid sequence which flanks the said amino acid sequence in a native CLPTM1 receptor; or (iii) comprises an amino acid sequence having at least 6 amino acids corresponding to at least 6 contiguous amino acids of 2 and has at least 75% sequence identity to the equivalent amino acid sequence in SEQ ID NO:2, wherein (i) at least 2 contiguous or non-contiguous amino acids of SEQ ID NO:2 are deleted and/or (ii) the amino acid sequence corresponding to SEQ ID NO:2 is not flanked at either or both ends by an amino acid sequence which flanks the said amino acid sequence in a native CLPTM1 receptor.

In a particular embodiment a polypeptide may have or comprise a sequence as set forth in SEQ ID NO: 5 or 6. It is believed that receptor CLPTM1 may comprise more than one binding site for TGF-β, and in particular at least two binding sites for TGF-β. Thus, TGF-β may have at least two contact points within the CLPTM1 receptor, or more particularly the ECD thereof. Further the TGF-β binding sites may overlap, fully or partially, the binding sites for GDF15, for example as identified and described in WO 2017/013188 (PCT/EP2016/067338). Also, the binding sites for the different particular TGF-β cytokines (e.g. TGF-β 1, 2 or 3) may differ, and may be partially or fully overlapping. Our results, shown in Example 1 below, show that different peptides derived from the CLPTM1 ECD may bind the different TGF-β cytokines to different extents. Thus, polypeptides may be selected or designed to bind one or more of the particular TGF-β 1, 2 or 3 cytokines to a greater or lesser extent. In this way the interaction of all TGF-β cytokines, or a subset thereof, or any one specific TGF-β cytokine, with CLPTM1 may be inhibited.

By way of one representative Example it is proposed that two binding sites, or contact points, for TGF-β may lie in SEQ ID NO.5, representing amino acids 108 to 138 of SEQ ID NO: 2 (the ECD of human CLPTM1). These are provided as SEQ ID NOs: 3 (YISEHEH) and 4 (LFWEQH), which represent or comprise or constitute a part of these binding sites. A representative polypeptide of the invention may comprise a sequence corresponding to, or based on or derived from one or both of these sequences. A representative polypeptide including both binding sites has or comprises SEQ ID NO: 5 or a sequence having at least 75% sequence identity thereto. Representative polypeptides of the invention also include a polypeptide having or comprising a sequence as set forth in SEQ NO:6, representing amino acids 123 to 138 of SE ID NO:2, which includes one putative binding site, or the related polypeptide of SEQ ID NO:7 (GALFWEQHDLVYGDWTS).

Further work has suggested that TGF-β may have other or additional binding sites in CLPTM1. One such additional binding site may be represented by or may comprise SEQ ID NO: 140 (YFNDYWNLQ). A representative polypeptide of the invention may comprise a sequence corresponding to, or based on or derived from this sequence. A representative polypeptide accordingly has or comprises SEQ ID NO:140, or a sequence having at least 75% sequence identity thereto, for example the polypeptide may have or comprise any one of SEQ ID NOs:141 to 149, or a sequence having at least 75% sequence identity thereto.

Binding of TGF-β to a number of polypeptides derived from CLPTM1 was tested in an ELISA assay in Example 1. A number of polypeptides were found to bind to TGF-β proteins, and thus these, or peptides based on or derived from them may represent preferred polypeptides for use in the present invention. Thus, a polypeptide having or comprising a sequence as set forth in any one of SEQ ID NOs:187, 188, 190, 191, 192, 198, 199, 211, 212, 214, 215, 216, 222, 223, or a sequence having at least 75% identity thereto, represent preferred polypeptides of the various aspects of the present invention. It will be noted in this respect that SEQ ID NOs: 211, 212, 215, 216, 222 and 223 represent polypeptides corresponding to SEQ ID NOs: 187, 188, 190, 191, 192, 198, 199 but lacking the C-terminal glycine (G) residue, which is not found in native CLPTM1.

More particularly, the results of Example 1 show binding of peptides 14 and 21, and also peptides 10 and 20 of Table 3 (corresponding to SEQ ID NOs: 21 and 28, and 17 and 27) to TGF-β proteins. Accordingly, a polypeptide having or comprising a sequence as set forth in any one of SEQ ID NOs: 17, 21, 27 and 28, or SEQ ID NOs: 212, 216, 222 and 223 or a sequence having at least 75% identity thereto, represent preferred polypeptides for use according to the present invention.

Polypeptides of SEQ ID NOs: 21 and 28 comprise a DYPPI (SEQ ID NO. 41) sequence motif. It is believed that peptides comprising such a motif, or at least a part thereof, may represent a class of useful polypeptides according to the present invention.

Further work, also reported in Example 1, using longer peptides (peptides 25-33 (also designated herein as peptides GT1-GT9) and having SEQ ID NOs: 32-40) has also shown that favourable binding to TGF-β may be obtained with peptides comprising two DYPPI (SEQ ID NO. 41) sequence motifs. Particular mention may be made of the peptides of SEQ ID NOs: 32 (peptide 25/GT1); 38 (peptide 31/GT7); 39 (peptide 32/GT8) and 40 (peptide 33/GT9), all of which contain two DYPPI (SEQ ID NO. 41) sequence motifs. However, mention may also be made of the peptide of SEQ ID NO: 36 (peptide 29/GT5) which overlaps with the peptides of SEQ ID NOs: 3 to 7 and also binds to TGF-β proteins. Further, binding has also been observed with the peptide of SEQ ID NO: 37 (peptide 30/GT6), although presently it is believed that the peptides of SEQ ID NOs: 32, 36 and 38-40 represent more promising polypeptides for use according to the invention.

Accordingly, a further group of polypeptides preferred for use according to the invention are polypeptides having or comprising a sequence as set forth in any one of SEQ ID NOs: 32, and 36-40, or more particularly SEQ ID NOs: 32, 36 and 38-40, or a sequence having at least 75% identity thereto.

The peptides of SEQ ID NOs: 32 to 40 represent novel previously undisclosed polypeptides. Polypeptides having or comprising such sequences therefore represent a further aspect of the present invention.

Accordingly, in another aspect the invention also provides a polypeptide having or comprising a sequence as set forth in any one of SEQ ID NOs: 32, and 36-40, or more particularly SEQ ID NOs: 32, 36 and 38-40, or a sequence having at least 90 or 95% sequence identity thereto, wherein where the polypeptide comprises a said sequence, the sequence is not flanked at either or both ends by an amino acid sequence which flanks the said sequence in a native CLPTM1 receptor. More particularly, the sequence is not flanked at either or both ends by an amino acid sequence which flanks the said sequence in SEQ ID NO: 2.

It will thus be seen that such polypeptides do not include polypeptides comprising longer sequences from the CLPTM1 ECD, but do include longer polypeptides which comprise the said sequence fused, or linked, to a non-CLPTM1 amino acid sequence, e.g. as a fusion protein. Thus, a polypeptide may consist of a sequence as set forth in any one of SEQ ID NOs: 32, and 36-40, or more particularly SEQ ID NOs: 32, 36 and 38-40, or a sequence having at least 90 or 95% sequence identity thereto, or it may comprise such a sequence together with one or more additional amino acid sequences which are not derived from, or do not correspond to, CLPTM1 sequences. In other words the polypeptide may consist of the sequence together with one or more amino acid sequences which are not sequences from a native CLPTM1 receptor, or more particularly which are not sequences which flank, or are immediately adjacent to, the sequence in the native receptor. The additional amino acid sequence may in this respect comprise 2 or more amino acids, In a preferred embodiment of this aspect the polypeptide comprises at least one, and more preferably at least two DYPPI (SEQ ID NO. 41) sequence motifs, or parts thereof. For example the polypeptide may comprise at least one DYPPI (SEQ ID NO. 41) sequence motif, and at least a part of a second DYPPI (SEQ ID NO. 41) sequence motif.

In a further particular embodiment a polypeptide having or comprising, or based on or derived from (e.g. a part thereof comprising at least 6 contiguous amino acids or a sequence having at least 75% sequence identity to), the amino acid sequence set out in SEQ ID NO: 28 (namely the sequence GDYYPIIYFNDYWNLQKDYYG) or SEQ ID NO: 42 (namely the sequence GDYYPIIYFN-DYWNLQKDYY, i.e. SEQ ID NO: 28 lacking the C-terminal G residue which is not present in the native ECD of CLPTM1) is preferred. For example the polypeptide may be in the form of a fusion protein comprising a polypeptide having the sequence of SEQ ID NO: 28 or 42 or a sequence which is a part of SEQ ID NO: 28 or 42 comprising at least 6 contiguous amino acids, or a sequence which has at least 75% identity to SEQ ID NO: 28 or 42. In another embodiment the polypeptide may not have a fusion partner, but may be a naked polypeptide, or the polypeptide may be conjugated to another moiety, e.g. a non-peptide based polymer such as is described further below. For example the polypeptide may comprise a part of SEQ ID NO: 28 or 42 which comprises at least the sequence DYYPI (SEQ ID NO: 41).

In one embodiment, a polypeptide obtained or derived from CLPTM1 does not inhibit binding of an endogenous ligand to CLPTM1, and/or does not inhibit receptor activation or stimulation by an endogenous ligand. However, in other embodiments it may be desirable or advantageous for binding and/or receptor activation or stimulation by an endogenous ligand. In this respect, an endogenous ligand may be a ligand other than a TBF-β.

It will be seen that the invention provides a range of different polypeptides which may be obtained or derived from the receptor and may have different sizes and which may contain one or more binding sites for TGF-β. Accordingly a repertoire, or panel, or library, or set of different polypeptides may be provided. Different polypeptides may differ in their affinity for different TGF-β proteins and may be used according to choice, e.g. to provide a differing binding activities for different TGF-β proteins. They may be used singly or in combination. Thus, different polypeptides may allow therapy to be extended, or continued, for example if the subject being treated develops an immune response to a particular polypeptide, another may then be selected for use. Polypeptides may be used in combination to provide a greater therapeutic effect, or they may be used to combat different conditions, depending on which TGF-β protein(s) is/are involved.

As noted above, a polypeptide comprises a minimum of 6 amino acids. However, longer polypeptides may advantageously bind to TGF-β with higher affinity, and thus a polypeptide may or comprise at least 7, 8, 9, 10, 11, 12, 13, 14, 15, 16, 17, 18 or 19 or more amino acids.

A polypeptide obtained or derived from the ECD of CLPTM1 (SEQ ID NO. 2) may comprise 6 to 354 amino acids, e.g. any one of 6, 7, 8, 9, 10, 12, 14, 16, 18 or 20 to any one of 354, 353, 350, 320, 300, 280, 260, 250, 240, 220, 200, 180, 160, 150, 140, 120, 100, 90, 80, 70, 60, 50, 40, 30 or 20, for example amino acids from or corresponding to SEQ ID NO.2 or a part thereof. For example, a polypeptide may have or comprise 6, 7, 8 or 9 to 50, 45, 40, 35, or 30 amino acids or more obtained or derived from SEQ ID NO: 2, or corresponding to a part thereof. In other embodiments, a polypeptide may have or comprise from 6, 7, 8, 9, 10, 12, 15, 20, 25, 30, 35, 40, 45 or 50 to 55, 60, 70, 80, 90, 100, 110, 120, 130, 140, 150, 160, 170, 180, 190, 200, 210, 220, 230, 235, 240, 245 or 250 amino acids obtained or derived from SEQ ID NO: 2, or corresponding to a part thereof.

In certain embodiments of the present invention the polypeptide may comprise the native N-terminal methionine residue encoded by the CLPTM1 gene, e.g. where the native or endogenous CLPTM1 start codon is provided in a nucleic acid sequence encoding the polypeptide. The polypeptide may, therefore, comprise amino acids 1 to 137, 138, 139, 140, 150, 160, 180, 200, 220, 240, 260, 280, 288, 290, 300, 320, 340, 350 or 354 of the amino acid sequence set forth in SEQ ID NO: 1. Thus, in a further embodiment the polypeptide may have or comprise an amino acid sequence corresponding to SEQ ID NO: 2 together with an N-terminal methionine. Such a polypeptide is represented by SEQ ID NO: 227. Accordingly, where SEQ ID NO: 2 is referred to herein such a reference may be replaced or supplemented with a reference to SEQ ID NO: 227. In other words, any reference herein to SEQ ID NO: 2 may be taken also to include a reference to SEQ ID NO: 227.

Indeed, a polypeptide of the invention may comprise or have a length within a range corresponding to between and including any integer included above, or lying within any of the ranges above. Furthermore, as will be described in more detail below, a polypeptide of the invention may be provided in fusion form or in other elongated or extended form, comprising one or more other amino acid sequences attached or coupled to the peptide sequence obtained or derived from CLPTM1. In other words, fusion proteins may comprise a polypeptide as described elsewhere herein linked or conjugated to a polypeptide that is not derived from CLPTM1, i.e. it may be linked to a non-CLPTM1 amino acid sequence (a fusion partner).

In a particular embodiment of the present invention, the polypeptide may comprise all or substantially all of an entire extracellular domain of CLPTM1.

A polypeptide of the invention may be provided in soluble form, e.g. as a soluble polypeptide, or a peptide which is provided with solubilising groups and/or moieties.

The polypeptide may be provided in monomeric, or in dimeric or higher multimeric form, i.e. it may be or more comprise a dimer or higher multimer of any of the polypeptides described or defined herein. Dimers or higher multimers may be formed in any convenient way, according to techniques known in the art. For example dimers may form spontaneously during the formation of fusion proteins, or they may be engineered.

It may advantageous or desirable to provide the polypeptide in the form of a fusion protein or construct or conjugate with a further moiety.

In certain embodiments, the polypeptide may be conjugated or linked to a natural or synthetic polymer, including a protein, polypeptide or peptide, or a polysaccharide, to improve its pharmacokinetic properties. In various embodiments the polypeptide may, therefore, be conjugated to linear or branched-chain monomethoxy poly-ethylene glycol (PEG; PEGylation), hyaluronic acid, dextran or dextrin, a homo-amino acid polymer (HAP; HAPylation), a proline-alanine-serine polymer (PAS; PASylation) or an elastin-like peptide (ELP; ELPylation) as described in Strohl. 2015. BioDrugs 29, 215-239, the entire disclosure of which is hereby incorporated by reference. Indeed, any known fusion or conjugation partner known in the art for use with therapeutic proteins may be used.

Any of the polypeptides of the present invention or disclosed herein may be provided as a fusion protein or chimeric protein, for example in order to increase the serum half-life of the polypeptide and/or to impart a further functionality to the polypeptide. The term "fusion protein" refers to a single polypeptide chain comprising polypeptide sequences from two or more different sources. A polypeptide of the invention or disclosed herein may be provided as a fusion protein in combination with any fusion partner. A fusion partner is defined broadly herein as a second polypeptide (or second amino acid sequence) which is not present in combination with (e.g. adjacent to, or linked to, directly or indirectly) the polypeptide (i.e. the first polypeptide), representing the polypeptide of the invention, or a polypeptide as disclosed herein in nature, and which is linked to the (first) polypeptide of the invention or disclosed herein, in a synthetic or artificial combination. Thus, a fusion protein comprises a non-native combination of at least two amino acid sequences or polypeptides linked, or fused together.

The fusion partner may be an amino acid sequence which is at least 6, 8, 9, 10, 15, 20, 25, 30, 40 or 50 or more amino acids long. Typically, the fusion partner is a functional polypeptide, or in other words it is a polypeptide which imparts a function or property to the fusion property, e.g. to stabilise the fusion protein (to make the "first" polypeptide more stable), or to increase its serum half-life. Thus the fusion partner may be a structural protein or have a structural function, or it may impart an activity or property to the fusion protein, e.g. a binding activity (e.g. the fusion partner may be a member of a binding pair, or it may be an affinity binding partner etc.). In representative examples the fusion partner may be an albumin, a fibrinogen, a glutathione S-transferase, a transferrin, streptavidin or a streptavidin-like protein, or an immunoglobulin, or a part thereof, in particular the Fc portion of an immunoglobulin (e.g. IgG1, IgG2, IgG3 or IgG4), or a part thereof (e.g. as an Fc-fusion protein). Within a fusion protein comprising a polypeptide of the invention, the polypeptide of the invention may be situated at the N-terminus of the fusion protein, or at the C-terminus of the fusion protein. Alternatively, the polypeptide of the invention may be situated internally in the fusion protein, e.g. within a loop or other surface feature of the fusion protein.

A fusion partner may be linked, or fused, to the polypeptide directly (i.e. via a peptide bond to the polypeptide) or indirectly, via a linker, generally speaking an amino acid linker sequence. This is described in more detail below.

In a preferred embodiment, a polypeptide of the invention/disclosed herein may be provided as fusion protein in combination with the Fc region of an immunoglobulin, i.e. may be provided as an Fc-fusion protein. In one preferred embodiment, the polypeptide of the invention is fused to the C-terminal of a Fc region, or a part thereof. In other words, the Fc region is the N-terminal component of the fusion protein. The Fc fusion partner may be linked to the polypeptide directly or indirectly, via a linker, as described in more detail below.

A fusion protein may also be conjugated to another moiety to provide a conjugate as discussed above, e.g. to another (e.g. non-protein) polymer.

Fc-fusion proteins form dimers, and thus in this embodiment two copies of a polypeptide (e.g. a polypeptide of the invention) may be provided as a single entity. In such an embodiment the dimer may either be a homodimer, comprising two identical polypeptides of the invention, or may be provided as a heterodimer, comprising two non-identical polypeptides of the invention. For example, the Fc-fusion protein may be a homodimer comprising two identical polypeptides derived from CLPTM1, as described herein, or may be a heterodimer comprising two different polypeptides derived from CLPTM1 as described herein. In a particular embodiment, the Fc-fusion protein may be a heterodimer comprising a first peptide comprising the sequence SEQ ID NO: 15 or a sequence having at least 75% sequence identity thereto and a second peptide comprising the sequence SEQ ID NO: 16 or a sequence having at least 75% sequence identity thereto.

As well as monomers and dimers, Fc fusions in higher multimeric forms, e.g. trimers or higher, are also known, and are included according to the present invention.

An Fc-fusion protein may comprise an Fc domain which is immunogenic. In other words, an Fc-fusion protein may comprise a sequence which is known to induce an immune response, e.g. a response by cells of the innate immune system. Thus, in one embodiment, an Fc-fusion protein may be immunogenic. In a particular embodiment, the immunogenic sequence may induce antibody-dependent cellular cytotoxicity (ADCC) and/or antibody dependent cell mediated phagocytosis (ADCP). Examples of immunogenic Fc-tag sequences are known in the art (see e.g. Lazar et al. 2006. PNAS 103, 4005-4010); Shields et al. 2001. J. Biol. Chem. 276, 6591-6604; and Stewart et al. 2011. Protein Engineering, Design and Selection 24, 671-678). Although not limited to such a use, such immunogenic Fc-fusion proteins may be of particular utility in the treatment of cancers which overexpress TGF-β, and which have high concentrations of TGF-β proximal to their cell surface. Such Fc fusion proteins may act to recruit cells of a subject's immune system to a site of cancer, and induce an immune response in addition to simply blocking the interaction between TGF-β and its receptors.

It may be desirable, however, for an Fc-fusion protein to comprise minimal immunogenic activity, i.e. to bind to (and thus sequester) TGF-β, without inducing an immune response. Thus, in a further embodiment, an Fc-fusion protein is not immunogenic.

In another preferred embodiment, a polypeptide may be provided as a conjugate with a bisphosphonate. Without wishing to be bound by theory, it is believed that such a construct might be directed for enrichment (i.e. to accumulate) in bone. Such an accumulation may have particular advantages in preventing the interaction of TGF-β with its receptors which may be present in bone, which may be of particular benefit in inhibiting the engagement of bone in cancer.

In any of the fusion proteins or conjugates contemplated in the present invention, a polypeptide derived from CLPTM1 may be linked to its conjugate or fusion partner at its N-terminus and/or at its C-terminus by a linker sequence or linker or spacer group. For fusion proteins comprising a polypeptide/peptide based fusion partner the linker will conveniently be a peptide/polypeptide linker, many of which are known and described in the art. The linker may be a flexible linker sequence (which may include repeats of a flexible linker sequence motif). Typical linkers known in the art are rich in small non-polar (e.g. glycine) or polar (e.g. serine or threonine) residues, and commonly consist of stretches of glycine and serine residues (GS). A commonly used linker is the (GGGGS) linker (SEQ ID NO: 228), which may be provided as a repeating unit in a linker (as (GGGGS)$_n$) where the copy number of n may be adjusted. For example, n may be 1-10, e.g. 1-8, 1-6, or 1-4, such as 4.

For conjugates with non-polypeptide/peptide polymers (such as PEG or polysaccharides etc.) or with other conjugate partners, the polypeptide of the invention may be coupled or linked (conjugated) to the other moiety (conjugate partner) using any known or desired coupling chemistry or linker/coupling groups. A wide variety of these are described in the art.

In yet another embodiment, the polypeptides of the present invention may be provided as cyclic peptides. Cyclic peptides are of particular utility in the oral administration of a protein or peptide-based therapeutic agent, as they are typically highly resistant to proteolysis, and are thus not broken down by proteolytic enzymes in the digestive tract. However, cyclic peptides also typically exhibit increased serum half-life when compared with a structurally-related linear peptide.

Polypeptides are described herein which comprise one or more amino acid substitutions relative to the wild-type sequences for an extracellular domain of a CLPTM1 receptor, yet which retain the ability to bind to TGF-β. A polypeptide of the present invention will preferably have a high degree of sequence identity to that of the equivalent section of the sequence found in the native protein. A polypeptide of the invention has at least 75% sequence identity and preferably will have at least 80%, 85%, 86%, 87%, 88%, 89%, 90%, 91%, 92%, 93%, 94%, 95%, 96%, 97%, 98% or 99% sequence identity to that of the equivalent section of the sequence found in the native protein. However, in a particular aspect of the present invention a polypeptide which is used to block the interaction of TGF-β and CLPTM1 by binding to TGF-β may comprise an identical sequence to that of the equivalent section of the sequence found in the native protein. Without wishing to be bound by theory, it is possible that such a polypeptide may provoke less of an immune response (i.e. be less immunogenic) than a polypeptide having one or more substitutions relative to the native protein, as a polypeptide having a non-native sequence may be recognised as 'foreign' by a subject's immune system.

Sequence identity may readily be determined by methods and software known and readily available in the art. Thus, sequence identity may be assessed by any convenient method. However, for determining the degree of sequence identity between sequences, computer programs that make multiple alignments of sequences are useful, for instance Clustal W (Thompson et al., (1994) Nucleic Acids Res., 22: 4673-4680). Programs that compare and align pairs of sequences, like ALIGN (Myers et al., (1988) CABIOS, 4: 11-17), FASTA (Pearson et al., (1988) PNAS, 85:2444-2448; Pearson (1990), Methods Enzymol., 183: 63-98), BLAST and gapped BLAST (Altschul et al., (1997) Nucleic Acids Res., 25: 3389-3402) are also useful for this purpose, and may be used using default settings. Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26: 316-9). Multiple sequence alignments and percent identity calculations may be determined using the standard BLAST parameters, (using sequences from all organisms available, matrix Blosum 62, gap costs: existence 11, extension 1). Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

Variants of the naturally occurring polypeptide sequences as defined herein can be generated synthetically e.g. by using standard molecular biology techniques that are known in the art, for example standard mutagenesis techniques such as site-directed or random mutagenesis (e.g. using gene shuffling or error prone PCR). Such mutagenesis techniques can be used to develop polypeptides which have improved or different binding and/or inhibitory properties.

Derivatives of the polypeptides as defined herein may also be used. By derivative is meant a polypeptide as described above or a variant thereof which instead of the naturally occurring amino acid contains a structural analogue of that amino acid. Derivatisation or modification (e.g. labelling, glycosylation, methylation of the amino acids in the polypeptide) may also occur as long as the function of the polypeptide is not adversely affected.

By "structural analogue", it is meant a non-standard amino acid. Examples of such non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-β methylamino acids, or D-N-methylamino acids.

Where a polypeptide comprises an amino acid substitution relative to the sequence of the native protein, the substitution may preferably be a conservative substitution. The term "a conservative amino acid substitution" refers to any amino acid substitution in which an amino acid is replaced (substituted) with an amino acid having similar physicochemical properties, i.e. an amino acid of the same class/group. For instance, small residues Glycine (G), Alanine (A) Serine (S) or Threonine (T); hydrophobic or aliphatic residues Leucine (L), Isoleucine (I); Valine (V) or Methionine (M); hydrophilic residues Asparagine (N) and Glutamine (Q); acidic residues Aspartic acid (D) and Glutamic acid (E); positively-charged (basic) residues Arginine (R), Lysine (K) or Histidine (H); or aromatic residues Phenylalanine (F), Tyrosine (Y) and Tryptophan (W), may be substituted interchangeably without substantially altering the ability of a polypeptide to bind to TGF-β.

As noted previously, several diseases, disorders and conditions are associated with increased levels of TGF-β. Such increased levels of TGF-β may be detectable in the circulation or in tissues or organs of the body. TGF-β may also increase locally at the site or vicinity of a tumour or infection, or site of fibrosis, for example it may accumulate in or around the stroma or extracellular matrix of a tumour.

A condition associated with elevated levels of TGF-β may be any condition, disease or disorder in which the level of TGF-β is increased, including in the circulation and/or locally, e.g. at a site of, or in the vicinity of, a cancer (for example a tumour) or other injury or disorder (e.g. at a site of inflammation or infection). For instance, where TGF-β is increased locally at the site of a cancer (e.g. tumour), the increase may not be such as to have an appreciable effect on circulating levels of TGF-β, but the local concentration or amount of TGF-β may be increased (for example in the microenvironment of the tumour). Thus the level of TGF-β may be increased relative to a subject without the condition in question e.g. a healthy subject, or relative to site or location in the body of the subject in which the condition is not, or was not, present.

A condition associated with elevated levels of TGF-β may thus include any condition in which the level of TGF-β is aberrant, whether in the circulation or locally at any site in the body. Also included according to the present invention is any condition in which the level of TGF-β is unwanted, e.g. results in a deleterious or harmful effect on the subject. Further included is any condition in which activity of TGF-β is increased or unwanted.

Such a condition may include any of the conditions mentioned above which are known to be associated with increased or elevated TGF-β levels. As noted above, in a particular embodiment such a condition is not associated with elevated or unwanted levels of GDF15.

Representative conditions include cancer, conditions involving inflammation and/or immunosuppression which are characterised by TGF-β overexpression, fibrosis and fibrotic diseases, and infections. In certain embodiments the condition is a cancer, inflammation or inflammatory condition or immunosuppression, which condition is not associated with elevated or unwanted levels of GDF15; or an infection, or fibrosis or a fibrotic condition. In another embodiment the condition is a cancer, inflammation or inflammatory condition, immunosuppression or infection, which condition is not associated with elevated or unwanted levels of GDF15; or fibrosis or a fibrotic condition.

Cancer represents a condition of particular interest according to the present invention. As noted above, in late-stage cancers, over-expression of TGF-β is correlated to metastasis and immune suppression. Elevated TGF-β levels, whether circulating or locally at the site of a cancer, have been reported for a number of cancers, and analyses may be performed to detect or identify such cancers. Reference may be made to Table 2 below, which shows RNAseq expression data from the 4 ligands GDF15 and TGF-β1, 2 and 3 as obtained from the UCSC genome browser. This shows that cancers may be identified which are non-overlapping as regards GDF15 and TGF-β expression, that is that certain cancers may be associated with elevated levels of TGF-β but not with elevated levels of GDF15. Particular mention may be made of breast cancer (high TGF-β 3 and low GDF15) and gliobastoma (high TGF-β2, low GDF15).

The cancer may be prostate cancer, bladder cancer, multiple myeloma, melanoma, colorectal cancer (including colon cancer and rectal cancer), kidney cancer, gastric cancer, breast cancer, ovarian cancer, endometrial cancer, oral squamous carcinoma, pancreatic cancer, lung cancer, oral cancer, oesophageal cancer, testicular cancer or liver cancer.

TABLE 2

| | over expressed in %-of patients | | | |
| cancer type | GDF15$^{HIGH}$ | TGFb1$^{HIGH}$ | TGFb2$^{HIGH}$ | TGFb3$^{HIGH}$ |
| --- | --- | --- | --- | --- |
| Bladder | >75% | >50% | | — |
| Breast | — | | >50% | >90% |
| Cervical | — | | | — |
| Colon | >90% | | | — |
| Endometriod | — | | | — |
| Glioblastoma | — | | >95% | — |
| Head and neck | | >75% | | |
| Kidney Chromo | >90% | | | — |
| Kidney Clear cell | >50% | >75% | | — |
| Kidney papillary | >90% | | | — |
| B-cell lymphoma | | >95% | | |
| Liver | >50% | | | — |
| Glioma lower grade | — | | >50% | — |
| Lung Adeno | >50% | | | — |
| Lung Squam | | | | |
| Melanoma | >90% | | | — |
| Mesothelioma | — | >50% | >50% | >90% |
| Ocular melanoma | >90% | | | — |
| Ovarian | | | >50% | |
| Pancreatic | >50% | >50% | >75% | >75% |
| Prostate | >95% | | >75% | >50% |
| Rectal | >95% | | | — |
| Sarcoma | — | >50% | >50% | >50% |
| Testicular | | | | |
| Thyroid | >50% | | >50% | |
| Uterine car. sarc. | | | >90% | |
| Myeloid leukemia | | >95% | | |

Example 5 shows in Table 4 below that various cancers may be identified expressing TGF-β and CLPTM1 in proximity, for example lung adenocarcinoma and squamous carcinoma of the lung or larynx, adenocarcinoma of the stomach or colon, kidney, pancreas, bladder, prostate and breast etc. Any such cancer may be a cancer which may be the subject of therapy according to the present invention. The cancer may in another embodiment be any cancer reported in the literature to be associated with TGF-β overexpression, e.g. colon cancer or colorectal cancer. It may be such a cancer which is not associated with elevated or unwanted levels of GDF15. Agents which are capable of reducing the activity of TGF-β, or the ability of TGF-β to bind to CLPTM1 thus represent an attractive therapy in the field of oncology.

It is proposed in particular that the interaction between TGF-β and CLPTM1 may be of particular significance in the pathology of many different cancers, in particular with regard to the modulation of immune function that is associated with elevated levels of TGF-β.

The term "cancer" is used broadly herein to include any malignant, non-malignant or pre-malignant neoplasm, including both solid and non-solid tumours, e.g. haemopoietic cancers. Any known cancer, including a cancer of any tissue or cell of the body is envisaged, and different cancer types, including but not limited to those listed above. In certain embodiments, however, the cancer is not rectal, colon, or prostate cancer (or is not prostate or rectal cancer). In another embodiment it is not any one or more of breast, cervical, or endometrial cancer, or it is not a glioma, a sarcoma other than Ewing Sarcoma, mesothelioma or blood cell cancer. In other embodiments such cancers are included.

The cancer may be a primary or secondary cancer, i.e. a cancer which has metastasised to a secondary site in the body, including micrometastases.

TGF-β is capable of down-regulating the immune response provided by a number of different immune cells, for example Natural Killer cells (NK-cells), macrophages and/or dendritic cells. As noted above, CLPTM1 has been shown to be expressed by various immune cells, including CD4 and CD8 positive T-lymphocytes, CD14 positive monocytes/macrophages, CD11c positive dendritic cells and/or NK cells. In work underlying the present invention we have thus shown that T-cell and/or other lymphocyte sub-sets may express CLPTM1. Interestingly, the majority of CD14 positive cells (monocytes/macrophages) were markedly positive for CLPTM1. As TGF-β has been shown to disrupt cytolytic functions such as Perforin and Granzyme), we foresee that CLPTM1 binding agents may be of particular utility in immune-oncology applications where tumour derived TGF-β reduces the capacity of immune effector cells such as NK and T-cells to mediate a cytolytic action.

Elevated TGF-β levels in the tumour stroma or at sites of metastasis (including micrometastasis) are thought to provide a significant mechanism for evasion of the immune system by cancer cells. The polypeptides of the present invention may therefore have utility in preventing or reducing the immunosuppressive effects of TGF-β.

Thus, more generally the polypeptides of the invention may be used to inhibit immunosuppression caused by or resulting from TGF-β, or immunosuppression associated with an elevated level of TGF-β. In particular, such immunosuppression may be immunosuppression which is not associated with elevated or unwanted levels of GDF15.

Such immunosuppression may in particular be suppression of a cell-mediated cytotoxic immune response. Thus the immunosuppression may be immunosuppression resulting from decreased activity of one or more immune cells, e.g. macrophages, NK cells, dendritic cells, neutrophils, and/or T-cells.

More specifically the immunosuppression may be in the context of cancer i.e. immunosuppression associated with cancer. The immunosuppression may be due to increased circulating levels of TGF-β, or in certain preferred embodiments, due to an elevated local concentration of TGF-β at the site of the cancer, e.g. tumour. In other embodiments, discussed in more detail below, the immunosuppression may be associated with, or may occur in the context of an infection. Notably this may be an infection with a pathogen or parasite.

In particular, the polypeptides of the present invention may be of utility in inhibiting immune evasion by cancer cells, or inhibiting immune tolerance induced by cancer cells. Polypeptides of the invention which block the interaction between TGF-β and CLPTM1 may be of utility in inhibiting immune evasion by cancer cells. Thus, peptides obtained or derived from CLPTM1 which are capable of binding to CLPTM1 described herein may of particular utility in this regard.

By inhibiting immune evasion, the therapeutic agents of the invention may help the body of the subject to attack the cancer. Thus, the invention may assist in reducing or abrogating a cancer in the body of a subject by promoting (or facilitating or increasing or in any way enabling or assisting) an immune response in the body against the cancer.

In one particular aspect the therapeutic agents may be used to inhibit spread or metastasis of the cancer. This may include inhibiting the development of micrometastasis, or inhibiting the growth or spread of a micrometastasis. The metastasis may be of any cancer to any part of the body. In particular embodiments it may a metastasis of prostate, breast or lung cancer, including for example to the bone.

As shown in Example 7 below, a polypeptide of the invention (particularly in this case the form of a Fc fusion protein) resulted in an increased production of IL-2 by immune cells upon LPS stimulation with no detectable changes in other cytokines such as TNF, IL6, VEGF and others (FIG. 9). IL-2 drives the proliferation and differentiation of T-cells and NK-cells vital for a potent anti-tumour immune response. This illustrates the usefulness of a CLPTM1-Fc fusion for cancer treatment to potentially increase IL-2 production in the tumour micro environment enhancing T-cell proliferation.

Without wishing to be bound by theory a further (alternative or additional) mechanism by which a polypeptide may operate is to activate an immune cell (which may include relieving inhibition of the cell), and thereby activate or facilitate or aid or improve etc., an immune response against the cancer (or other condition, infection etc.), for example an innate immune cell, e.g. an antigen presenting cell, such as a dendritic cell or macrophage.

In the treatment of cancer the polypeptides of the invention may be used in combination or conjunction with other anti-cancer therapies, e.g. with other anti-cancer agents, including other immunotherapeutic or immunoncological agents or chemotherapeutic agents. Thus, for example, the agents of the invention may be used in conjunction with cell-based cancer therapies, e.g. adoptive cell transfer therapy and/or with antibody-based therapies, as well as in combination with any other anti-cancer agent, e.g. with an anti-cancer drug.

In a particular embodiment, the agents of the present invention may be used in conjunction with adoptive cell transfer therapy, particularly NK-cells or T-cells (or more generally with cytotoxic immune cells), which may be in some embodiments be modified to express a chimeric antigen receptor (CAR), or T-cells expressing or modified to express (i.e. comprising a native or a heterologous) T-cell receptor, which has specificity for an antigen present on the surface of a cancer cell.

Such cytotoxic immune cells may be modified to have a reduced level and/or activity of CLPTM1 compared with a cell which has not been modified, e.g. by gene knockout, gene knockdown or gene deletion.

Thus, the gene (i.e. the sequence in the cell encoding the CLPTM1 protein) may be modified to reduce the amount of the CLPTM1 protein expressed, for example the amount of CLPTM1 receptor at the cell surface, and/or the activity of the receptor protein. Thus, the receptor protein may be inactivated. This may involve, for example, modifying the gene sequence by and/or insertion or replacement/substitution of the native nucleotide sequence e.g. of a nucleotide sequence of the native CLPTM1 gene. This may be achieved by standard mutagenesis techniques and/or homologous substitution, or CRISPR or shRNA or siRNA technology etc., as known in the art.

In particular embodiments, the cell may be a T-cell expressing or modified to express a T-cell receptor or a T-cell modified to express a CAR. In a further embodiment, the cell may be an NK cell, optionally modified to express a CAR. Said modified cells may be or particular utility in the treatment of cancer, and thus in one embodiment, the cells will comprise a TCR or a CAR having specificity towards an antigen on the surface of a cancer cell. A combined product or preparation (e.g. a kit) may comprise said cells and a therapeutic agent, being a polypeptide according to the present invention, for separate, sequential or simultaneous use in treating cancer which is associated with elevated or unwanted levels of TGF-β, and in particular a cancer which is not associated with elevated or unwanted levels of GDF15. Thus a method, or use, of the present invention to treat cancer may comprise administering to a subject (in particular a subject in need thereof) a polypeptide of the invention and (i.e. together, or in combination or conjunction, with) a said modified cytotoxic immune cell. The cell and therapeutic agent (polypeptide) may be administered separately, sequentially or simultaneously, e.g. in separate formulations, as discussed above. Accordingly, a kit or combined product may comprise a polypeptide and a modified cell, as hereinbefore described.

The agents of the present invention may also be used in conjunction with immunotherapeutic agents that target an immune checkpoint, i.e. immune checkpoint inhibitors, in the treatment of cancer. Checkpoint proteins keep the immune system in check by indicating to the immune system which cells are healthy and which cells should be destroyed. Checkpoint proteins act as a "brake" on the immune system by preventing T-cell activation. If a cell does not have sufficient checkpoint proteins on its surface it may be destroyed by the immune system. In the case of cancer cells, whilst there may be molecules signalling that the cell is cancerous, if there are enough checkpoint proteins on the cell surface, the cell may evade the immune response, and it has been speculated that checkpoint proteins contribute to a lack of success in some cancer immunotherapies.

The best known example of a checkpoint protein is PD-L1 (for Programmed Death Ligand 1). The receptor for PD-L1 is PD-1. PD-L1 prevents T-cells from attacking healthy cells. Cancer cells may up-regulate PD-L1 as a protective mechanism. When PD-L1 activates the PD-1 receptor on the surface of a T-cell, the T-cell is signalled to destroy itself. If the T-cells are programmed to selectively attack cancer cells, that set of T-cells will be destroyed and the cancer prevails.

Another checkpoint protein is cytotoxic T-lymphocyte antigen-4, or CTLA4. Once a cytotoxic T cell becomes active it expresses CTLA4 on its surface, which then competes with the co-stimulatory molecule CD28 for their mutually shared ligands, B7-1 and B7-2 on antigen-presenting cells. This balance holds cytotoxic activity in check, while allowing T cell function to proceed in a self-limited manner.

Other checkpoint proteins include CD-137 (4-1BB) which is a co-stimulatory checkpoint protein; lymphocyte activation gene 3 (LAG-3, CD223), a CD4-related inhibitory receptor co-expressed with PD-1 on tolerant T cells; B7 superfamily proteins B7-H3 and B7-H4; T cell protein TIM3; and phosphatidylserine (PS) which is a phospholipid in normal cells that is translocated to the outer member surface during apoptosis, suppressing the excess immune activation that would otherwise occur during processing and clearance of decaying cell matter. Externalization of PS indirectly stimulates macrophages, resulting in suppression of dendritic ell antigen presentation. Like PD-L1, externalized PS is aberrantly expressed by some tumour cells and tumour-derived microvesicles. Thus, PS is believed to be exploited by tumours to prevent adaptive tumour immunity.

Immunotherapeutic agents which may target or inhibit any of these checkpoint proteins are known as "checkpoint inhibitors".

Checkpoint inhibitors (also known as immune checkpoint modulators, or CPMs) are designed to lessen the effectiveness of checkpoint proteins. Ideally a CPM should expose cancers to the immune system without causing that same system to attack healthy tissue.

Several checkpoint inhibitors are known and can be used in conjunction with the agents of present invention in the treatment of cancer, for example those inhibitors described in Creelan (2014) Cancer Control 21:80-89, which is hereby incorporated by reference.

Examples of checkpoint inhibitors include: Tremelimumab (CP-675,206), a human IgG2 monoclonal antibody with high affinity to CTLA-4; Ipilimumab (MDX-010), a human IgG1 monoclonal antibody to CTLA-4; Nivolumab (BMS-936558), a human monoclonal anti-PD1 IgG4 antibody that essentially lacks detectable antibody-dependent cellular cytotoxicity (ADCC); MK-3475 (formerly lambrolizumab), a humanized IgG4 anti-PD-1 antibody that contains a mutation at C228P designed to prevent Fc-mediated ADCC; Urelumab (BMS-663513), a fully human IgG4 monoclonal anti-CD137 antibody; anti-LAG-3 monoclonal antibody (BMS-986016); and Bavituximab (chimeric 3G4), a chimeric IgG3 antibody against PS. All of these checkpoint inhibitors can be used in the present invention.

An alternative strategy is to inhibit PD-L1, the ligand for PD-1, on the tumour cell surface, and therefore inhibitors of PD-L1 are may also be used in conjunction with the agents of the present invention, for example, MPDL3280A (RG7446), a human IgG1-kappa anti-PD-L1 monoclonal antibody. MEDI4736 is another IgG1-kappa PD-L1 inhibitor.

Another alternative approach is to competitively block the PD-1 receptor, using a B7-DC-Fc fusion protein, and such fusion proteins can also therefore be used in the present invention.

In a further alternative approach an antibody to Killer cell immunoglobulin-like receptor may be used as the immunotherapeutic agent. Killer cell immunoglobulin-like receptor (KIR) is a receptor on NK cells that downregulates NK cytotoxic activity. HLA class I allele-specific KIR receptors are expressed in cytolytic (CD56dimCD16+) NK cells, while CD56brightCD16− NK subset lacks these KIRs. Along these lines, inhibitory KIRs seem to be selectively expressed in the peritumoral NK cell infiltrate and thus seem to be a checkpoint pathway co-opted by tumours, similar to PD-L1. As such, inhibition of specific KIRs using antibodies should cause sustained in vivo activation of NK cells. For example, lirilumab (IPH2102) is fully human monoclonal antibody to KIR and can be used according to the invention.

Thus, an immune checkpoint inhibitor may be broadly defined as any agent which inhibits the activity or function of a checkpoint protein. This may be an agent which binds to a checkpoint protein or to a receptor for a checkpoint protein. A checkpoint inhibitor may thus be a binding agent for a checkpoint protein or for a receptor therefor. A binding agent may be, or may be based on or derived from, an antibody. The antibody may be a natural or synthetic antibody, or a fragment or derivative thereof. The term "antibody" is thus used broadly herein to include any type of antibody or antibody-based molecule. This includes not only native antibody molecules but any modified, synthetic or recombinant antibodies, as well as derivatives or fragments thereof. An antibody may thus be any molecule or entity or construct having antibody-based binding region(s), that is a binding domain(s) which is/are derived from an antibody. Accordingly, an antibody may alternatively be defined as a binding molecule comprising an antigen-binding domain obtained or derived from an antibody. The antibody may be of, or may be derived from/based on, an antibody of any convenient or desired species, class or sub-type. As noted above, the antibody may be natural, derivatised or synthetic. It may be monoclonal or polyclonal. Thus the antibody may bind to a single epitope or it may be a mixture of antibodies (or antibody molecules) binding to different epitopes.

Accordingly, the checkpoint inhibitor may be a binding molecule comprising an antigen binding domain from an antibody specific for (or directed against) a checkpoint protein or a receptor therefor. Examples of such "antibodies" (i.e. antibody-based binding molecules) include monoclonal or polyclonal antibodies, antibody fragments including Fab, Fab', F(ab')2 or Fv fragments or any fragment lacking a Fc region, chimeric (e.g. humanised or CDR-grafted) antibodies, single chain antibodies (e.g. ScFv antibodies), antibodies identified or obtained from phage display etc.

In an embodiment the immune checkpoint inhibitor is an antibody against PDL-1, PD-1, CTLA4, TIM3, CD137, CD223, PS, or a KIR on an NK cell, or it is B7-DC-Fc fusion protein.

A product (e.g. a combined product or preparation, e.g. a kit) may comprise a checkpoint inhibitor and a polypeptide according to the present invention, for separate, sequential or simultaneous use in treating cancer which is associated with elevated or unwanted levels of TGF-β, and in particular a cancer which is not associated with elevated or unwanted levels of GDF15.

Thus a method, or use, of the present invention to treat cancer may comprise administering to a subject (in particular a subject in need thereof) a polypeptide of the invention and (i.e. together, or in combination or conjunction, with) a checkpoint inhibitor. The checkpoint inhibitor and (polypeptide) may be administered separately, sequentially or simultaneously, e.g. in separate formulations, as discussed above. Accordingly, a kit or combined product may comprise a polypeptide and a checkpoint inhibitor, as hereinbefore described.

In a further aspect, the polypeptide and the immune checkpoint inhibitor may be provided as a single moiety or construct, i.e. as a bifunctional (or bispecific) construct (or bifunctional or bispecific protein). In other words, the polypeptide (which may optionally be in the form of a fusion protein as hereinbefore described) may be linked (or fused or conjugated), directly or indirectly, to a checkpoint inhibitor. Indirect linkage may be via a linker or spacer as defined and described above in connection with fusion proteins and conjugates In this aspect, the present invention therefore provides a bifunctional construct comprising a polypeptide capable of binding to TGF-β and inhibiting the interaction of TGF-β with the receptor CLPTM1 (i.e. a polypeptide as defined or described herein), and an immune checkpoint inhibitor (as defined or described herein).

In a particular embodiment of this aspect the immune checkpoint inhibitor may be an "antibody" (which includes antibody fragments or derivatives etc.) directed against (or binding specifically to) PD-L1, PD-1, CTLA4, TIM3, CD137, CD223, PS, or a KIR on an NK cell. In one preferred embodiment the checkpoint inhibitor is an antibody that binds human protein Programmed Death Ligand 1 (PD-L1) or Programmed cell death protein 1 (PD-1).

Any suitable antibody which recognises and binds to a cancer antigen may also be used in conjunction with the agents of the invention (i.e. with the polypeptides (including fusion proteins) or bifunctional constructs). Examples of cancer antigens, or targets for therapeutic antibodies, include many "CD" proteins, such as CD52, CD47, CD30, CD33, CD20, CD152 and CD279; growth factors such as vascular endothelial growth factor (VEGF); growth factor receptors such as epidermal growth factor receptor (EGFR) or human epidermal growth factor receptor 2 (HER2).

Several antibodies that bind to such antigens or targets are known and have been approved for the treatment of cancer, and any of these antibodies may be used conjunction with the agents of the present invention. Preferred antibodies are those that have utility in treating solid tumours, and especially those with an altered ECM, such as breast, ovarian and pancreatic cancers.

Known and approved antibodies include: Alemtuzumab, Bevacizumab, Brentuximab vedotin, Cetuximab, Gemtuzumab ozogamicin, Herceptin, Ibritumomab tiuxetan, Ipilimumab, Ofatumumab, Panitumumab, Rituximab, Tositumomab and Trastuzumab.

Alemtuzumab is an anti-CD52 humanized IgG1 monoclonal antibody indicated for the treatment of fludarabine-refractory chronic lymphocytic leukemia (CLL), cutaneous T-cell lymphoma, peripheral T-cell lymphoma and T-cell prolymphocytic leukemia.

Bevacizumab (Avastin) is a humanized IgG1 monoclonal antibody which binds to vascular endothelial growth factor-A (VEGF-A) (referred to commonly as VEGF without a suffix). Bevacizumab binds to and physically blocks VEGF, preventing receptor activation which has consequences for tumour vascularisation. Bevacizumab is licensed for colon cancer, kidney cancer, lung cancer, ovarian cancer, glioblastoma and breast cancer.

Brentuximab vedotin is a second generation chimeric IgG1 antibody drug conjugate used in the treatment of Hodgkin lymphoma and anaplastic large cell lymphoma (ALCL). It is an antibody conjugated to monomethyl auristatin E, a drug that prevents cell division by disrupting microtubules. The antibody binds to CD30, often found highly expressed on the surface of Hodgkin lymphoma and ALCL cells, and is then internalised where the drug is detached from the antibody and exerts its cellular effects. By preventing cell division it kills cancer cells by the induction of programmed cell death.

Cetuximab (Erbitux) is a chimeric IgG1 monoclonal antibody that targets the extracellular domain (part of the receptor outside the cell) of the epidermal growth factor receptor (EGFR). It is used in the treatment of colorectal cancer and head and neck cancer. Once a ligand binds to the EGFR on the surface of the cell, signalling pathways are activated inside the cell that are associated with malignant characteristics. These include the PI3K/AKT and KRAS/BRAF/MEK/ERK pathways that cause cancer cell proliferation, invasion, differentiation and cancer stem cell renewal. Cetuximab functions by competitively inhibiting ligand binding, thereby preventing EGFR activation and subsequent cellular signalling.

Gemtuzumab ozogamicin is an "immuno-conjugate" of an IgG4 anti-CD33 antibody chemically linked to a cytotoxic calicheamicin derivative, and may be used for the treatment of acute myeloid leukaemia (AML).

Ibritumomab tiuxetan (Zevalin) is a murine anti-CD20 antibody chemically linked to a chelating agent that binds the radioisotope yttrium-90 (90Y). It is used to treat a specific type of non-Hodgkin lymphoma, follicular lymphoma, which is a tumour of B-cells.

Ipilimumab (Yervoy) is a human IgG1 antibody that binds the surface protein CTLA4 which has a role in negatively regulating the activation of T-cells.CTLA4 is discussed above in the context of checkpoint inhibitors.

Nimotuzumab is a chimeric human-mouse anti-EGFR monoclonal antibody and has been approved for squamous cell carcinoma in head and neck (SCCHN).

Ofatumumab is a second generation human IgG1 antibody that binds to CD20. It is used in the treatment of chronic lymphocytic leukemia (CLL) as the cancerous cells of CLL are usually CD20-expressing B-cells. Unlike Rituximab, which binds to a large loop of the CD20 protein, Ofatumumab binds to a separate small loop.

Panitumumab (Vectibix) is a human IgG2 antibody that binds to the EGF receptor. Like Cetuximab, it prevents cell signalling by the receptor by blocking the interaction between the receptor and its ligand. It is used in the treatment of colorectal cancer.

Rituximab is a chimeric monoclonal IgG1 antibody specific for CD20, developed from its parent antibody Ibritumomab. As with Ibritumomab, Rituximab targets CD20, which is present on B-cells. For this reason it is effective in treating certain types of malignancies that are formed from cancerous B-cells. These include aggressive and indolent lymphomas such as diffuse large B-cell lymphoma and follicular lymphoma, and leukaemias such as B-cell chronic lymphocytic leukaemia.

Tositumomab was a murine IgG2a anti-CD20 antibody covalently bound to radioactive Iodine 131 known as "Bexxar" that was approved for treatment of Non-Hodgkin lymphoma, but was voluntarily withdrawn from the market.

Trastuzumab (Herceptin) is a monoclonal IgG1 humanized antibody specific for the epidermal growth factor receptor 2 protein (HER2). It received FDA-approval in 1998, and is clinically used for the treatment of breast cancer. HER-2 is a member of the epidermal growth factor receptor (EGFR) family of transmembrane tyrosine kinases. In a preferred embodiment of the invention the immunotherapeutic agent, and hence anticancer agent, is trastuzumab, preferably for the treatment of ovarian cancer.

In an alternative embodiment the antibody is an anti-CD47 antibody, i.e. an antibody which blocks CD47 signalling. Such antibodies have been shown to eliminate or inhibit the growth of a wide range of cancers and tumours in laboratory tests on cells and mice. CD47 is present on many cancer cells and on many healthy cells.

In a further alternative embodiment the antibody is an antibody to a carbohydrate molecule found on the surface of cancer cells. By way of example, such an antibody may be an anti-GD2 antibody. GD2 is a ganglioside found on the surface of many types of cancer cell including neuroblastoma, retinoblastoma, melanoma, small cell lung cancer, brain tumours, osteosarcoma, rhabdomyosarcoma, Ewing's sarcoma, liposarcoma, fibrosarcoma, leiomyosarcoma and other soft tissue sarcomas. It is not usually expressed on the surface of normal tissues, making it a good target for immunotherapy to allow for specific action against the tumour and reduced toxicity.

In other embodiments, the therapeutic agents according to the present invention may be used in combination with radiotherapy, or in combination with STING agonists which elevate interferon.

Fibrosis and fibrotic conditions represent another class of condition which may be treated. The term fibrotic condition includes any fibrotic disease or disorder or any condition involving fibrosis. As noted above, such conditions include fibrosis of or in the lung, kidney, liver and skin. Particular conditions include fibrotic lung diseases such as idiopathic pulmonary fibrosis and chronic inflammatory conditions such as chronic obstructive pulmonary disease (COPD) and asthma, and conditions involving scarring, whether of the skin or elsewhere, e.g. in the lung, for example keloids, or other abnormal scars. Any condition characterised by TGF-β overexpression, inflammation and fibrosis is included, e.g. in the lung or in any other tissue or organ of the body, e.g. skin, kidney or liver. For the treatment or prevention of keloids, it may in certain embodiments be desirable to target only TGF-β1 and/or 2 and not TGF-β3. This may be achieved by selecting polypeptides which preferentially bind TGF-β1 and/or 2, e.g. which have higher affinity for TGF-β1 and/or 2 than for TGF-β3. TGFβ has also been shown to have a role in the pathology of Cystic Fibrosis (CF) (Sun et al. 2014. PLoS 9, e106842), and therapeutic agents according to the present invention may therefore be of benefit in the treatment of CF.

Infections represent a still further class of condition, particularly infections which modulate the immune system by or via TGF-β. Such modulation may through CLPTM1-TGF-β interactions. For infectious conditions TGF-β interaction may have a role in regulation of macrophage activity. Further, TGF-β is known to be used or correlated to resistance in a number of infections and hence therapeutic agents according to the invention may be of benefit to treat such infections.

Infections known to use the TGF-β axis include drug-resistant leishamaniasis, schistosomiasis, Chagas Disease (infection with Trypanosoma cruzi), multidrug resistant tuberculosis, HIV infection, cryptogenic organising pneumonia (COP), malaria, respiratory viral infections and Chikungunya virus. Thus, infections susceptible, or responsive, to treatment by the present invention may include infections with any parasite or pathogen, and include bacterial, fungal, viral, protozoal and helminth infections.

The therapeutic agents (i.e. polypeptides or constructs) of the invention may be used in combination with an antimicrobial (e.g. antibiotic; antibacterial and/or antifungal), antiviral, anti-protozoal and/or anti-helminth agent.

Accordingly a further aspect of the present invention provides a kit comprising a therapeutic agent (specifically a polypeptide or construct) as hereinbefore defined, together with at least one anti-pathogenic agent selected from an antimicrobial (e.g. antibiotic; antibacterial and/or antifungal), antiviral, anti-protozoal and/or anti-helminth agent.

Such kit may for use in treating or preventing a condition associated with elevated or unwanted levels of TGF-β, as defined and described herein, and may be provided as a combined product for separate, simultaneous or sequential use in treating or preventing a condition associated with elevated or unwanted levels of TGF-β.

The subject may be any human or non-human animal, preferably a mammalian animal subject. In a particular embodiment, the subject is human, but in other embodiments it may be a domestic, livestock, farm, zoo, wild, laboratory or sport (e.g. race) animal, e.g. a primate, dog, cat, murine, pig, cow, horse etc.

The ability of a polypeptide or construct of the present invention to reduce the activity of TGF-β (i.e. to prevent TGF-β from effecting or exerting its biological function) may thus be determined, by measuring whether a particular polypeptide or construct is able to reduce the activity of TGF-β. A polypeptide or construct of the present invention will thus preferably be able to bind to a CLPTM1 receptor or to TGF-β, and substantially inhibit or abrogate the activity of TGF-β i.e. to reduce the activity of TGF-β to less than 50%, 40%, 30%, 20% or 10% compared to the level of activity of TGF-β in the absence of a polypeptide or construct. More preferably, the polypeptide or construct will reduce the activity of TGF-β to less than 9%, 8%, 7%, 6%, 5%, 4%, 3%, 2%, 1% or less, i.e. the polypeptide or construct may preferably effectively eliminate the activity of TGF-β.

In addition to the polypeptides or constructs, a therapeutic composition may comprise any pharmaceutically acceptable diluent, carrier or excipient. "Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, pH, temperature etc.

Dosages of the therapeutic agents may also be determined in routine manner according to standard clinical practice. Doses of 0.1-10 mg/kg, such as doses of 0.1-0.5 mg/kg, 0.1-1 mg/kg, 0.1-2 mg/kg, 0.1-5 mg/kg, 0.5-1 mg/kg, 0.5-2 mg/kg, 0.5-5 mg/kg, 0.5-10 mg/kg, 1-2 mg/kg, 1-5 mg/kg, 1-10 mg/kg, 2-5 mg/kg, 2-10 mg/kg or 5-10 mg/kg may be administered daily, weekly, or every 10 days, 2 weeks, 3 weeks or monthly until disease progression, or until unacceptable toxicity is observed.

Likewise the therapeutic agents may be administered in any convenient or desired manner, e.g. parenterally or non-parenterally, for example by enteral administration, e.g. orally (depending on the nature and/or formulation of the agent), or by intravenous, sub-cutaneous, intramuscular, intraperitoneal injection or infusion. The administration may be systemic or local, depending e.g. on the condition to be treated, the nature of the agent and/or formulation etc. Thus, for example the agent may be delivered locally e.g. by infusion or direct injection, e.g. to the site or location of a cancer.

The interaction between TGF-β and the receptor CLPTM1, or an effect of the binding of TGF-β to the receptor, may be detected and such a detection method may be used as the basis of a companion diagnostic for the therapeutic or prophylactic methods disclosed herein.

Thus, the detection of an interaction and/or an effect thereof may be used to detect or determine that, or whether, a subject may be in need of therapy or prophylaxis (prevention) according to the present invention, or may benefit therefrom, or to monitor or assess the therapy or prophylaxis, e.g. during the course of or at the end of treatment. Thus the presence of an interaction of GDF15 with the receptor CLPTM1, or the presence of a detectable effect of TGF-β at the receptor CLPTM1, may be used as a biomarker, e.g. a predictive biomarker for administration of a therapy or prophylaxis according to the present invention, or to monitor or assess the effect of the therapy or prophylaxis. Further, by detecting an interaction and/or an effect thereof, it may be determined or detected whether a subject has a condition associated with an elevated TGF-β level, e.g. a cancer.

Accordingly, a further aspect of the present invention provides a method of detecting a subject in need of therapy or prophylaxis, particularly by administration of a therapeutic agent according to the present invention (that is a polypeptide or construct which is capable of inhibiting an interaction of TGF-β with the receptor CLPTM1, e.g. an agent as defined herein), said method comprising detecting an interaction between TGF-β and the receptor CLPTM1 and/or an effect of such an interaction in the subject.

In another aspect the invention provides a method of assessing or monitoring a method of therapy or prophylaxis by administration to a subject of a therapeutic agent according to the present invention (that is a polypeptide or construct which is capable of inhibiting an interaction of TGF-β with the receptor CLPTM1, e.g. an agent as defined herein), said method comprising detecting and/or monitoring an effect of such an interaction in the subject.

A still further aspect provides a method of detecting a subject having, or at risk of developing, a condition associated with an elevated level of TGF-β, said method comprising detecting in said subject an interaction of TGF-β with the receptor CLPTM1, or an effect of a said interaction.

The interaction or an effect thereof may be detected in vivo (i.e. in a subject) or in vitro. That is, the interaction or an effect thereof may be detected in the body of a subject or, preferably, in a sample from said subject. The sample may be any appropriate clinical sample. More particularly the sample may be a sample comprising cells expressing the receptor CLPTM1. The sample may thus be any cell-containing clinical sample from the subject. It may be a sample of tissue or body fluid, e.g. a tissue biopsy sample, blood or a blood-derived sample (e.g. plasma, serum, or a fraction thereof), urine, CSF, saliva, stool, or a swab, washing or rinsate etc.

An interaction may be detected by any means known in the art for detecting binding or interaction between two or more binding partners. Thus the method may be any method based on detecting binding between TGF-β and a receptor. It may for example be a proximity assay-based method, and in particular a proximity assay based on using antibody-based binding partners for the TGF-β and a receptor. Proximity assays are well known in the art and widely described in the literature. Proximity assays based on pairs (or more) of proximity probes each comprising an binding partner capable of binding directly or indirectly to an analyte (e.g. via an intermediate analyte-binding antibody or other binding partner for the analyte) and a nucleic acid domain which interacts with the nucleic acid domain of the other proximity probe(s) to generate a detectable signal when the probes have been bound in proximity (e.g. when the partners of an interacting pair have interacted or bound together) have been developed and commercialised by Olink AB of Uppsala, Sweden. The interaction between the nucleic acid domains of proximity probes may comprise a nucleic acid ligation and/or extension reaction and may be detected by detecting a ligation and/or extension product. The nucleic acid domains themselves may interact (e.g. may be ligated together), or they may template the formation of a ligation and/or extension product from one or more added oligonucleotides. Particular mention may be made of an in situ proximity ligation assay (PLA) which may be used to detect an interaction in situ in a cell or tissue sample. Such an assay has been developed by Olink AB and is marketed under the Duolink® brand name. Proximity assay are described in U.S. Pat. Nos. 6,878,515, 7,306,904, WO 2007/107743, WO/EP2012/051474 and WO2012/152942.

Further methods for detecting binding between TGF-β and a receptor may include immunoassays, such an enzyme-linked immunoassay (ELISA), radioimmunoassay (RIA) or immuno-PCR.

Various effects of TGF-β binding to CLPTM1 are described above and any of these may be detected.

The present invention may be better understood through the following Examples and Figures, in which:

FIG. 1 shows the results of an ELISA performed to detect binding of the ligands GDF15, TGFb1, TGFb2 and TGFb3 to various fragments of CLPTM1. The sequences of SEQ ID NOs: 8-40 are shown in Table 2. Binding of a ligand to a CLPTM1 fragment was identified using HRP-conjugated antibodies and TMB as a chromogenic substrate. Binding was quantified by measurement of the optical density (OD) of the reaction mix at 450 nm.

FIG. 2 shows the results of an ELISA to measure TNFα release from human macrophage cultures exposed to lipopolysaccharide (LPS) in combination with 50 ng/ml TGFb family ligands with or without 50 µg/ml 4F5 Fab fragments which bind CLTPM1. "None" is the negative control, showing macrophage TNFα production in the absence of LPS, TGFb or 4F5 Fab fragments. "LPS (+ non-affecting IgG)" is the positive control, showing maximal macrophage TNFα release in response to LPS exposure. T1/T2/T3 LPS show macrophage TNFα release when exposed to LPS in combination with TGFb1, TGFb2 and TGFb3, respectively. Fab4F5 T1/T2/T3 LPS show macrophage TNFα release when exposed to LPS in combination with TGFb1, TGFb2 and TGFb3, respectively, and 4F5 Fab fragments which bind CLTPM1.

FIG. 3 shows Western blots against TBK1 and PTP1B, demonstrating the effect of TGFb1 ligands on their cellular levels. In FIG. 3A, the effects of exposure to TGFb1 and TGFb3 on TBK1 and PTP1B levels in macrophage cells are shown in the "no siRNA" columns. In these columns, Ctrl indicates control cells not exposed to any ligand; M1 indicates exposure to MIC1 (GDF15), T1 exposure to TGFb1, T3 to TGFb3 and CtrR to a positive control ligand.

In the "siRNA-CLPTM1" columns the results are shown of the same experiments following siRNA knockdown of CLPTM1 expression. Samples were also blotted against GAPDH as a loading control.

In FIG. 3B results are shown for the same experiments, showing TBK1 levels in macrophages following exposure to TGFb1, TGFb2 and TGFb3. Ctrl indicates control cells not treated with a ligand; T1-C/T2-C/T3-C indicate macrophages exposed to TGFb1/TGFb2/TGFb3, respectively; T1-si/T2-si/T3-si indicate macrophages in which CLPTM1 expression has been knocked down with siRNA and then exposed to TGFb1/TGFb2/TGFb3, respectively.

FIG. 4 shows the effect of TGFb1/TGFb3 exposure on PTP1B/TBK1 levels in human cells. FIG. 4A is a Western blot showing the effect of TGFb3 exposure on PTP1B levels in MCF7 breast cancer cells. C indicates control cells, not exposed to any ligand; M1 indicates cells exposed to MIC1; T3 indicates cells exposed to TGFb3. As can be seen, PTP1B expression is significantly reduced in cells exposed to TGFb3 compared to the control cells, showing the effect of TGFb3 on PTP1B expression.

FIG. 4B shows fluorescence microscopy pictures of M2 macrophage cells on which in situ PLA (isPLA) has been performed to identify TBK1 expression. The top panel is an image of control M2 cells not exposed to any ligand; the bottom panel is an image of M2 cells exposed to 10 ng/ml TGFb1 overnight. The cell nuclei were visualised using DAPI (large blotches on the background), and spots around the nuclei indicate TBK1, detected by the isPLA method.

FIG. 5 shows isPLA images of TGFb1/2/3 and CLPTM1 interaction in the indicated cancer cells. A) Human stomach cancer. B) Mouse syngenic liver cancer. C) Human kidney cancer metastasis. D) Bladder cancer.

FIG. 6 shows that the AbCam anti-CLPTM1 mAb and GDF15 induce changes in the secretion profile of cytokines measured by Proseek (Olink Proteomics) by PBMC. FIG. 6A—Exosomes collected by ultracentrifugation from conditioned media and lysed in Triton x-100 from MCF7 cells stimulated with GDF15 (data values for Ep-CAM are shown). Expression levels for a negative control are also shown. FIG. 6B—PBMC cells stimulated with the AbCam anti-CLPTM1 mAb. Expression levels for a negative control and IgG control are also shown.

FIG. 7 shows changes in the secretion of certain proteins by NK-92, PBMC and MCF7 cells induced by the AbCam anti-CLPTM1 mAb, GDF15 and TGF-β3. Data is the fold induction over baseline (control).

Figure 10:
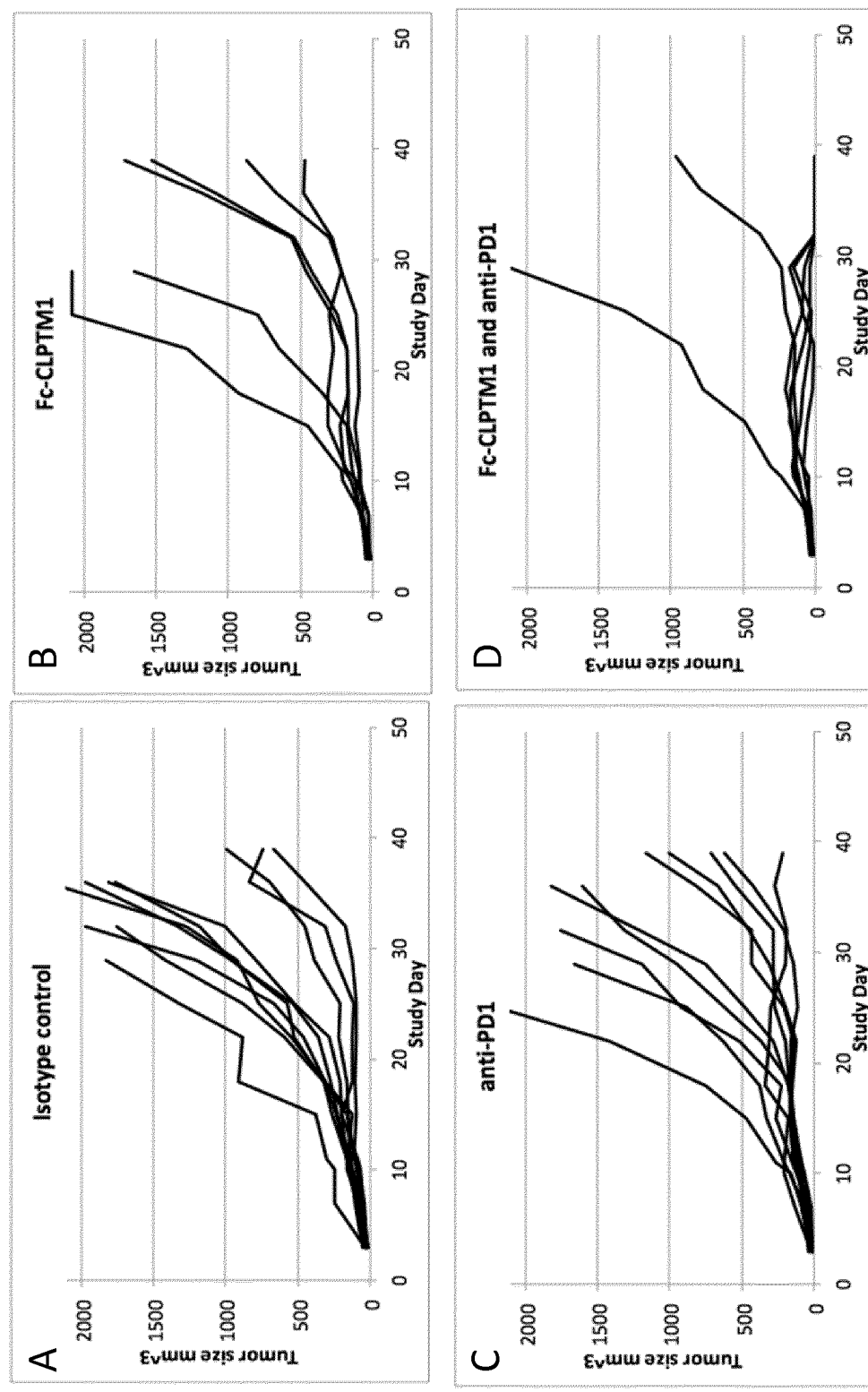

FIG. 10 shows tumour growth in a EMT6 syngeneic breast cancer model in mice, and the effect of Fc-CLPTM1 fusion protein, anti-PD1 antibody and combination therapy on tumour growth. A) Isotype control. B) Fc-CLPTM1 fusion protein treatment. C) Anti-PD1 treatment. D) Fc-CLPTM1 fusion protein/anti-PD1 combination therapy.

EXAMPLES

Example 1

CLPTM1 Binding to TGFb

Background

We had previously detected that GDF15 interacted with CLPTM1 in TAP-MS screen. As we realized that GDF15 and TGFB1,2,3 had similar effects on repression of pro-inflammatory cytokines, and inhibition of cell surface levels of HLA-DR, we sought to investigate if these ligands could interact with CLPTM1.

Materials and Methods

Biotinylated synthetic peptide fragments from CLPTM1 (JPT peptides, Germany) were immobilized in a streptavidin 96 well plate (#15500 Pierce) at 1 µM in PBS over night at +4° C. Plate was then washed 4 times in 300 µl PBS with 0.05% tween-20 (wash buffer). The plate was then blocked with PBS 1% BSA and 0.05% tween-20 (blocking buffer) for 1.5 hours at room temperature, then washed 4 times in wash buffer. Ligands GDF15, TGFb1, TGFb2 and TGFb3 (Abcam) were added in blocking buffer at 100 ng/ml and incubated at room temperature for 2 hours. The plate was then washed 8 times in 300 µL wash buffer with 2× NaCl. An anti-GDF15 antibody was added at 1 µg/ml (R&D Systems, goat polyclonal) or a pan-specific anti-TGFb antibody (R&D Systems, mouse 1 D11), and the plate incubated in blocking buffer for 1 hour at room temperature followed by washing with 4×300 µl wash buffer. HAF017 anti-goat-HRP antibody (to detect the anti-GDF15 antibody) or Santa Cruz sc-2005 Goat anti-mouse-HRP (to detect the pan-specific anti-TGFb antibody) was added and the plate incubated for 1 hour in blocking buffer followed by a wash. TMB substrate was added and stopped after 15 minutes with $H_2SO_4$. OD 450-620 was measured in an ELISA reader.

Results

Figure 1:
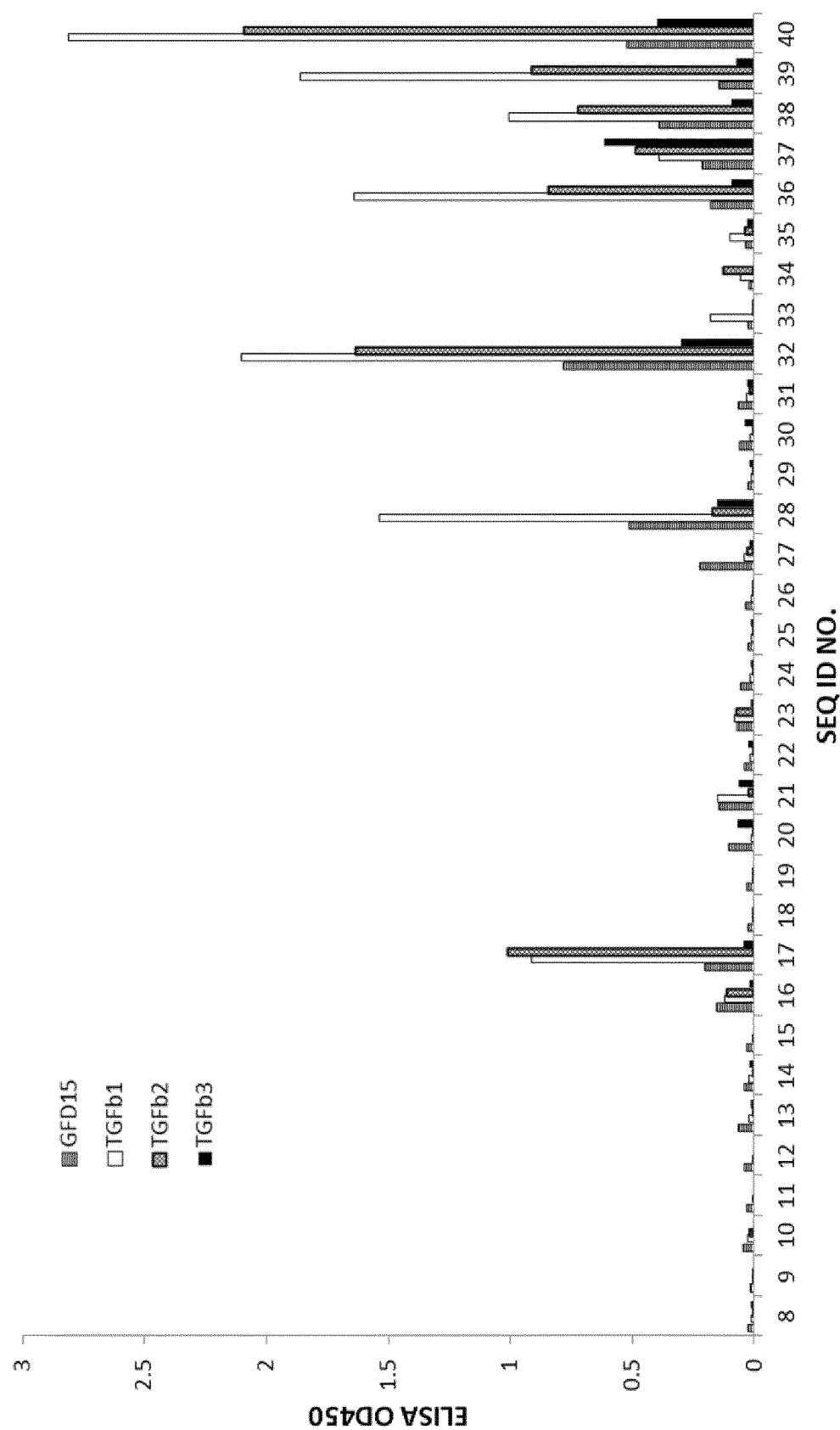

The results of the ELISA are shown in Table 3 below, and the graph in FIG. 1.

TABLE 3

| SEQ ID NO. | CLPTM1 Peptide Fragment Sequence | ELISA OD$_{450}$ | | | |
|---|---|---|---|---|---|
| | | GDF15 | TGFb1 | TGFb2 | TGFb3 |
| 8 | AAAQEADGARSAVVAAGGGSG | 0.022 | 0.012 | 0.010 | 0.015 |
| 9 | SGQVTSNGSIGRDPPAETQPG | 0.009 | 0.002 | 0.001 | 0.001 |
| 10 | QNPPAQPAPNAWQVIKGVLFG | 0.042 | 0.026 | 0.013 | 0.0060 |
| 11 | RIFIIWAISSWFRRGPAPQDG | 0.026 | 0.008 | −0.003 | 0.003 |
| 12 | QAGPGGAPRVASRNLFPKDTG | 0.034 | 0.003 | −0.006 | 0.004 |
| 13 | LMNLHVYISEHEHFTDFNATG | 0.058 | 0.020 | 0.005 | 0.014 |
| 14 | SALFWEQHDLVYGDWTSGENG | 0.034 | 0.022 | 0.002 | 0.020 |
| 15 | SDGCYEHFAELDIPQSVQQNG | 0.024 | 0.006 | −0.003 | 0.004 |
| 16 | GSIYIHVYFTKSGFHPDPRQG | 0.149 | 0.122 | 0.107 | 0.020 |
| 17 | KALYRRLATVHMSRMINKYKG | 0.197 | 0.913 | 1.006 | 0.046 |

TABLE 3-continued

| SEQ ID NO. | CLPTM1 Peptide Fragment Sequence | ELISA OD$_{450}$ | | | |
|---|---|---|---|---|---|
| | | GDF15 | TGFb1 | TGFb2 | TGFb3 |
| 18 | RRRFQKTKNLLTGETEADPEG | 0.021 | 0.002 | 0.002 | 0.004 |
| 19 | MIKRAEDYGPVEVISHWHPNG | 0.028 | 0.006 | 0.002 | 0.004 |
| 20 | ITINIVDDHTPWVKGSVPPPG | 0.098 | 0.011 | 0.005 | 0.068 |
| 21 | LDQYVKFDAVSGDYYPIIYFG | 0.140 | 0.152 | 0.019 | 0.065 |
| 22 | NDYWNLQKDYYPINESLASLG | 0.038 | 0.017 | 0.005 | 0.025 |
| 23 | PLRVSFCPLSLWRWQLYAAQG | 0.063 | 0.083 | 0.066 | 0.016 |
| 24 | STKSPWNFLGDELYEQSDEEG | 0.053 | 0.018 | 0.007 | 0.012 |
| 25 | YEQSDEEQDSVKVALLETNPG | 0.022 | 0.010 | 0.007 | 0.014 |
| 26 | LWRWQLYAAQSTKSPWNFLGG | 0.033 | 0.013 | 0.008 | 0.011 |
| 27 | YPINESLASLPLRVSFCPLSG | 0.220 | 0.043 | 0.025 | 0.018 |
| 28 | GDYYPIIYFNDYWNLQKDYYG | 0.507 | 1.536 | 0.164 | 0.151 |
| 29 | WQVIKGVLFRIFIIWAISSWG | 0.023 | 0.010 | 0.006 | 0.019 |
| 30 | RNLFPKDTLMNLHVYISEHEG | 0.055 | 0.015 | 0.009 | 0.041 |
| 31 | FTDFNATSALFWEQHDLVYGG | 0.061 | 0.032 | 0.014 | 0.029 |
| 32 | SGDYYPIIYFNDYWNLQKDYYPINESLASLPLRVSFCPLS | 0.779 | 2.102 | 1.630 | 0.300 |
| 33 | LWRWQLYAAQSTKSPWNFLGDELYEQSDEEQDSVKVALLETNP | 0.021 | 0.177 | 0.009 | 0.007 |
| 34 | ARSAVVAAGGGSSGQVTSNGSIGRDPPAETQPQNPPAQPA | 0.016 | 0.058 | 0.123 | 0.003 |
| 35 | NAWQVIKGVLFRIFIIWAISSWFRRGPAPQDQAGPGGA | 0.029 | 0.098 | 0.031 | 0.027 |
| 36 | DTLMNLHVYISEHEHFTDFNATSALFWEQHDLVYGDWTSG | 0.174 | 1.639 | 0.838 | 0.095 |
| 37 | TKSGFHPDPRQKALYRRLATVHMSRMINKYKRRRFQKTKN | 0.209 | 0.389 | 0.483 | 0.613 |
| 38 | VSGDYYPIIYFNDYWNLQKDYYPINESLASLPLRVSFC | 0.383 | 1.006 | 0.717 | 0.091 |
| 39 | PLDQYVKFDAVSGDYYPIIYFNDYWNLQKDYYPINESLA | 0.137 | 1.864 | 0.910 | 0.074 |
| 40 | SGDYYPIIYFNDYWNLQKDYYPINESLA | 0.518 | 2.810 | 2.091 | 0.399 |

The data indicate the presence of various binding sites for different TGF-β ligands. For example using the cut-off 0.098, or in another case 0.177, peptides which bind to the various ligands can be identified. The skilled person is readily able to interpret the data and identify an appropriate cut-off value to identify peptides which bind to the ligands with higher or lower affinity. Further the data suggest the presence of a previously unknown binding site for the listed TGFb superfamily ligand members to CLPTM1. The motif includes a double DYYPI (SEQ ID NO: 41) motif, present in several of the peptides used in the above assay. We suggest the possibility that multimerised such DYYPI (SEQ ID NO: 41) motifs would be a therapeutic option to inhibit excess soluble TGF-β ligands in pathological conditions where the ligands are overexpressed.

Example 2

Inhibition of TGFb Signalling Through CLPTM1 by Antagonistic Antibody Fragments
Background
Inhibiting TGFb (TGFb1, TGFb2, and/or TGFb3) signalling with an antagonistic CLPTM1-binding therapeutic antibody will be useful as an immune checkpoint inhibitor. Such antibodies may block cancer cells' inhibition of the immune system found around tumours. This will give the immune system a greater chance of fighting the non-self cancer cells, optionally in combination with other immune modulatory cancer treatments such as inhibitors of PD1/PDL1 or CTLA4 signalling.

It decided to develop a monovalent blocking binder of CLPTM1 to inhibit TGF-β signalling as the receptor may signal through dimerization. We therefore cleaved a CLPTM1 mouse monoclonal antibody into monovalent Fab fragments and evaluated its antagonistic potential.

Materials and Methods
4F5 Fab Development
4F5 monoclonal IgG antibody against CLPTM1 was raised against CLPTM1 peptide #6 (QKALYRRLATVHM-C) (SEQ ID NO242, or SEQ ID NO:241 comprising a C-terminal cysteine residue) using the Rapid-Prime™ method from ImmunoPrecise (Victoria, Canada). 4F5 is a mouse IgG2a.

The antibody was enzymatically cleaved into Fab-fragments using Pierce™ Fab Micro Preparation Kit (44685) in accordance with the manufacturer's instructions. The final Fab concentration was quantified by its $OD_{280}$ using a NanoDrop spectrophotometer.

ELISA measurement of TNFα was performed using MabTech TNFα ELISA (3510-1H-6) according to the manufacturer's instructions.

Cell Isolation, Selection and Culture

A heparinized peripheral blood sample was diluted 1:1, placed on a Ficoll Paque Plus, and centrifuged at 400×g for 30 minutes. The PBMC layer was transferred into a 50 ml tube of PBS and centrifuged for 7 min at 250×g. CD14+ cells were isolated using an EasySep™ CD14 Positive Selection kit (STEMCELL Technologies Inc., Canada) according to the manufacturer's protocol. Cell culture was performed in 48-well cell culture plates. Each well was seeded with 300 µl cell suspension at $8.33 \times 10^5$ cells/ml in RPMI medium. CD14+ cells were allowed to adhere for 90 minutes at 37° C. in an incubator, after which non-adherent cells were removed. Macrophages were grown for 7 days before use in assays.

Antibody, Fab fragments, and TGFb1, 2, or 3 (R&D systems) were added to cell culture media of cultured macrophages for 24 hours prior to 4 hour stimulation with LPS. Cell culture media was then harvested and analyzed for TNFα content.

Results

Figure 2:
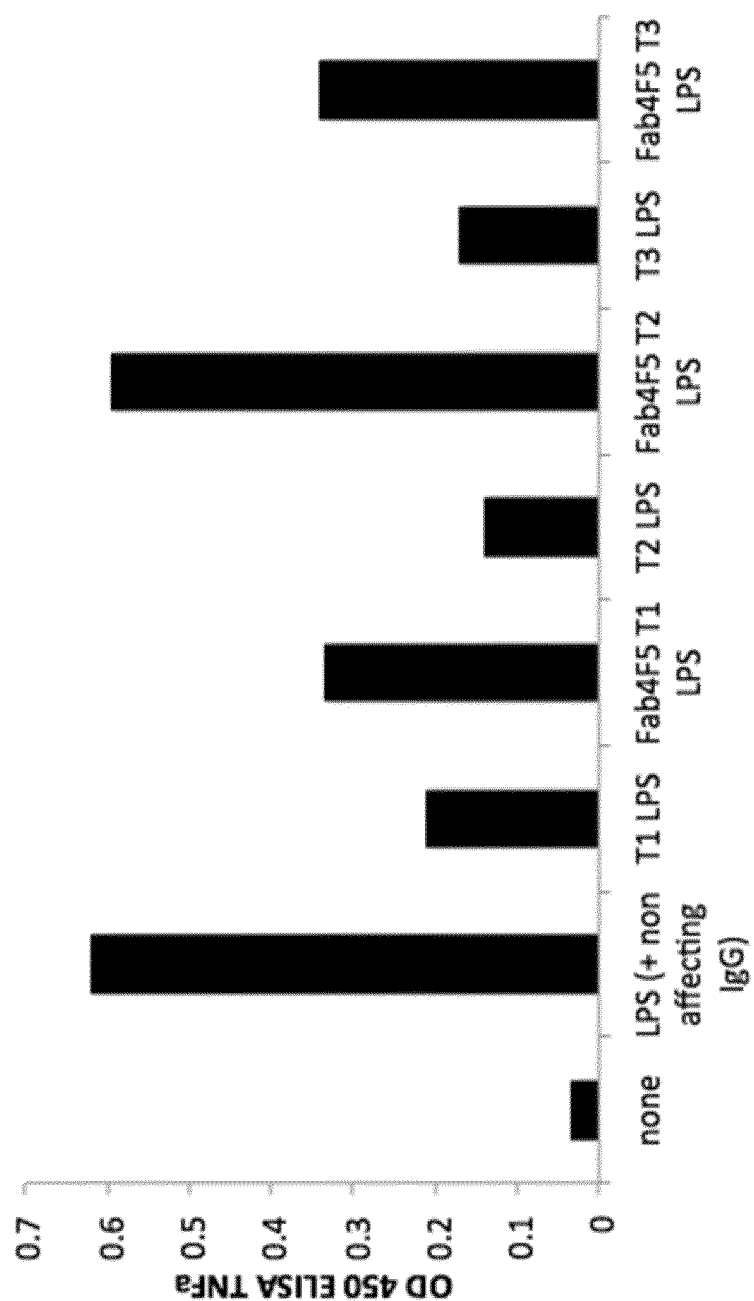

Human macrophage cultures were subjected to immune suppressive ligands TGFb1, 2, or 3 at 50 ng/ml with or without 4F5 Fab fragments to CLTPM1 at 50 µg/ml. This culture was grown for 24 hours and then subjected to 4 hours of LPS stimulation. Measurement of TNFα release shows a strong immune suppressive effect of the TGFbs, which is partly reversed by the presence of Fab4F5 for TGFb1 and TGFb3 and almost completely reversed for TGFb2, as shown in FIG. 2.

Example 3

TGFB Ligand-Induced Degradation of PTP1B and TBK1 is Dependent on CLPTM1

Background

We identified that TGFb1 ligands induced degradation of Protein Tyrosine Phosphatase 1 (PTP1B) and Tank-Binding Kinase 1 (TBK1). These are crucial proteins in immune regulation processes such as HLA-DR and Interferon signalling. TBK1 is also involved in CD40 signalling.

Materials and Methods

The J774.2 murine macrophage cell line was purchased from Sigma. The cells were maintained in DMEM supplemented with 10% FBS, 200 mM L-Glutamine and Pen-strep. The cells were transfected with RNAiMAX (Invitrogen) at 25 pMol per 6-wells. The siRNA was pre-diluted in Opti-MEM reduced serum media according to the manufacturer's instructions prior to adding to the cells. The pre-validated siRNA was purchased from Invitrogen (Silencer® Select, s3186), and known to target murine CLPTM1.

After 48 hrs the cells from each transfection were split into 6 individual 12-well plates (half a 12-well plate each) and allowed to settle for 24 hrs before ligand treatments for 18 hrs. Ligands were applied at the following concentrations: MIC1 (1 µg/ml), TGFB1, 2, and 3 at 10 ng/ml, and a positive control ligand at 1 µg/ml. The cells were lysed on ice in PBS supplemented with 1% Triton X-100 and 1× Roche complete protease inhibitor cocktail.

After lysis, the cells were scraped from the plates, and the supernatant of the lysate was collected by centrifugation at 13000×g for 10 mins and loaded onto gels. The samples were run at 100 V on 4-12% gradient gels, then transferred to membranes using a Trans-Blot® Turbo™ Transfer System (Biorad) with the default mixed program (7 min). The transferred samples were blocked in PBS supplemented with 3% BSA for 1 hr at RT. Goat-anti-PTP1B antibody (R&D Systems) against PTP1B was incubated at 1 µg/ml in PBS under mild agitation o/n in a cold room. After extensive washes in PBST (PBS with 0.05% Tween-20) anti-goat-HRP secondary (R&D Systems) was added at 1:2000 dilution for 50 minutes.

Rabbit Anti-NAK/TBK1 antibody (EPR2867(2)-19 Abcam) was added at 1 ug/ml in PBS under mild agitation o/n in a cold room. After extensive washes in PBST (PBS with 0.05% Tween-20) anti-rabbit-HRP secondary (R&D Systems) was added at 1:2000 dilution for 50 minutes.

After extensive washes in PBST, HRP activity on the membranes was visualised using a CCD camera (Bio-Rad). The membranes were then stripped in 2.5 M Glycine supplemented with 1% SDS for 45 min at RT, washed in PBST and blocked again in 3% BSA before re-probing with rabbit anti-GAPDH antibody diluted 1:5000 (Sigma), and anti-rabbit antibody (R&D Systems) diluted 1:2000. HRP activity on the membranes was then again detected on a CCD (Biorad) unit.

Results

Figure 3:
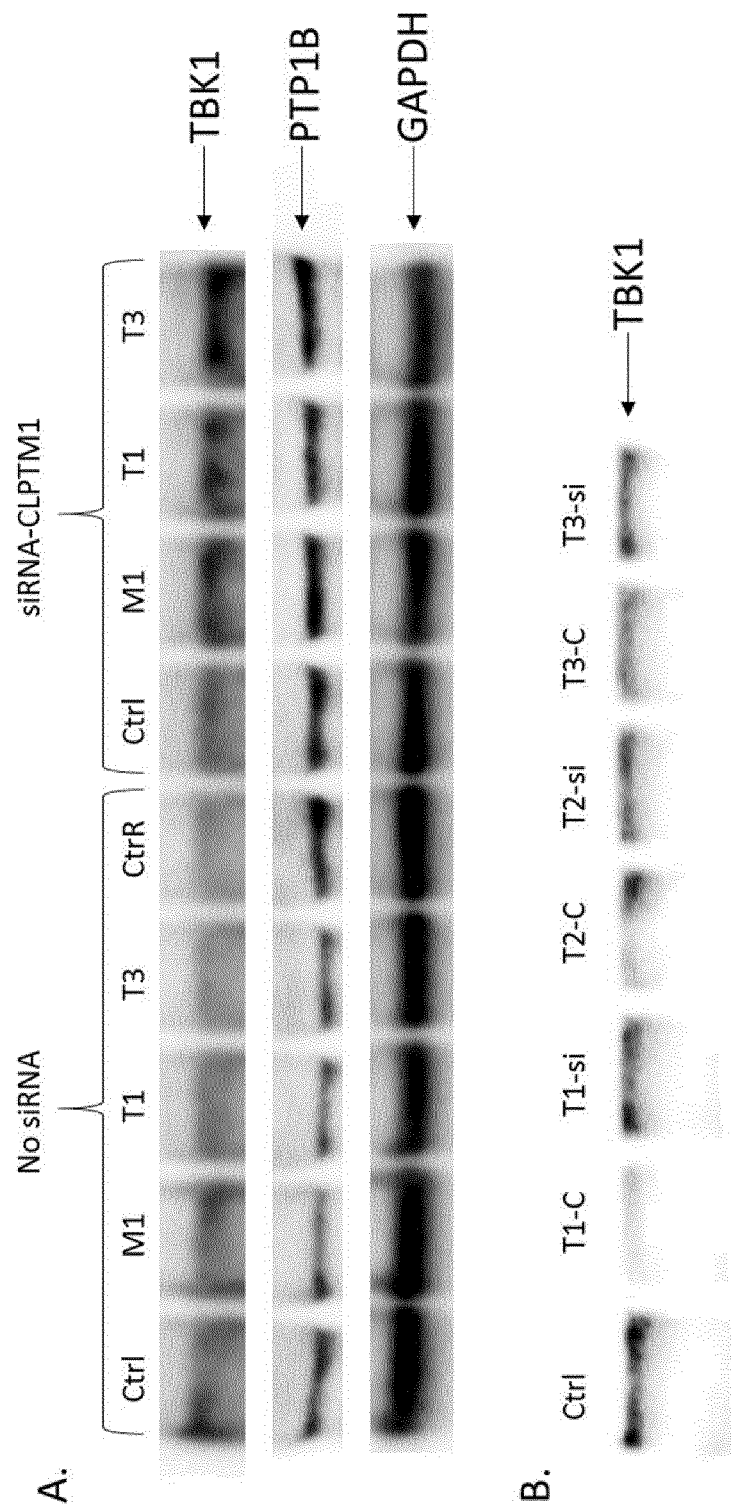

We reduced cellular levels of CLPTM1 using siRNA, and noticed that the ability of the ligands to reduce total amounts of PTP1B and TBK1 was reduced (FIG. 3). From this discovery we suggest that an antibody or antibody fragment that blocks ligand binding to the receptor has the potential to reverse TGFB1, 2, and 3 ligand-induced immune suppression on pathways downstream of CLPTM1, such as PTP1B and TBK1.

Example 4

TGFb Ligand Stimulation of Human M2 Macrophages and MCF7 Breast Cancer Cells Reduces PTP1B and TBK1

Background

In order to investigate if TGFb1 ligands also induced reduction of PTP1B and TBK1 in macrophages polarized towards M2 and human MCF7 breast cancer cells we stimulated such cells with the ligands.

Materials and Methods

Cell Culture

Human primary M2 polarized macrophages was derived from PBMC obtained from healthy volunteer blood donors. CD14+ cells were isolated using an EasySep CD14 Positive Selection Kit, maintained in RPMI-1640 medium supplemented with 10% FBS, L-Glutamine and Pen-strep. Cells were cultivated for 6 days in the presence of 50 ng/ml recombinant macrophage colony-stimulating factor (M-CSF, R&D Systems) in order to polarize the cells towards an M2 subtype.

MCF7 was cultivated in DMEM/F12 medium with pen-strep, L-glutamine and 10% FBS. The MCF7 cells were starved o/n in DMEM/F12 medium with low serum (0.5% FBS) prior to ligand stimulation.

For in situ proximity ligation assay (isPLA) experiments the cells were re-plated into 8-well slides (Lab-Tek™ II Chamber Slides, Thermo Fisher).

Cells were stimulated with either TGFB1, TGFB2, TGFB3 at 10 ng/ml. For isPLA, new medium was added, with individual ligands added to separate wells, and the cells incubated o/n prior to fixation in 3% formaldehyde solution for 20 minutes on ice the following day. Fixed cells were washed extensively in PBS and lysed in PBS with 1% Triton at room temperature for 20 minutes. The cells were blocked with Duolink blocking solution (Sigma) and primary antibodies at 1 µg/ml were added o/n. Subsequent steps including extensive washes (5 times 10 minutes on shaking table) in PBST were done using the Duolink isPLA protocol according to manufacturer's instruction (Duolink detection kit Red). Finally, the slides were washed extensively in PBS on an shaking table under a light protective lid, and mounted using slow fade Gold supplemented with DAPI. The slides were analysed using a Zeiss inverted epiflouroscence microscope set at 20× magnification. DAPI, FITC and CY3.5 channels were recorded. Images were obtained using Z-stacks (Axiovision software).

Antibodies

Antibodies used were anti-PTP1B (AF13661, R&D Systems) anti-TBK1 (Anti-NAK/TBK1 antibody (EPR2867(2)-19], Abcam) and anti-GAPDH (Sigma).

Western Blot

MCF7 cells were grown in 6-wells, serum starved (0.5% FBS in media) o/n prior to ligand stimulation. Cells were lysed on ice in 1% Triton in PBS with complete protease inhibitor (Roche) added. Cells were scraped, collected and lysates cleared by centrifugation on a pre-cooled table top centrifuge at 13000 RPM for 10 minutes prior to boiling in loading dye with reducing agent and loading on a 4-12% gradient gel. The material was transferred using the Tank Turbo transblotter system (Biorad), blocked in 3% BSA and incubated with a-PTP antibody at 1 ug/ml in PBS o/n under mild agitation in cold room. Detection by secondary HRP labelled antibody at 1:2000 dilution and CCD camera. Membranes were stripped using Glycine solution, re-blocked in 3% BSA and re-probed using a-GAPDH and secondary HRP antibody.

Results

Figure 4:
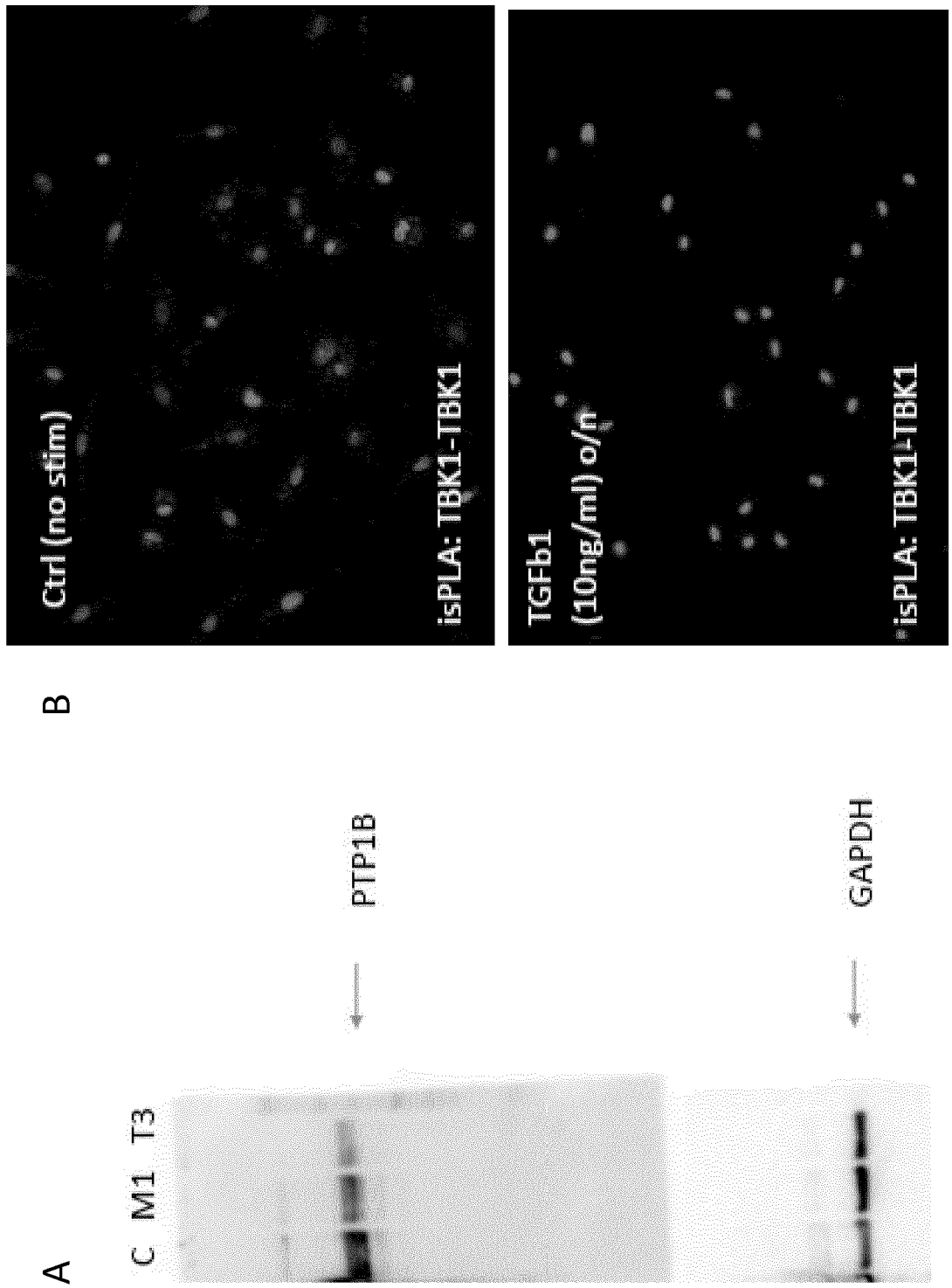

TGFb3 reduced PTP1B in MCF7 cells, as shown in FIG. 4a, in which the cells treated with TGFb3 contained significantly less PTP1B than the untreated control cells. TGFb1 reduced TBK1 in M2 polarized macrophages, as shown in FIG. 4b. In FIG. 4b the DAPI stained nuclei can be seen: in the top panel, showing control cells not treated with any TGFb ligand, many of the nuclei are surrounded by dots, representing TBK1; in the bottom panel, showing cells treated with 10 ng/ml TGFb1 o/n, few of the cells contain detectable TBK1. This clearly shows that TGFb1 treatment of M2 macrophages resulted in a reduction of their TBK1 content.

Example 5

Identification of CLPTM1-TGFB1/2/3 PLA in Human Metastatic Cancers

Background

In order to select future indications for therapeutic niches where the TGFB1/2/3-CLPTM1 axis could be of importance we investigated a set of human metastases from various cancers. We also investigated a set of mouse syngenic models.

Materials and Methods

Tissue Microarrays (TMAs)

Figure 5:
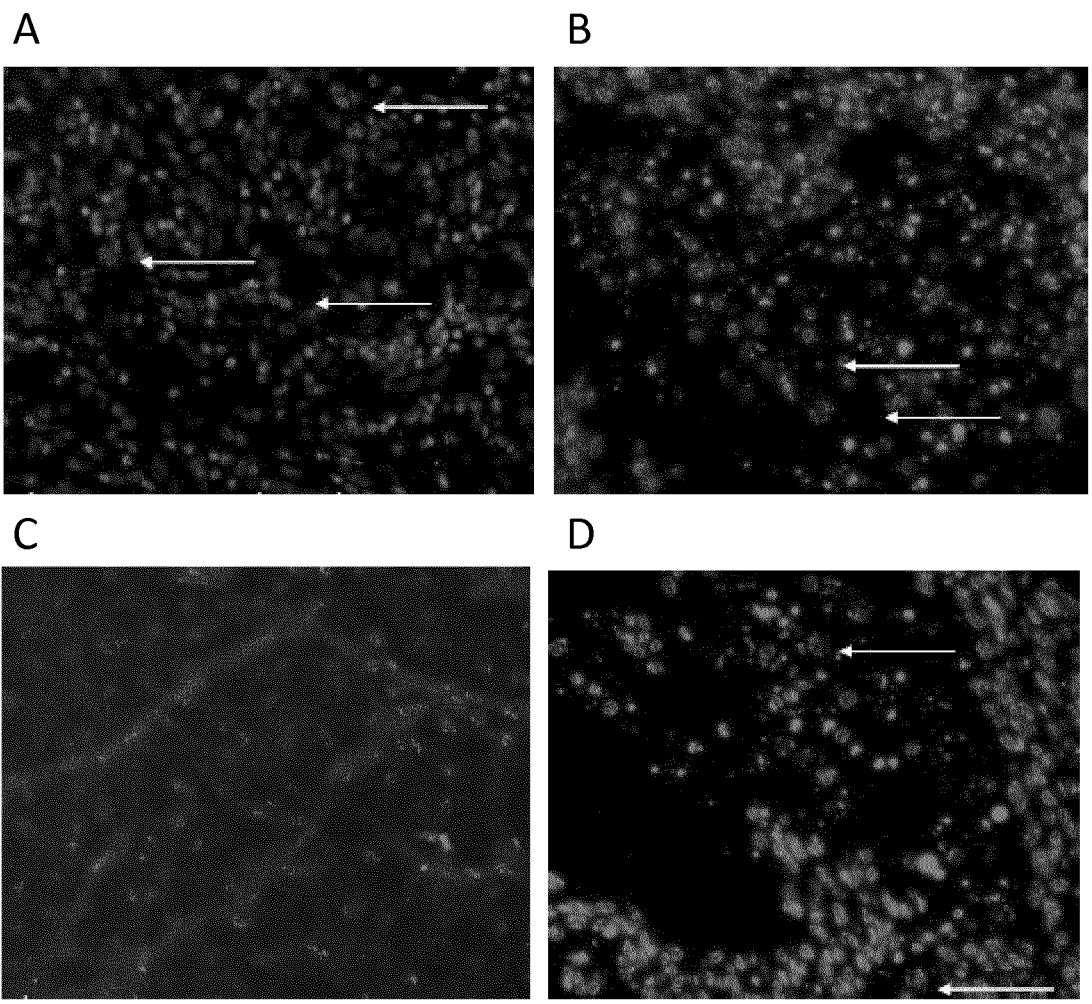

The following tissue materials were investigated: from mouse syngenic models the Crown Biosciences array (images as examples are displayed in FIG. 5 parts B and D); for human cancers the MT2081 (US Biomax) was used. Examples are shown in FIG. 5 parts A and C.

Slides were processed by deparaffinization and antigen retrieval at core facility SciLife, Uppsala and washed in PBST. Border edges were sealed with fat pen and incubated in blocking solution (Duolink, Olink Biosciences) o/n.

3 µg/ml of each primary antibody (anti-TGFB1: C-16, Santa Cruz; anti-CLPTM1: bs-8018R, Bioss Antibodies) was mixed together in antibody diluent buffer (OLINK) and added to the slides, which were incubated o/n in coldroom. The slides were extensively washed in PBST (PBS, 0.05% tween20) under mild agitation on an orbital shaking tray. Secondary Duolink probes (anti-goat and anti-rabbit) were mixed at 1:6 dilution of each probe, and incubated in a moisture chamber for 60 min at 37° C. After extensive washes on an orbital shaking tray in PBST, ligation and rolling circle amplification was performed according to manufacturer's instruction (Duolink, Sigma). The Duolink detection kit Red was used.

Finally, the slides were washed extensively in PBS on an orbital shaking table under a light protective lid, and mounted using slow fade Gold with DAPI. The coverslips on the slides were fixed using nail polish. The slides were analysed using a Zeiss inverted epiflouroscence microscope set at 20× magnification. DAPI, FITC and CY3.5 channels were recorded. Images were obtained using Z-stacks (Axiovision software) and obtained csv files were merged and exported.

Results

We identified a large number of human cancers to be positive for CLPTM1-TGFB1/2/3. These are shown in Table 4, below.

The TGFb antibody used in this study detects all three TGFB forms (1-3) and as we previously demonstrated that all three ligands are capable of binding to CLPTM1, we identified a set of therapeutic possibilities for late stage human disorders where the staining intensity is medium or high, such as squamous cancers of the lung and larynx, adenocarcinoma of the stomach and colon, kidney, pancreas, bladder, prostate and breast. As exemplified in FIGS. 5(A and C) we observed highly positive infiltrative cells with polarized (one side of the cell) staining for CLPTM1-TGFB1/2/3. We do not exclude the presence of CLPTM1 on certain tumour cells as well. The dual expression on immune cells and tumour cells resembles some other known immune check point proteins, such as PD-L1. As we have previously observed that the tumour environment increases cell surface levels of CLPTM1 several fold, we suggest that a biologic agent, such as an antibody, would be suitable to block TGFB1/2/3 ligand accessibility to such cells. In another embodiment, fragments of, or the ectodomain of, CLPTM1 could be used to inhibit soluble TGFB1/2/3 in pathological conditions. Another approach would be to deplete the tumour and the tumour stroma of CLPTM1 positive cells, such as tumour cells and M2 polarized macrophages.

The detection of a novel TGFB receptor on the surface of innate immune cells, certain T-cells and tumour cells could be envisioned to serve as a biomarker for such approaches. As such cells can be detected in biopsies from tumours or metastases thereof or from circulation, such a biomarker can aid the treating clinician in decisions on therapy options.

TABLE 4

Staining intensity isPLA TGFB1,2,3-CLPTM1 as indicating selection for therapy

| Cancer Type | Staining Intensity Cancer Grade | | |
|---|---|---|---|
| | I | II | III |
| Squamous carcinoma (larynx met) | | | 4(4) |
| Lung Squamous carcinoma | | | 2(2) |
| Lung Adenocarcinoma | 6(6) | | |
| Stomach adenocarcinoma | 1(6) | 2(6) | 3(6) |
| Duodenum adenocarcinoma | 2 (lymph nodes) | 1 | 1 (mesentery) |
| Rectal adenocarcinoma (liver mets) | | | 3 |
| Small intestine adeno | | 1 | |
| Colon adeno mets | | | 2 (+2 in lymph node mesentary-small cells) |
| Esophagus squamous | 1 (lymph node) | 1 | |
| Kidney clear cell met | | | 3(3) |
| Prostate met | 1 | | 1 |
| Pancreas met | 1 (lymph node) | 2 (lymph node) | 3 |
| Bladder (met) transitional cell carcinoma | 1 (lymph node) | | 2 |
| Ovary adeno met | 3 | | 1 |
| Endometrium adeno | 3 | 1 | 1 |
| Cervix adeno | 1 (lymph node) | | 1 (lymph node-pelvic) |
| Cervix squamous | 1 (lymph node) | 1 | 1 |
| Penis can squamous | 1 | | |
| Breast (ductal invasive) | | 4 | 2 |
| Thyroid papillary | 6 (5 of these lymph node) | | |
| Melanoma | 1 (lymph node) | 2 | |
| Squamous skin ca (met) | 3 (2 of these lymph nodes) | | |
| Ovary serous papillary adeno | 4 | | |

Example 6

Alteration of the Secretome by CLPTM1 Agonists
Materials and Methods
Proseek
Secreted proteins from cell cultures where quantified using multiplexed proximity extension assay, Proseek (Assarsson E et al PlosOne 2014) by Olink Proteomics AB (Uppsala Sweden). Data is presented as Normalized Protein Expression (NPX log 2-scale). The Oncology I v2 92-plex panel was run.

Cell Culture and Cell Stimulation Experiments
A cell suspension of heparinized peripheral blood was diluted 1:1 and placed on a Ficoll Paque Plus. Cells were centrifuged at 400×g for 30 minutes and the PBMC layer was transferred to a 50 ml tube of PBS and centrifuged for 7 min at 250×g.

CD14+ cells were isolated using EasySep CD14 Positive Selection kit according to the manufacturer's instructions.

Cell culture was performed in 48 well cell culture plates, which were seeded with 300 µl cell suspension per well at $8.33 \times 10^5$ cells/ml in RPMI medium. CD14+ cells were allowed to adhere for 90 minutes at 37° C. in an incubator and non-adherent cells were removed.

NK-92 cells were cultured in RPMI-1640 supplemented with 10% FBS, 12.5% Horse serum, L-glutamine, IL2 and 3-mercaptoethanol.

MCF7 cells were cultured in serum-free conditions (No FBS added to DMEM) overnight prior to ligand stimulation, and media was replaced 3 times before stimulation to avoid exosomes from FBS. Cells were either treated with control (PBS) or biologically active GDF15 (Abcam) at 1.5 µg/ml for 1 hr at 37° C.

For analyses of exosomes in FIG. 6A, conditioned medium was pre-cleared by centrifugation at 14,000×g for 10 min at 4° C., followed by filtration with a 0.45 µM filter to avoid contaminants from cell debris, followed by ultracentrifugation at 100,000×g for 2 hrs. Pelleted exosome fraction was lysed with 1% Triton X-100 at 4° C., samples diluted in order to have 0.3% Triton concentration and analysed by Proseek multiplex panel as described above.

Results
The expression of a number of anti-inflammatory cytokines and other secreted proteins was found to be elevated following exposure to TGF-β3, GDF15 or the AbCam anti-CLPTM1 antibody.

Figure 6:
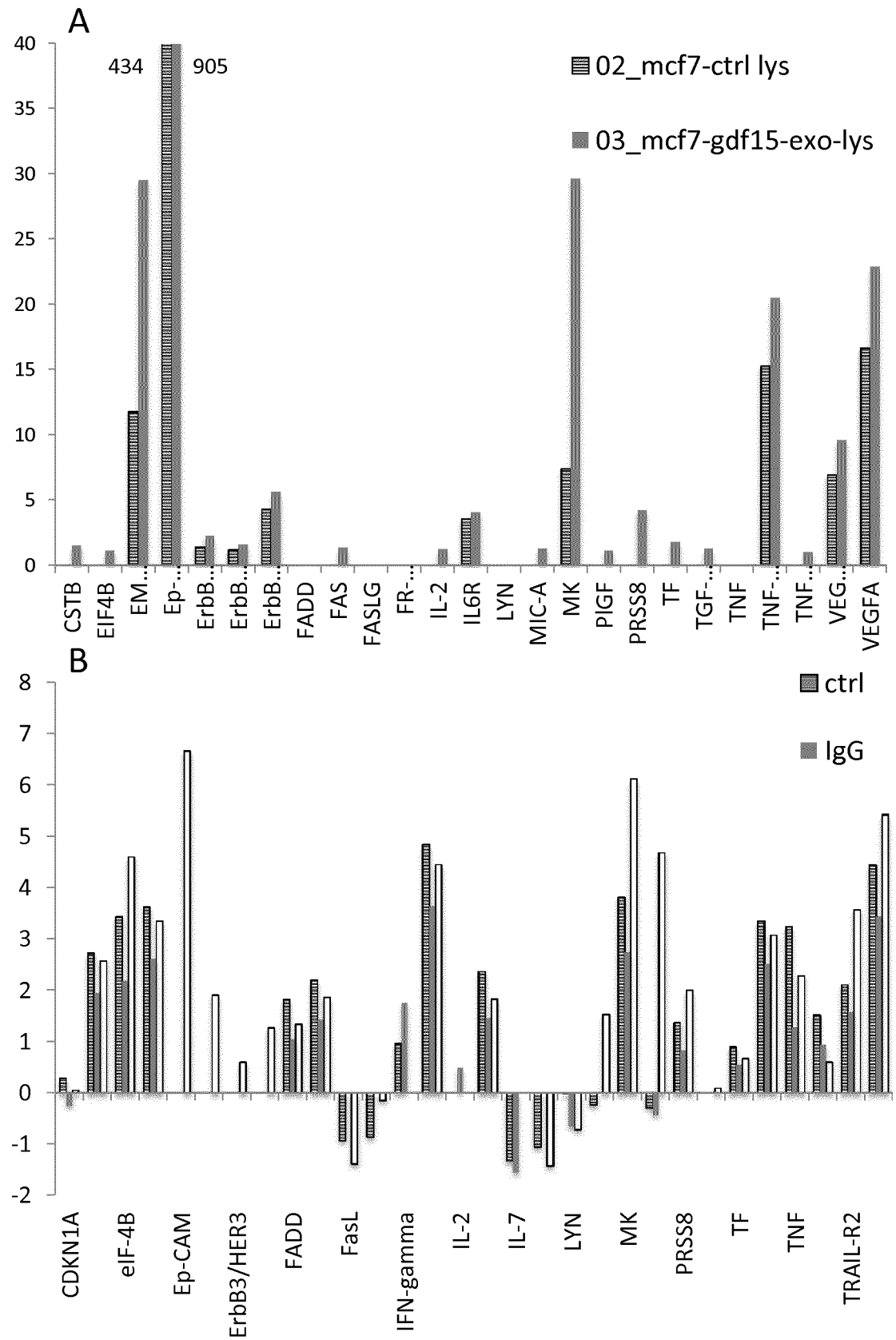
Figure 8:
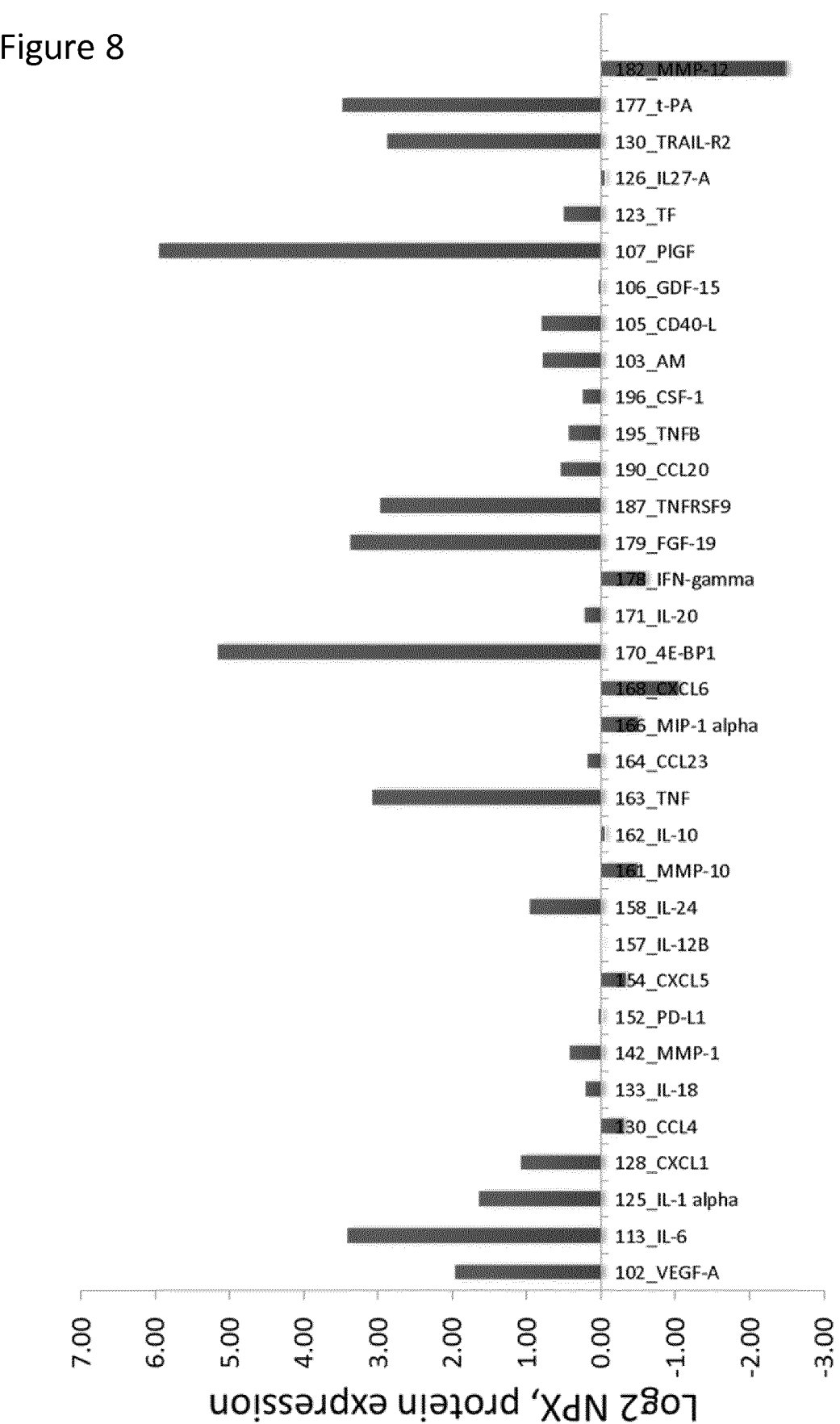
FIG. 8 shows changes in cytokine expression by PBMC culture caused by the AbCam anti-CLPTM1 mAb.

Midkine (MK) expression was increased by both GDF15 and the AbCam antibody (FIG. 6). GDF15, PIGF, Trail-r2, LAP-TGF-β1, MIC-A and HB-EGF were all increased by the AbCam anti-CLPTM1 antibody in NK-92 culture, and HB-EGF was also increased by GDF15 in PBMC culture and by the AbCam antibody in MCF7 culture. Caspase-3, MIC-A and TNF-R1 were also increased by the AbCam antibody in MCF7 culture (FIG. 7). IFNγ expression was reduced by GDF15 in PBMC culture (see FIG. 7). FIG. 8 also demonstrates the effect of the antibody on the secretion of various proteins. MMP-12 was reduced in PBMC culture by the AbCam anti-CLPTM1 antibody (FIG. 8).

In a similar manner, the expression of a number of pro-inflammatory cytokines was decreased by TGF-β3. CXCL9 and CXCL11 secretion were reduced by TGFβ3 in PBMC culture. Furthermore, the level of Caspase-3 secretion was increased by TGFβ3 in NK92 culture in a similar manner to the antibody described above. This demonstrates that TGFβ can alter the level of expression of various secreted proteins in a similar manner to GDF15, another ligand for CLPTM1, as well as an agonistic antibody.

Example 7

In Vitro Effect on Cytokine Production by CLPTM1 Fusion Proteins

A CLPTM1-fusion protein was designed comprising N-terminal to C-terminal: amino acids 104-352 of the ECD of human CLPTM1 (SEQ ID NO: 243) linked by 4 repeats of the GGGGS linker (SEQ ID NO: 228) to the N-terminal of the Fc portion of an immunoglobulin (i.e. with the CLPTM1 ECD polypeptide at the N-terminus of the fusion protein and the Fc region at the C-terminus of the fusion protein). Amino acids at positions 201-203 of the CLPTM1 ECD (RRR) were substituted with AVG to remove any potential nuclear localisation signal and reduce any potential intracellular retention of the fusion protein product. The fusion protein was produced in CHO cells by Icosagen (Estonia) using QMCF-technology.

```
N-terminal-
NLHVYISEHEHFTDFNATSALFWEQHDLVYGDWTSGENSDGCYEHFAE
LDIPQSVQQNGSIYIHVYFTKSGFHPDPRQKALYRRLATVHMSRMINK
YKAVGFQKTKNLLTGETEADPEMIKRAEDYGPVEVISHWHPNITINIV
DDHTPWVKGSVPPPLDQYVKFDAVSGDYYPIIYFNDYWNLQKDYYPIN
ESLASLPLRVSFCPLSLWRWQLYAAQSTKSPWNFLGDELYEQSDEEQD
SVKVALLET (SEQ ID NO: 243)-(G4S)x4-Fc-IgG1
mouse.
```

CLPTM1-Fc In Vitro

Figure 9:
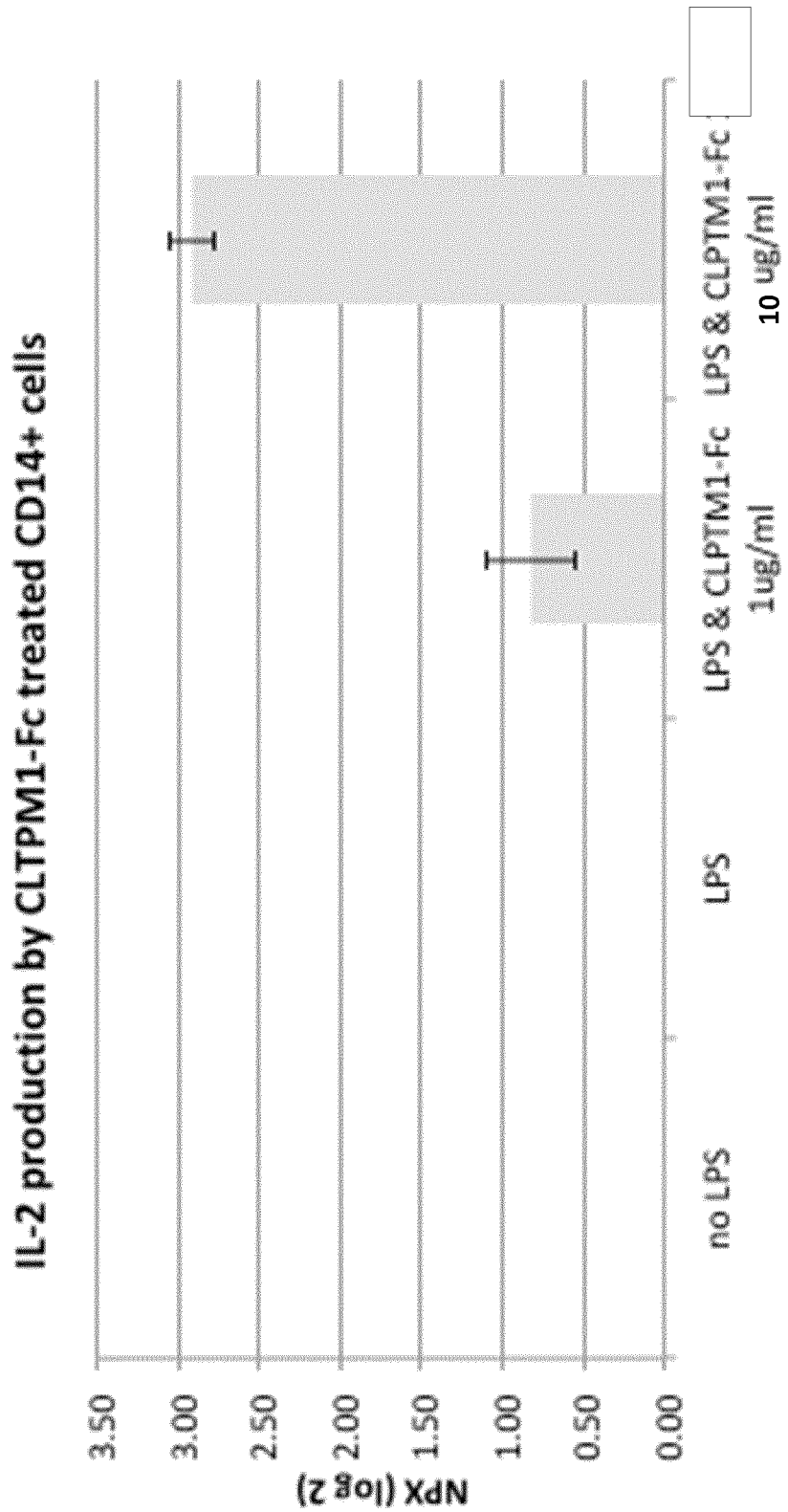
FIG. 9 shows the stimulation of IL2 secretion by CD14+ cells treated with CLPTM1-Fc fusion protein.

CD14+ cells were isolated from a healthy human donor and cultured in vitro as described in Example 4. The culture was grown for 24 hours in the absence or presence of CLTPM1-Fc fusion (C-terminal fusion) at 10 or 1 µg/mL. Then 1 µg/ml LPS was added and after 4 hours cell culture supernatants where taken and analysed by Multiplex PEA oncology v2 (Olink Proteomics Uppsala Sweden). The presence of the CLPTM1-Fc protein resulted in an increased production of IL-2 upon LPS stimulation with no detectable changes in other cytokines such as TNF, IL6, VEGF and others (FIG. 9). IL-2 drives the proliferation and differentiation of T-cells and NK-cells vital for a potent anti-tumour immune response. This illustrates the usefulness of a CLPTM1-Fc fusion for cancer treatment to potentially increase IL-2 production in the tumour micro environment enhancing T-cell proliferation. IL-2 therapy has been suggested as an effective immunotherapy of cancer (Rosenberg, J Immunol Jun. 15, 2014, 192 (12) 5451-5458).

Example 8

In Vivo Effect of CLPTM1 Fusion Protein on Breast Cancer Growth

A CLPTM1-fusion protein was designed comprising N-terminal to C-terminal: the Fc portion of an immunoglobulin linked by 4 repeats of the GGGGS linker (SEQ ID NO: 228) to the CLPTM1 peptide of Example 7 (i.e. with the Fc region at the N-terminus of the fusion protein and the CLPTM1 polypeptide at the C-terminus of the fusion protein. The fusion protein was produced in CHO cells by Icosagen (Estonia) using QMCF-technology.

```
N-terminal- Fc-IgG1 mouse-(G4S)x4-
                                    (SEQ ID NO: 243)
NLHVYISEHEHFTDFNATSALFWEQHDLVYGDWTSGENSDGCYEHFAE
LDIPQSVQQNGSIYIHVYFTKSGFHPDPRQKALYRRLATVHMSRMINK
YKAVGFQKTKNLLTGETEADPEMIKRAEDYGPVEVISHWHPNITINIV
DDHTPWVKGSVPPPLDQYVKFDAVSGDYYPIIYFNDYWNLQKDYYPIN
ESLASLPLRVSFCPLSLWRWQLYAAQSTKSPWNFLGDELYEQSDEEQD
SVKVALLET
```

In Vivo Efficacy Study

The EMT6 syngeneic breast cancer model in mice has previously been illustrated as responsive to TGFb inhibition alone and in combination with PDL1 inhibition (EP3105246A2 and David et al. OncoImmunology, 6:10, e1349589). It is a tumour model known to express TGFb (Muraoka et al J Clin Invest. 2002 Jun. 15; 109(12): 1551-1559.)

Doses and Time Points.

The EMT6 study was performed by Oncodesign (Montreal, Canada). Four groups were used Group 1, 10 animals 70 µg doses of Isotype control mouse IgG1 (MOPC-21, BioXcell). Group 2, 6 animals give Fc-CLPTM1 at 70 µg doses. Group 3 10 animals given anti-PD1 (RMP1-14, BioXcell) at 200 µg doses. Group 4 6 animals given 70 µg Fc-CLPTM1 and 200 µg anti-PD1. Animals were dosed twice weekly (i.v.) for a three week duration and tumour size was monitored by calipering. Treatment started on day 11 after randomization of animals.

Animals administered the Fc-CLPTM1 fusion protein showed reduced tumour growth relative to animals administered an Fc isotype control protein (FIGS. 10 A and B). Animals administered the Fc-CLPTM1 fusion protein and an anti-PD1 antibody as a combination therapy showed a greater reduction in tumour growth relative to the isotype control and relative to individual treatment with the Fc-CLPTM1 fusion protein or anti-PD1 antibody alone (FIG. 10, A-D). Four out of six animals in the combination treatment group were tumour free at day 39 of the study. No animals in other groups were tumour free at this time. A Chi-squared test of responders vs. non-responders as defined by having a smaller tumor size at the end of the study compared to the size at treatment start was significant when comparing isotype control group with the Fc-CLPTM1 and anti-PD1 combination group, p-value 0.0029.

The invention claimed is:

1. A bifunctional construct comprising:
   a) a polypeptide capable of binding to TGF-β and inhibiting the interaction of TGF-β with CLPTM1, wherein said polypeptide is or comprises an amino acid sequence as set forth in SEQ ID NO: 243, wherein said polypeptide is linked to a fusion partner which is an Fc of an immunoglobulin or albumin; and
   b) an immune checkpoint inhibitor;
   wherein said immune checkpoint inhibitor is linked to said polypeptide.

2. The construct of claim 1, wherein said immune checkpoint inhibitor is an antibody that binds human protein Programmed Death Ligand 1 (PD-L1) or Programmed cell death protein 1 (PD-1).

3. A method of treating a cancer associated with an elevated level of TGF-β in a subject, wherein the elevated level of TGF-β is increased at the site of the cancer compared to elsewhere in the body of the subject or compared to the level at that site in a healthy subject, which method comprises administering to the subject an effective amount of a fusion protein comprising a polypeptide which is capable of inhibiting the interaction of TGF-β with CLPTM1, wherein said polypeptide is or comprises an amino acid sequence as set forth in SEQ ID NO: 243, wherein said polypeptide is linked to a fusion partner which is an Fc of an immunoglobulin or albumin, and wherein said cancer is selected from the group consisting of bladder cancer, breast cancer, glioblastoma, head and neck cancer, kidney clear cell cancer, B-cell lymphoma, glioma, mesothelioma, ovarian cancer, pancreatic cancer, prostate cancer, sarcoma, thyroid cancer, uterine cancer, myeloid leukaemia, lung adenocarcinoma, squamous carcinoma of the lung or larynx, adenocarcinoma of the stomach, colon, duodenum or rectum, and melanoma.

4. The method according to claim 3, wherein said cancer is not associated with an elevated level of GDF15.

5. The method according to claim 3, wherein the polypeptide is in the form of a dimer or higher multimeric form.

6. The method according to claim 3, wherein the fusion protein is administered to said subject in combination with an immune checkpoint inhibitor.

7. The method of claim 3, wherein the fusion partner is linked to the polypeptide by a linker sequence.

8. The method of claim 3, wherein the polypeptide is fused to the C-terminus of the fusion partner.

9. A method of detecting a subject in need of therapy or prophylaxis by a polypeptide which is capable of inhibiting the interaction of TGF-β with CLPTM1, or of assessing or monitoring a said method of therapy or prophylaxis, wherein said polypeptide is or comprises an amino acid sequence as set forth in SEQ ID NO: 243, wherein said polypeptide is linked to a fusion partner which is an Fc of an immunoglobulin or albumin, said method comprising detecting an interaction between TGF-β and CLPTM1, and/or an effect of said interaction, optionally wherein the interaction between TGF-β and CLPTM1 is detected by an in situ proximity ligation assay.

10. The method of claim 9, wherein said method is for detecting a subject having or at risk of developing a condition associated with an elevated level of TGF-β, said method comprising detecting in said subject an interaction of TGF-β with CLPTM1, and/or an effect of said interaction.

* * * * *

UNITED STATES PATENT AND TRADEMARK OFFICE
CERTIFICATE OF CORRECTION

| | | |
|---|---|---|
| PATENT NO. | : 11,406,665 B2 | |
| APPLICATION NO. | : 16/477423 | |
| DATED | : August 9, 2022 | |
| INVENTOR(S) | : Johan Erik Simon Fredriksson et al. | |

It is certified that error appears in the above-identified patent and that said Letters Patent is hereby corrected as shown below:

On the Title Page

Item (30), change "1700567" to --1700567.9--.

Signed and Sealed this
Eighth Day of November, 2022

Katherine Kelly Vidal
*Director of the United States Patent and Trademark Office*